US012788358B2

(12) United States Patent
Telfort

(10) Patent No.: US 12,788,358 B2
(45) **Date of Patent: *Nov. 10, 2026**

(54) ACOUSTIC PATIENT SENSOR COUPLER

(71) Applicant: Masimo Corporation, Irvine, CA (US)

(72) Inventor: Valery G. Telfort, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 269 days.

This patent is subject to a terminal disclaimer.

(21) Appl. No.: 18/638,177

(22) Filed: Apr. 17, 2024

(65) Prior Publication Data

US 2024/0268783 A1 Aug. 15, 2024

Related U.S. Application Data

(63) Continuation of application No. 17/241,705, filed on Apr. 27, 2021, now Pat. No. 11,992,361, which is a (Continued)

(51) Int. Cl.

| | |
|---|---|
| ***A61B 7/02*** | (2006.01) |
| ***A61B 5/257*** | (2021.01) |
| ***A61B 5/263*** | (2021.01) |
| ***A61B 7/04*** | (2006.01) |
| *A61B 5/28* | (2021.01) |

(52) U.S. Cl.

CPC ................ *A61B 7/04* (2013.01); *A61B 5/257* (2021.01); *A61B 5/263* (2021.01); *A61B 7/026* (2013.01); *A61B 5/28* (2021.01); *A61B 2562/0204* (2013.01)

(58) Field of Classification Search

None

See application file for complete search history.

(56) References Cited

U.S. PATENT DOCUMENTS 2,699,465 A 1/1955 Hamilton
3,399,467 A 9/1968 Ravin (Continued)

FOREIGN PATENT DOCUMENTS

CA 2490438 1/2004
CA 2262236 4/2008

(Continued)

OTHER PUBLICATIONS

US 8,740,816 B2, 06/2014, Telfort et al. (withdrawn)

(Continued)

*Primary Examiner* — Etsub D Berhanu

(74) *Attorney, Agent, or Firm* — Knobbe, Martens, Olson & Bear, LLP

(57) ABSTRACT

According to certain described aspects, multiple acoustic sensing elements are employed in a variety of beneficial ways to provide improved physiological monitoring, among other advantages. In various embodiments, sensing elements can be advantageously employed in a single sensor package, in multiple sensor packages, and at a variety of other strategic locations in the monitoring environment. According to other aspects, to compensate for skin elasticity and attachment variability, an acoustic sensor support is provided that includes one or more pressure equalization pathways. The pathways can provide an air-flow channel from the cavity defined by the sensing elements and frame to the ambient air pressure.

14 Claims, 26 Drawing Sheets

Related U.S. Application Data continuation of application No. 15/926,555, filed on Mar. 20, 2018, now Pat. No. 11,020,084, which is a continuation of application No. 14/030,268, filed on Sep. 18, 2013, now Pat. No. 9,955,937.

(60) Provisional application No. 61/703,731, filed on Sep. 20, 2012.

(56) References Cited

U.S. PATENT DOCUMENTS 3,682,161 A 8/1972 Alibert
3,867,925 A 2/1975 Ersek
3,951,230 A 4/1976 Littmann
3,991,304 A 11/1976 Hillsman
4,127,749 A 11/1978 Atoji et al.
4,254,302 A 3/1981 Walshe
4,326,143 A 4/1982 Guth et al.
4,381,788 A 5/1983 Douglas
4,401,125 A 8/1983 Tayor et al.
4,413,202 A 11/1983 Krempl et al.
4,474,185 A 10/1984 Diamond
4,537,200 A 8/1985 Widrow
4,576,179 A 3/1986 Manus et al.
4,578,613 A 3/1986 Dorogusker et al.
4,634,917 A 1/1987 Dvorksy et al.
4,653,498 A 3/1987 New, Jr. et al.
4,672,976 A 6/1987 Kroll
4,805,633 A 2/1989 Kotani et al.
4,827,943 A 5/1989 Bornn et al.
4,871,046 A 10/1989 Turner
4,884,809 A 12/1989 Rowan
4,924,876 A 5/1990 Cameron
4,947,853 A 8/1990 Hon
4,947,859 A 8/1990 Brewer et al.
4,960,118 A 10/1990 Pennock
4,960,128 A 10/1990 Gordon et al.
4,964,408 A 10/1990 Hink et al.
4,982,738 A 1/1991 Griebel
4,995,473 A 2/1991 Packard
5,003,605 A 3/1991 Phillipps et al.
5,033,032 A 7/1991 Houghtaling
5,036,857 A 8/1991 Semmlow et al.
5,041,187 A 8/1991 Hink et al.
5,069,213 A 12/1991 Hink et al.
5,078,151 A 1/1992 Laballery
5,140,992 A 8/1992 Zuckerwar et al.
5,143,078 A 9/1992 Mather et al.
5,163,438 A 11/1992 Gordon et al.
5,269,314 A 12/1993 Kendall et al.
5,273,036 A 12/1993 Kronberg et al.
5,278,627 A 1/1994 Aoyagi et al.
5,319,355 A 6/1994 Russek
5,333,106 A 7/1994 Lanpher et al.
5,337,744 A 8/1994 Branigan
5,341,805 A 8/1994 Stavridi et al.
5,377,676 A 1/1995 Vari et al.
5,394,877 A 3/1995 Orr
5,406,952 A 4/1995 Barnes et al.
5,428,193 A 6/1995 Mandiberg
5,431,170 A 7/1995 Mathews
5,436,499 A 7/1995 Namavar et al.
5,448,996 A 9/1995 Bellin et al.
5,452,717 A 9/1995 Branigan et al.
5,456,252 A 10/1995 Vari et al.
5,479,934 A 1/1996 Imran
5,482,036 A 1/1996 Diab et al.
5,490,505 A 2/1996 Diab et al.
5,494,043 A 2/1996 O'Sullivan et al.
5,533,511 A 7/1996 Kaspari et al.
5,534,851 A 7/1996 Russek
5,539,831 A 7/1996 Harley
5,564,108 A 10/1996 Hunsaker et al.
5,566,671 A 10/1996 Lyons
5,578,799 A 11/1996 Callahan et al.
5,590,649 A 1/1997 Caro et al.
5,602,924 A 2/1997 Durand et al.
5,632,272 A 5/1997 Diab et al.
5,638,816 A 6/1997 Kiani-Azarbayjany et al.
5,638,818 A 6/1997 Diab et al.
5,645,440 A 7/1997 Tobler et al.
5,671,914 A 9/1997 Kalkhoran et al.
5,685,299 A 11/1997 Diab et al.
5,726,440 A 3/1998 Kalkhoran et al.
5,730,140 A 3/1998 Fitch
D393,830 S 4/1998 Tobler et al.
5,737,367 A 4/1998 Wuppermann
5,738,106 A 4/1998 Yamamori et al.
5,743,262 A 4/1998 Lepper, Jr. et al.
5,747,806 A 5/1998 Khalil et al.
5,750,994 A 5/1998 Schlager
5,758,644 A 6/1998 Diab et al.
5,760,910 A 6/1998 Lepper, Jr. et al.
5,769,785 A 6/1998 Diab et al.
5,782,757 A 7/1998 Diab et al.
5,785,659 A 7/1998 Caro et al.
5,791,347 A 8/1998 Flaherty et al.
5,810,734 A 9/1998 Caro et al.
5,812,678 A 9/1998 Scalise et al.
5,823,950 A 10/1998 Diab et al.
5,825,895 A 10/1998 Grasfield et al.
5,830,131 A 11/1998 Caro et al.
5,833,618 A 11/1998 Caro et al.
5,860,919 A 1/1999 Kiani-Azarbayjany et al.
5,890,929 A 4/1999 Mills et al.
5,904,654 A 5/1999 Wohltmann et al.
5,912,656 A 6/1999 Tham et al.
5,919,134 A 7/1999 Diab
5,921,941 A 7/1999 Longobardo et al.
5,934,925 A 8/1999 Tobler et al.
5,940,182 A 8/1999 Lepper, Jr. et al.
5,977,538 A 11/1999 Unger et al.
5,987,343 A 11/1999 Kinast
5,989,193 A 11/1999 Sullivan
5,995,855 A 11/1999 Kiani et al.
5,997,343 A 12/1999 Mills et al.
6,002,952 A 12/1999 Diab et al.
6,010,937 A 1/2000 Karam et al.
6,011,986 A 1/2000 Diab et al.
6,027,452 A 2/2000 Flaherty et al.
6,036,642 A 3/2000 Diab et al.
6,040,578 A 3/2000 Malin et al.
6,045,509 A 4/2000 Caro et al.
6,048,323 A 4/2000 Hon
6,066,204 A 5/2000 Haven
6,067,462 A 5/2000 Diab et al.
6,081,735 A 6/2000 Diab et al.
6,083,156 A 7/2000 Lisiecki
6,088,607 A 7/2000 Diab et al.
6,091,973 A 7/2000 Colla et al.
6,106,481 A 8/2000 Cohen
6,110,522 A 8/2000 Lepper, Jr. et al.
6,115,673 A 9/2000 Malin et al.
6,124,597 A 9/2000 Shehada et al.
6,128,521 A 10/2000 Marro et al.
6,129,675 A 10/2000 Jay
6,144,868 A 11/2000 Parker
6,151,516 A 11/2000 Kiani-Azarbayjany et al.
6,152,754 A 11/2000 Gerhardt et al.
6,157,850 A 12/2000 Diab et al.
6,165,005 A 12/2000 Mills et al.
6,168,568 B1 1/2001 Gavriely
6,178,343 B1 1/2001 Bindszus et al.
6,184,521 B1 2/2001 Coffin, IV et al.
6,206,830 B1 3/2001 Diab et al.
6,210,344 B1 4/2001 Perin et al.
6,229,856 B1 5/2001 Diab et al.
6,232,609 B1 5/2001 Snyder et al.
6,236,872 B1 5/2001 Diab et al.
6,241,683 B1 6/2001 Macklem et al.
6,248,083 B1 6/2001 Smith et al.
6,253,097 B1 6/2001 Aronow et al.
6,255,708 B1 7/2001 Sudharsanan et al.
6,256,523 B1 7/2001 Diab et al.

(56) References Cited

U.S. PATENT DOCUMENTS

| | | | |
|---|---|---|---|
| 6,261,237 | B1 | 7/2001 | Swanson et al. |
| 6,261,238 | B1 | 7/2001 | Gavriely |
| 6,263,222 | B1 | 7/2001 | Diab et al. |
| 6,271,760 | B1 | 8/2001 | Watanabe et al. |
| 6,275,594 | B1 | 8/2001 | Senoo et al. |
| 6,278,522 | B1 | 8/2001 | Lepper, Jr. et al. |
| 6,280,213 | B1 | 8/2001 | Tobler et al. |
| 6,280,381 | B1 | 8/2001 | Malin et al. |
| 6,285,896 | B1 | 9/2001 | Tobler et al. |
| 6,295,365 | B1 | 9/2001 | Ota |
| 6,301,493 | B1 | 10/2001 | Marro et al. |
| 6,308,089 | B1 | 10/2001 | von der Ruhr et al. |
| 6,317,627 | B1 | 11/2001 | Ennen et al. |
| 6,321,100 | B1 | 11/2001 | Parker |
| 6,325,761 | B1 | 12/2001 | Jay |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,411,014 | B1 | 6/2002 | Toda |
| 6,411,373 | B1 | 6/2002 | Garside et al. |
| 6,415,033 | B1 | 7/2002 | Halleck et al. |
| 6,415,167 | B1 | 7/2002 | Blank et al. |
| 6,423,013 | B1 | 7/2002 | Bakker et al. |
| 6,430,437 | B1 | 8/2002 | Marro |
| 6,430,525 | B1 | 8/2002 | Weber et al. |
| 6,438,238 | B1 | 8/2002 | Callahan |
| 6,463,311 | B1 | 10/2002 | Diab |
| 6,470,199 | B1 | 10/2002 | Kopotic et al. |
| 6,486,588 | B2 | 11/2002 | Doron et al. |
| 6,487,429 | B2 | 11/2002 | Hockersmith et al. |
| 6,501,975 | B2 | 12/2002 | Diab et al. |
| 6,505,059 | B1 | 1/2003 | Kollias et al. |
| 6,515,273 | B2 | 2/2003 | Al-Ali |
| 6,517,497 | B2 | 2/2003 | Rymut et al. |
| 6,519,487 | B1 | 2/2003 | Parker |
| 6,525,386 | B1 | 2/2003 | Mills et al. |
| 6,526,300 | B1 | 2/2003 | Kiani et al. |
| 6,534,012 | B1 | 3/2003 | Hazen et al. |
| 6,541,756 | B2 | 4/2003 | Schulz et al. |
| 6,542,764 | B1 | 4/2003 | Al-Ali et al. |
| 6,560,470 | B1 | 5/2003 | Pologe |
| 6,571,113 | B1 | 5/2003 | Fein et al. |
| 6,580,086 | B1 | 6/2003 | Schulz et al. |
| 6,584,336 | B1 | 6/2003 | Ali et al. |
| 6,587,196 | B1 | 7/2003 | Stippick et al. |
| 6,587,199 | B1 | 7/2003 | Luu |
| 6,597,932 | B2 | 7/2003 | Tian et al. |
| 6,597,933 | B2 | 7/2003 | Kiani et al. |
| 6,606,511 | B1 | 8/2003 | Ali et al. |
| 6,632,181 | B2 | 10/2003 | Flaherty et al. |
| 6,635,559 | B2 | 10/2003 | Greenwald et al. |
| 6,639,668 | B1 | 10/2003 | Trepagnier |
| 6,640,116 | B2 | 10/2003 | Diab |
| 6,640,117 | B2 | 10/2003 | Makarewicz et al. |
| 6,643,530 | B2 | 11/2003 | Diab et al. |
| 6,650,917 | B2 | 11/2003 | Diab et al. |
| 6,654,624 | B2 | 11/2003 | Diab et al. |
| 6,658,276 | B2 | 12/2003 | Kiani et al. |
| 6,661,161 | B1 | 12/2003 | Lanzo et al. |
| 6,671,531 | B2 | 12/2003 | Al-Ali |
| 6,678,543 | B2 | 1/2004 | Diab et al. |
| 6,684,090 | B2 | 1/2004 | Ali et al. |
| 6,684,091 | B2 | 1/2004 | Parker |
| 6,697,656 | B1 | 2/2004 | Al-Ali |
| 6,697,657 | B1 | 2/2004 | Shehada et al. |
| 6,697,658 | B2 | 2/2004 | Al-Ali |
| RE38,476 | E | 3/2004 | Diab et al. |
| 6,699,194 | B1 | 3/2004 | Diab et al. |
| 6,702,755 | B1 | 3/2004 | Stasz et al. |
| 6,714,804 | B2 | 3/2004 | Al-Ali et al. |
| RE38,492 | E | 4/2004 | Diab et al. |
| 6,721,582 | B2 | 4/2004 | Trepagnier et al. |
| 6,721,585 | B1 | 4/2004 | Parker |
| 6,725,074 | B1 | 4/2004 | Kästle |
| 6,725,075 | B2 | 4/2004 | Al-Ali |
| 6,728,560 | B2 | 4/2004 | Kollias et al. |
| 6,735,459 | B2 | 5/2004 | Parker |
| 6,738,652 | B2 | 5/2004 | Mattu et al. |
| 6,745,060 | B2 | 6/2004 | Diab et al. |
| 6,760,607 | B2 | 7/2004 | Al-Ali |
| 6,770,028 | B1 | 8/2004 | Ali et al. |
| 6,771,994 | B2 | 8/2004 | Kiani et al. |
| 6,788,965 | B2 | 9/2004 | Ruchti et al. |
| 6,792,300 | B1 | 9/2004 | Diab et al. |
| 6,813,511 | B2 | 11/2004 | Diab et al. |
| 6,816,241 | B2 | 11/2004 | Grubisic |
| 6,816,741 | B2 | 11/2004 | Diab |
| 6,816,744 | B2 | 11/2004 | Garfield et al. |
| 6,822,564 | B2 | 11/2004 | Al-Ali |
| 6,826,419 | B2 | 11/2004 | Diab et al. |
| 6,830,711 | B2 | 12/2004 | Mills et al. |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,861,639 | B2 | 3/2005 | Al-Ali |
| 6,869,402 | B2 | 3/2005 | Arnold |
| 6,876,931 | B2 | 4/2005 | Lorenz et al. |
| 6,898,452 | B2 | 5/2005 | Al-Ali et al. |
| 6,920,345 | B2 | 7/2005 | Al-Ali et al. |
| 6,931,268 | B1 | 8/2005 | Kiani-Azarbayjany et al. |
| 6,934,570 | B2 | 8/2005 | Kiani et al. |
| 6,937,736 | B2 | 8/2005 | Toda |
| 6,939,305 | B2 | 9/2005 | Flaherty et al. |
| 6,943,348 | B1 | 9/2005 | Coffin IV |
| 6,950,687 | B2 | 9/2005 | Al-Ali |
| 6,954,971 | B1 | 10/2005 | Bryant et al. |
| 6,956,649 | B2 | 10/2005 | Acosta et al. |
| 6,961,598 | B2 | 11/2005 | Diab |
| 6,970,792 | B1 | 11/2005 | Diab |
| 6,979,812 | B2 | 12/2005 | Al-Ali |
| 6,985,764 | B2 | 1/2006 | Mason et al. |
| 6,990,364 | B2 | 1/2006 | Ruchti et al. |
| 6,993,371 | B2 | 1/2006 | Kiani et al. |
| 6,996,427 | B2 | 2/2006 | Ali et al. |
| 6,998,247 | B2 | 2/2006 | Monfre et al. |
| 6,999,904 | B2 | 2/2006 | Weber et al. |
| 7,003,338 | B2 | 2/2006 | Weber et al. |
| 7,003,339 | B2 | 2/2006 | Diab et al. |
| 7,015,451 | B2 | 3/2006 | Dalke et al. |
| 7,020,508 | B2 | 3/2006 | Stivoric et al. |
| 7,024,233 | B2 | 4/2006 | Ali et al. |
| 7,027,849 | B2 | 4/2006 | Al-Ali |
| 7,030,749 | B2 | 4/2006 | Al-Ali |
| 7,035,684 | B2 | 4/2006 | Lee |
| 7,039,449 | B2 | 5/2006 | Al-Ali |
| 7,041,060 | B2 | 5/2006 | Flaherty et al. |
| 7,044,918 | B2 | 5/2006 | Diab |
| 7,048,687 | B1 | 5/2006 | Reuss et al. |
| 7,067,893 | B2 | 6/2006 | Mills et al. |
| D526,719 | S | 8/2006 | Richie, Jr. et al. |
| 7,096,052 | B2 | 8/2006 | Mason et al. |
| 7,096,054 | B2 | 8/2006 | Abdul-Hafiz et al. |
| 7,096,060 | B2 | 8/2006 | Arand et al. |
| 7,110,804 | B2 | 9/2006 | Baumer et al. |
| D529,616 | S | 10/2006 | Deros et al. |
| 7,132,641 | B2 | 11/2006 | Schulz et al. |
| 7,133,710 | B2 | 11/2006 | Acosta et al. |
| 7,142,901 | B2 | 11/2006 | Kiani et al. |
| 7,149,561 | B2 | 12/2006 | Diab |
| 7,186,966 | B2 | 3/2007 | Al-Ali |
| 7,190,261 | B2 | 3/2007 | Al-Ali |
| 7,190,945 | B1 | 3/2007 | Crisafulli |
| 7,215,984 | B2 | 5/2007 | Diab et al. |
| 7,215,986 | B2 | 5/2007 | Diab et al. |
| 7,221,971 | B2 | 5/2007 | Diab et al. |
| 7,225,006 | B2 | 5/2007 | Al-Ali et al. |
| 7,225,007 | B2 | 5/2007 | Al-Ali et al. |
| RE39,672 | E | 6/2007 | Shehada et al. |

(56) References Cited

U.S. PATENT DOCUMENTS 7,239,905 B2 7/2007 Kiani-Azarbayjany et al.
7,245,953 B1 7/2007 Parker
7,246,069 B1 7/2007 O'Hanlon et al.
7,254,429 B2 8/2007 Schurman et al.
7,254,431 B2 8/2007 Al-Ali et al.
7,254,433 B2 8/2007 Diab et al.
7,254,434 B2 8/2007 Schulz et al.
7,270,126 B2 9/2007 Wallace et al.
7,272,425 B2 9/2007 Al-Ali
7,274,955 B2 9/2007 Kiani et al.
D554,263 S 10/2007 Al-Ali et al.
7,280,858 B2 10/2007 Al-Ali et al.
7,289,835 B2 10/2007 Mansfield et al.
7,292,883 B2 11/2007 De Felice et al.
7,295,866 B2 11/2007 Al-Ali
7,328,053 B1 2/2008 Diab et al.
7,332,784 B2 2/2008 Mills et al.
7,340,287 B2 3/2008 Mason et al.
7,341,559 B2 3/2008 Schulz et al.
7,343,186 B2 3/2008 Lamego et al.
D566,282 S 4/2008 Al-Ali et al.
7,355,512 B1 4/2008 Al-Ali
7,356,365 B2 4/2008 Schurman
7,361,148 B2 4/2008 Narimatsu
7,368,855 B2 5/2008 Orten
7,371,981 B2 5/2008 Abdul-Hafiz
7,373,193 B2 5/2008 Al-Ali et al.
7,373,194 B2 5/2008 Weber et al.
7,376,453 B1 5/2008 Diab et al.
7,377,794 B2 5/2008 Al-Ali et al.
7,377,899 B2 5/2008 Weber et al.
7,383,070 B2 6/2008 Diab et al.
7,395,158 B2 7/2008 Monfre et al.
7,415,297 B2 8/2008 Al-Ali et al.
7,428,432 B2 9/2008 Ali et al.
7,438,683 B2 10/2008 Al-Ali et al.
7,440,787 B2 10/2008 Diab
7,454,240 B2 11/2008 Diab et al.
7,467,002 B2 12/2008 Weber et al.
7,469,157 B2 12/2008 Diab et al.
7,469,158 B2 12/2008 Cutler et al.
7,471,969 B2 12/2008 Diab et al.
7,471,971 B2 12/2008 Diab et al.
7,483,729 B2 1/2009 Al-Ali et al.
7,483,730 B2 1/2009 Diab et al.
7,489,958 B2 2/2009 Diab et al.
7,496,391 B2 2/2009 Diab et al.
7,496,393 B2 2/2009 Diab et al.
D587,657 S 3/2009 Al-Ali et al.
7,499,741 B2 3/2009 Diab et al.
7,499,835 B2 3/2009 Weber et al.
7,500,950 B2 3/2009 Al-Ali et al.
7,509,154 B2 3/2009 Diab et al.
7,509,494 B2 3/2009 Al-Ali
7,510,849 B2 3/2009 Schurman et al.
7,514,725 B2 4/2009 Wojtczuk et al.
7,515,044 B2 4/2009 Welch et al.
7,519,406 B2 4/2009 Blank et al.
7,526,328 B2 4/2009 Diab et al.
D592,507 S 5/2009 Wachman et al.
7,530,942 B1 5/2009 Diab
7,530,949 B2 5/2009 Al Ali et al.
7,530,955 B2 5/2009 Diab et al.
7,563,110 B2 7/2009 Al-Ali et al.
7,593,230 B2 9/2009 Abul-Haj et al.
7,596,398 B2 9/2009 Al-Ali et al.
7,606,608 B2 10/2009 Blank et al.
7,618,375 B2 11/2009 Flaherty et al.
7,620,674 B2 11/2009 Ruchti et al.
D606,659 S 12/2009 Kiani et al.
7,625,117 B2 12/2009 Haslett et al.
7,629,039 B2 12/2009 Eckerbom et al.
7,640,140 B2 12/2009 Ruchti et al.
7,647,083 B2 1/2010 Al-Ali et al.
D609,193 S 2/2010 Al-Ali et al.
7,662,105 B2 2/2010 Hatlestad
7,668,588 B2 2/2010 Kovacs
D614,305 S 4/2010 Al-Ali et al.
7,697,966 B2 4/2010 Monfre et al.
7,698,105 B2 4/2010 Ruchti et al.
RE41,317 E 5/2010 Parker
RE41,333 E 5/2010 Blank et al.
7,729,733 B2 6/2010 Al-Ali et al.
7,734,320 B2 6/2010 Al-Ali
7,761,127 B2 7/2010 Al-Ali et al.
7,761,128 B2 7/2010 Al-Ali et al.
7,764,982 B2 7/2010 Dalke et al.
D621,516 S 8/2010 Kiani et al.
7,783,056 B2 8/2010 Wilmink
7,791,155 B2 9/2010 Diab
7,801,581 B2 9/2010 Diab
7,806,226 B2 10/2010 Drummond et al.
7,822,452 B2 10/2010 Schurman et al.
RE41,912 E 11/2010 Parker
7,844,313 B2 11/2010 Kiani et al.
7,844,314 B2 11/2010 Al-Ali
7,844,315 B2 11/2010 Al-Ali
7,860,553 B2 12/2010 Govari et al.
7,865,222 B2 1/2011 Weber et al.
7,873,497 B2 1/2011 Weber et al.
7,880,606 B2 2/2011 Al-Ali
7,880,626 B2 2/2011 Al-Ali et al.
7,891,355 B2 2/2011 Al-Ali et al.
7,894,868 B2 2/2011 Al-Ali et al.
7,899,507 B2 3/2011 Al-Ali et al.
7,903,825 B1 3/2011 Melanson
7,904,132 B2 3/2011 Weber et al.
7,909,772 B2 3/2011 Popov et al.
7,910,875 B2 3/2011 Al-Ali
7,919,713 B2 4/2011 Al-Ali et al.
7,937,128 B2 5/2011 Al-Ali
7,937,129 B2 5/2011 Mason et al.
7,937,130 B2 5/2011 Diab et al.
7,940,937 B2 5/2011 Smith
7,941,199 B2 5/2011 Kiani
7,951,086 B2 5/2011 Flaherty et al.
7,957,780 B2 6/2011 Lamego et al.
7,962,188 B2 6/2011 Kiani et al.
7,962,190 B1 6/2011 Diab et al.
7,976,472 B2 7/2011 Kiani
7,976,480 B2 7/2011 Grajales et al.
7,988,637 B2 8/2011 Diab
7,988,688 B2 8/2011 Webb et al.
7,990,382 B2 8/2011 Kiani
7,991,165 B2 8/2011 Kassal et al.
7,991,446 B2 8/2011 Ali et al.
8,000,761 B2 8/2011 Al-Ali
8,008,088 B2 8/2011 Bellott et al.
RE42,753 E 9/2011 Kiani-Azarbayjany et al.
8,019,400 B2 9/2011 Diab et al.
8,028,701 B2 10/2011 Al-Ali et al.
8,029,765 B2 10/2011 Bellott et al.
8,036,727 B2 10/2011 Schurman et al.
8,036,728 B2 10/2011 Diab et al.
8,046,040 B2 10/2011 Ali et al.
8,046,041 B2 10/2011 Diab et al.
8,046,042 B2 10/2011 Diab et al.
8,048,040 B2 11/2011 Kiani
8,050,728 B2 11/2011 Al-Ali et al.
8,092,396 B2 1/2012 Bagha et al.
8,108,039 B2 1/2012 Saliga et al.
RE43,169 E 2/2012 Parker
8,116,841 B2 2/2012 Bly et al.
8,118,620 B2 2/2012 Al-Ali et al.
8,121,673 B2 2/2012 Tran
8,126,528 B2 2/2012 Diab et al.
8,128,572 B2 3/2012 Diab et al.
8,130,105 B2 3/2012 Al-Ali et al.
8,145,287 B2 3/2012 Diab et al.
8,150,487 B2 4/2012 Diab et al.
8,175,672 B2 5/2012 Parker
8,180,420 B2 5/2012 Diab et al.
8,182,443 B1 5/2012 Kiani
8,185,180 B2 5/2012 Diab et al.

(56) References Cited

U.S. PATENT DOCUMENTS

| | | | |
|---|---|---|---|
| 8,190,223 | B2 | 5/2012 | Al-Ali et al. |
| 8,190,227 | B2 | 5/2012 | Diab et al. |
| 8,203,438 | B2 | 6/2012 | Kiani et al. |
| 8,203,704 | B2 | 6/2012 | Merritt et al. |
| 8,204,566 | B2 | 6/2012 | Schurman et al. |
| 8,214,007 | B2 | 7/2012 | Baker et al. |
| 8,219,172 | B2 | 7/2012 | Schurman et al. |
| 8,224,411 | B2 | 7/2012 | Al-Ali et al. |
| 8,228,181 | B2 | 7/2012 | Al-Ali |
| 8,229,532 | B2 | 7/2012 | Davis |
| 8,229,533 | B2 | 7/2012 | Diab et al. |
| 8,233,955 | B2 | 7/2012 | Al-Ali et al. |
| 8,241,223 | B2 | 8/2012 | Gavriely et al. |
| 8,244,325 | B2 | 8/2012 | Al-Ali et al. |
| 8,255,026 | B1 | 8/2012 | Al-Ali |
| 8,255,027 | B2 | 8/2012 | Al-Ali et al. |
| 8,255,028 | B2 | 8/2012 | Al-Ali et al. |
| 8,260,577 | B2 | 9/2012 | Weber et al. |
| 8,265,291 | B2 | 9/2012 | Bridger et al. |
| 8,265,723 | B1 | 9/2012 | McHale et al. |
| 8,274,360 | B2 | 9/2012 | Sampath et al. |
| 8,275,140 | B2 | 9/2012 | Smith |
| 8,280,473 | B2 | 10/2012 | Al-Ali |
| 8,301,217 | B2 | 10/2012 | Al-Ali et al. |
| 8,306,596 | B2 | 11/2012 | Schurman et al. |
| 8,310,336 | B2 | 11/2012 | Muhsin et al. |
| 8,315,683 | B2 | 11/2012 | Al-Ali et al. |
| 8,320,576 | B1 | 11/2012 | Abbruscato |
| RE43,860 | E | 12/2012 | Parker |
| 8,337,403 | B2 | 12/2012 | Al-Ali et al. |
| 8,346,330 | B2 | 1/2013 | Lamego |
| 8,353,842 | B2 | 1/2013 | Al-Ali et al. |
| 8,355,766 | B2 | 1/2013 | MacNeish, III et al. |
| 8,359,080 | B2 | 1/2013 | Diab et al. |
| 8,364,223 | B2 | 1/2013 | Al-Ali et al. |
| 8,364,226 | B2 | 1/2013 | Diab et al. |
| 8,374,665 | B2 | 2/2013 | Lamego |
| 8,385,995 | B2 | 2/2013 | Al-Ali et al. |
| 8,385,996 | B2 | 2/2013 | Smith et al. |
| 8,388,353 | B2 | 3/2013 | Kiani et al. |
| 8,396,228 | B2 | 3/2013 | Bilan |
| 8,399,822 | B2 | 3/2013 | Al-Ali |
| 8,401,602 | B2 | 3/2013 | Kiani |
| 8,403,865 | B2 | 3/2013 | Halperin et al. |
| 8,405,608 | B2 | 3/2013 | Al-Ali et al. |
| 8,414,499 | B2 | 4/2013 | Al-Ali et al. |
| 8,418,524 | B2 | 4/2013 | Al-Ali |
| 8,423,106 | B2 | 4/2013 | Lamego et al. |
| 8,428,967 | B2 | 4/2013 | Olsen et al. |
| 8,430,817 | B1 | 4/2013 | Al-Ali et al. |
| 8,437,825 | B2 | 5/2013 | Dalvi et al. |
| 8,449,469 | B2 | 5/2013 | Banet et al. |
| 8,455,290 | B2 | 6/2013 | Siskavich |
| 8,457,703 | B2 | 6/2013 | Al-Ali |
| 8,457,707 | B2 | 6/2013 | Kiani |
| 8,463,349 | B2 | 6/2013 | Diab et al. |
| 8,466,286 | B2 | 6/2013 | Bellott et al. |
| 8,471,713 | B2 | 6/2013 | Poeze et al. |
| 8,473,020 | B2 | 6/2013 | Kiani et al. |
| 8,483,787 | B2 | 7/2013 | Al-Ali et al. |
| 8,489,364 | B2 | 7/2013 | Weber et al. |
| 8,491,489 | B2 | 7/2013 | Shin et al. |
| 8,498,684 | B2 | 7/2013 | Weber et al. |
| 8,504,128 | B2 | 8/2013 | Blank et al. |
| 8,509,867 | B2 | 8/2013 | Workman et al. |
| 8,515,509 | B2 | 8/2013 | Bruinsma et al. |
| 8,517,981 | B2 | 8/2013 | Zornow |
| 8,523,781 | B2 | 9/2013 | Al-Ali |
| 8,526,665 | B2 | 9/2013 | Lutz et al. |
| 8,529,301 | B2 | 9/2013 | Al-Ali et al. |
| 8,532,727 | B2 | 9/2013 | Ali et al. |
| 8,532,728 | B2 | 9/2013 | Diab et al. |
| D692,145 | S | 10/2013 | Al-Ali et al. |
| 8,547,209 | B2 | 10/2013 | Kiani et al. |
| 8,548,548 | B2 | 10/2013 | Al-Ali |
| 8,548,549 | B2 | 10/2013 | Schurman et al. |
| 8,548,550 | B2 | 10/2013 | Al-Ali et al. |
| 8,560,032 | B2 | 10/2013 | Al-Ali et al. |
| 8,560,034 | B1 | 10/2013 | Diab et al. |
| 8,570,167 | B2 | 10/2013 | Al-Ali |
| 8,570,503 | B2 | 10/2013 | Vo et al. |
| 8,571,617 | B2 | 10/2013 | Reichgott et al. |
| 8,571,618 | B1 | 10/2013 | Lamego et al. |
| 8,571,619 | B2 | 10/2013 | Al-Ali et al. |
| 8,577,431 | B2 | 11/2013 | Lamego et al. |
| 8,581,732 | B2 | 11/2013 | Al-Ali et al. |
| 8,584,345 | B2 | 11/2013 | Al-Ali et al. |
| 8,588,880 | B2 | 11/2013 | Abdul-Hafiz et al. |
| 8,600,467 | B2 | 12/2013 | Al-Ali et al. |
| 8,606,342 | B2 | 12/2013 | Diab |
| 8,626,255 | B2 | 1/2014 | Al-Ali et al. |
| 8,630,691 | B2 | 1/2014 | Lamego et al. |
| 8,634,889 | B2 | 1/2014 | Al-Ali et al. |
| 8,641,595 | B2 | 2/2014 | Basinger |
| 8,641,631 | B2 | 2/2014 | Sierra et al. |
| 8,652,060 | B2 | 2/2014 | Al-Ali |
| 8,663,107 | B2 | 3/2014 | Kiani |
| 8,666,468 | B1 | 3/2014 | Al-Ali |
| 8,667,967 | B2 | 3/2014 | Al-Ali et al. |
| 8,670,811 | B2 | 3/2014 | O'Reilly |
| 8,670,814 | B2 | 3/2014 | Diab et al. |
| 8,676,286 | B2 | 3/2014 | Weber et al. |
| 8,682,407 | B2 | 3/2014 | Al-Ali |
| RE44,823 | E | 4/2014 | Parker |
| RE44,875 | E | 4/2014 | Kiani et al. |
| 8,688,183 | B2 | 4/2014 | Bruinsma et al. |
| 8,688,189 | B2 | 4/2014 | Shennib |
| 8,690,799 | B2 | 4/2014 | Telfort et al. |
| 8,700,112 | B2 | 4/2014 | Kiani |
| 8,702,627 | B2 | 4/2014 | Telfort et al. |
| 8,706,179 | B2 | 4/2014 | Parker |
| 8,712,494 | B1 | 4/2014 | MacNeish, III et al. |
| 8,715,206 | B2 | 5/2014 | Telfort et al. |
| 8,718,735 | B2 | 5/2014 | Lamego et al. |
| 8,718,737 | B2 | 5/2014 | Diab et al. |
| 8,718,738 | B2 | 5/2014 | Blank et al. |
| 8,720,249 | B2 | 5/2014 | Al-Ali |
| 8,721,541 | B2 | 5/2014 | Al-Ali et al. |
| 8,721,542 | B2 | 5/2014 | Al-Ali et al. |
| 8,723,677 | B1 | 5/2014 | Kiani |
| 8,740,792 | B1 | 6/2014 | Kiani et al. |
| 8,754,776 | B2 | 6/2014 | Poeze et al. |
| 8,755,535 | B2 | 6/2014 | Telfort et al. |
| 8,755,856 | B2 | 6/2014 | Diab et al. |
| 8,755,872 | B1 | 6/2014 | Marinow |
| 8,761,850 | B2 | 6/2014 | Lamego |
| 8,764,671 | B2 | 7/2014 | Kiani |
| 8,768,423 | B2 | 7/2014 | Shakespeare et al. |
| 8,771,204 | B2 | 7/2014 | Telfort et al. |
| 8,777,634 | B2 | 7/2014 | Kiani et al. |
| 8,781,543 | B2 | 7/2014 | Diab et al. |
| 8,781,544 | B2 | 7/2014 | Al-Ali et al. |
| 8,781,549 | B2 | 7/2014 | Al-Ali et al. |
| 8,788,003 | B2 | 7/2014 | Schurman et al. |
| 8,790,268 | B2 | 7/2014 | Al-Ali |
| 8,801,613 | B2 | 8/2014 | Al-Ali et al. |
| 8,821,397 | B2 | 9/2014 | Al-Ali et al. |
| 8,821,415 | B2 | 9/2014 | Al-Ali et al. |
| 8,830,449 | B1 | 9/2014 | Lamego et al. |
| 8,831,700 | B2 | 9/2014 | Schurman et al. |
| 8,840,549 | B2 | 9/2014 | Al-Ali et al. |
| 8,847,740 | B2 | 9/2014 | Kiani et al. |
| 8,849,365 | B2 | 9/2014 | Smith et al. |
| 8,852,094 | B2 | 10/2014 | Al-Ali et al. |
| 8,852,994 | B2 | 10/2014 | Wojtczuk et al. |
| 8,868,147 | B2 | 10/2014 | Stippick et al. |
| 8,868,150 | B2 | 10/2014 | Al-Ali et al. |
| 8,870,792 | B2 | 10/2014 | Al-Ali et al. |
| 8,886,271 | B2 | 11/2014 | Kiani et al. |
| 8,888,539 | B2 | 11/2014 | Al-Ali et al. |
| 8,888,708 | B2 | 11/2014 | Diab et al. |
| 8,892,180 | B2 | 11/2014 | Weber et al. |
| 8,897,847 | B2 | 11/2014 | Al-Ali |
| 8,909,310 | B2 | 12/2014 | Lamego et al. |

(56) References Cited

U.S. PATENT DOCUMENTS

| | | | |
|---|---|---|---|
| 8,911,377 | B2 | 12/2014 | Al-Ali |
| 8,912,909 | B2 | 12/2014 | Al-Ali et al. |
| 8,920,317 | B2 | 12/2014 | Al-Ali et al. |
| 8,921,699 | B2 | 12/2014 | Al-Ali et al. |
| 8,922,382 | B2 | 12/2014 | Al-Ali et al. |
| 8,929,964 | B2 | 1/2015 | Al-Ali et al. |
| 8,942,777 | B2 | 1/2015 | Diab et al. |
| 8,948,834 | B2 | 2/2015 | Diab et al. |
| 8,948,835 | B2 | 2/2015 | Diab |
| 8,961,413 | B2 | 2/2015 | Teller et al. |
| 8,965,471 | B2 | 2/2015 | Lamego |
| 8,983,564 | B2 | 3/2015 | Al-Ali |
| 8,989,831 | B2 | 3/2015 | Al-Ali et al. |
| 8,996,085 | B2 | 3/2015 | Kiani et al. |
| 8,998,809 | B2 | 4/2015 | Kiani |
| 9,028,429 | B2 | 5/2015 | Telfort et al. |
| 9,037,207 | B2 | 5/2015 | Al-Ali et al. |
| 9,060,721 | B2 | 6/2015 | Reichgott et al. |
| 9,066,666 | B2 | 6/2015 | Kiani |
| 9,066,680 | B1 | 6/2015 | Al-Ali et al. |
| 9,072,474 | B2 | 7/2015 | Al-Ali et al. |
| 9,078,560 | B2 | 7/2015 | Schurman et al. |
| 9,084,569 | B2 | 7/2015 | Weber et al. |
| 9,095,316 | B2 | 8/2015 | Welch et al. |
| 9,106,038 | B2 | 8/2015 | Telfort et al. |
| 9,107,625 | B2 | 8/2015 | Telfort et al. |
| 9,107,626 | B2 | 8/2015 | Al-Ali et al. |
| 9,113,831 | B2 | 8/2015 | Al-Ali |
| 9,113,832 | B2 | 8/2015 | Al-Ali |
| 9,119,595 | B2 | 9/2015 | Lamego |
| 9,131,881 | B2 | 9/2015 | Diab et al. |
| 9,131,882 | B2 | 9/2015 | Al-Ali et al. |
| 9,131,883 | B2 | 9/2015 | Al-Ali |
| 9,131,917 | B2 | 9/2015 | Telfort et al. |
| 9,138,180 | B1 | 9/2015 | Coverston et al. |
| 9,138,182 | B2 | 9/2015 | Al-Ali et al. |
| 9,138,192 | B2 | 9/2015 | Weber et al. |
| 9,142,117 | B2 | 9/2015 | Muhsin et al. |
| 9,153,112 | B1 | 10/2015 | Kiani et al. |
| 9,153,121 | B2 | 10/2015 | Kiani et al. |
| 9,161,696 | B2 | 10/2015 | Al-Ali et al. |
| 9,161,713 | B2 | 10/2015 | Al-Ali et al. |
| 9,167,995 | B2 | 10/2015 | Lamego et al. |
| 9,176,141 | B2 | 11/2015 | Al-Ali et al. |
| 9,186,102 | B2 | 11/2015 | Bruinsma et al. |
| 9,192,312 | B2 | 11/2015 | Al-Ali |
| 9,192,329 | B2 | 11/2015 | Al-Ali |
| 9,192,351 | B1 | 11/2015 | Telfort et al. |
| 9,195,385 | B2 | 11/2015 | Al-Ali et al. |
| 9,211,072 | B2 | 12/2015 | Kiani |
| 9,211,095 | B1 | 12/2015 | Al-Ali |
| 9,218,454 | B2 | 12/2015 | Kiani et al. |
| 9,226,696 | B2 | 1/2016 | Kiani |
| 9,241,662 | B2 | 1/2016 | Al-Ali et al. |
| 9,245,668 | B1 | 1/2016 | Vo et al. |
| 9,259,185 | B2 | 2/2016 | Abdul-Hafiz et al. |
| 9,267,572 | B2 | 2/2016 | Barker et al. |
| 9,277,880 | B2 | 3/2016 | Poeze et al. |
| 9,289,167 | B2 | 3/2016 | Diab et al. |
| 9,295,421 | B2 | 3/2016 | Kiani et al. |
| 9,307,928 | B1 | 4/2016 | Al-Ali et al. |
| 9,323,894 | B2 | 4/2016 | Kiani |
| D755,392 | S | 5/2016 | Hwang et al. |
| 9,326,712 | B1 | 5/2016 | Kiani |
| 9,333,316 | B2 | 5/2016 | Kiani |
| 9,339,220 | B2 | 5/2016 | Lamego et al. |
| 9,341,565 | B2 | 5/2016 | Lamego et al. |
| 9,351,673 | B2 | 5/2016 | Diab et al. |
| 9,351,675 | B2 | 5/2016 | Al-Ali et al. |
| 9,364,181 | B2 | 6/2016 | Kiani et al. |
| 9,368,671 | B2 | 6/2016 | Wojtczuk et al. |
| 9,370,325 | B2 | 6/2016 | Al-Ali et al. |
| 9,370,326 | B2 | 6/2016 | McHale et al. |
| 9,370,335 | B2 | 6/2016 | Al-Ali et al. |
| 9,375,185 | B2 | 6/2016 | Ali et al. |
| 9,386,953 | B2 | 7/2016 | Al-Ali |
| 9,386,961 | B2 | 7/2016 | Al-Ali et al. |
| 9,392,945 | B2 | 7/2016 | Al-Ali et al. |
| 9,397,448 | B2 | 7/2016 | Al-Ali et al. |
| 9,408,542 | B1 | 8/2016 | Kinast et al. |
| 9,411,936 | B2 | 8/2016 | Landrum et al. |
| 9,436,645 | B2 | 9/2016 | Al-Ali et al. |
| 9,439,599 | B2 | 9/2016 | Thompson |
| 9,445,759 | B1 | 9/2016 | Lamego et al. |
| 9,466,919 | B2 | 10/2016 | Kiani et al. |
| 9,474,474 | B2 | 10/2016 | Lamego et al. |
| 9,480,422 | B2 | 11/2016 | Al-Ali |
| 9,480,435 | B2 | 11/2016 | Olsen |
| 9,492,110 | B2 | 11/2016 | Al-Ali et al. |
| 9,510,779 | B2 | 12/2016 | Poeze et al. |
| 9,517,024 | B2 | 12/2016 | Kiani et al. |
| 9,532,722 | B2 | 1/2017 | Lamego et al. |
| 9,538,949 | B2 | 1/2017 | Al-Ali et al. |
| 9,538,980 | B2 | 1/2017 | Telfort et al. |
| 9,549,696 | B2 | 1/2017 | Lamego et al. |
| 9,554,737 | B2 | 1/2017 | Schurman et al. |
| 9,560,996 | B2 | 2/2017 | Kiani |
| 9,560,998 | B2 | 2/2017 | Al-Ali et al. |
| 9,566,019 | B2 | 2/2017 | Al-Ali et al. |
| 9,579,039 | B2 | 2/2017 | Jansen et al. |
| 9,591,975 | B2 | 3/2017 | Dalvi et al. |
| 9,622,692 | B2 | 4/2017 | Lamego et al. |
| 9,622,693 | B2 | 4/2017 | Diab |
| D788,312 | S | 5/2017 | Al-Ali et al. |
| 9,636,055 | B2 | 5/2017 | Al Ali et al. |
| 9,636,056 | B2 | 5/2017 | Al-Ali |
| 9,649,054 | B2 | 5/2017 | Lamego et al. |
| 9,662,052 | B2 | 5/2017 | Al-Ali et al. |
| 9,668,679 | B2 | 6/2017 | Schurman et al. |
| 9,668,680 | B2 | 6/2017 | Bruinsma et al. |
| 9,668,703 | B2 | 6/2017 | Al-Ali |
| 9,675,286 | B2 | 6/2017 | Diab |
| 9,687,160 | B2 | 6/2017 | Kiani |
| 9,693,719 | B2 | 7/2017 | Al-Ali et al. |
| 9,693,737 | B2 | 7/2017 | Al-Ali |
| 9,697,928 | B2 | 7/2017 | Al-Ali et al. |
| 9,717,425 | B2 | 8/2017 | Kiani et al. |
| 9,717,458 | B2 | 8/2017 | Lamego et al. |
| 9,724,016 | B1 | 8/2017 | Al-Ali et al. |
| 9,724,024 | B2 | 8/2017 | Al-Ali |
| 9,724,025 | B1 | 8/2017 | Kiani et al. |
| 9,730,640 | B2 | 8/2017 | Diab et al. |
| 9,743,887 | B2 | 8/2017 | Al-Ali et al. |
| 9,749,232 | B2 | 8/2017 | Sampath et al. |
| 9,750,442 | B2 | 9/2017 | Olsen |
| 9,750,443 | B2 | 9/2017 | Smith et al. |
| 9,750,461 | B1 | 9/2017 | Telfort |
| 9,775,545 | B2 | 10/2017 | Al-Ali et al. |
| 9,775,546 | B2 | 10/2017 | Diab et al. |
| 9,775,570 | B2 | 10/2017 | Al-Ali |
| 9,778,079 | B1 | 10/2017 | Al-Ali et al. |
| 9,782,077 | B2 | 10/2017 | Lamego et al. |
| 9,782,110 | B2 | 10/2017 | Kiani |
| 9,787,568 | B2 | 10/2017 | Lamego et al. |
| 9,788,735 | B2 | 10/2017 | Al-Ali |
| 9,788,768 | B2 | 10/2017 | Al-Ali et al. |
| 9,795,300 | B2 | 10/2017 | Al-Ali |
| 9,795,310 | B2 | 10/2017 | Al-Ali |
| 9,795,358 | B2 | 10/2017 | Telfort et al. |
| 9,795,739 | B2 | 10/2017 | Al-Ali et al. |
| 9,801,556 | B2 | 10/2017 | Kiani |
| 9,801,588 | B2 | 10/2017 | Weber et al. |
| 9,808,188 | B1 | 11/2017 | Perea et al. |
| 9,814,418 | B2 | 11/2017 | Weber et al. |
| 9,820,691 | B2 | 11/2017 | Kiani |
| 9,833,152 | B2 | 12/2017 | Kiani et al. |
| 9,833,180 | B2 | 12/2017 | Shakespeare et al. |
| 9,839,379 | B2 | 12/2017 | Al-Ali et al. |
| 9,839,381 | B1 | 12/2017 | Weber et al. |
| 9,847,002 | B2 | 12/2017 | Kiani et al. |
| 9,847,749 | B2 | 12/2017 | Kiani et al. |
| 9,848,800 | B1 | 12/2017 | Lee et al. |
| 9,848,806 | B2 | 12/2017 | Al-Ali |
| 9,848,807 | B2 | 12/2017 | Lamego |

(56) References Cited

U.S. PATENT DOCUMENTS

| | | | |
|---|---|---|---|
| 9,861,298 | B2 | 1/2018 | Eckerbom et al. |
| 9,861,304 | B2 | 1/2018 | Al-Ali et al. |
| 9,861,305 | B1 | 1/2018 | Weber et al. |
| 9,867,578 | B2 | 1/2018 | Al-Ali et al. |
| 9,872,623 | B2 | 1/2018 | Al-Ali |
| 9,876,320 | B2 | 1/2018 | Coverston et al. |
| 9,877,650 | B2 | 1/2018 | Muhsin et al. |
| 9,877,686 | B2 | 1/2018 | Al-Ali et al. |
| 9,891,079 | B2 | 2/2018 | Dalvi |
| 9,895,107 | B2 | 2/2018 | Al-Ali et al. |
| 9,924,897 | B1 | 3/2018 | Abdul-Hafiz |
| 9,936,917 | B2 | 4/2018 | Poeze et al. |
| 9,955,937 | B2 | 5/2018 | Telfort |
| 9,965,946 | B2 | 5/2018 | Al-Ali et al. |
| 9,968,266 | B2 | 5/2018 | An et al. |
| D820,865 | S | 6/2018 | Muhsin et al. |
| 9,986,952 | B2 | 6/2018 | Dalvi et al. |
| D822,215 | S | 7/2018 | Al-Ali et al. |
| D822,216 | S | 7/2018 | Barker et al. |
| 10,010,276 | B2 | 7/2018 | Al-Ali et al. |
| 10,086,138 | B1 | 10/2018 | Novak, Jr. |
| 10,111,591 | B2 | 10/2018 | Dyell et al. |
| D833,624 | S | 11/2018 | DeJong et al. |
| 10,123,729 | B2 | 11/2018 | Dyell et al. |
| D835,282 | S | 12/2018 | Barker et al. |
| D835,283 | S | 12/2018 | Barker et al. |
| D835,284 | S | 12/2018 | Barker et al. |
| D835,285 | S | 12/2018 | Barker et al. |
| 10,149,616 | B2 | 12/2018 | Al-Ali et al. |
| 10,154,815 | B2 | 12/2018 | Al-Ali et al. |
| 10,159,412 | B2 | 12/2018 | Lamego et al. |
| 10,188,348 | B2 | 1/2019 | Al-Ali et al. |
| RE47,218 | E | 2/2019 | Al-Ali |
| RE47,244 | E | 2/2019 | Kiani et al. |
| RE47,249 | E | 2/2019 | Kiani et al. |
| 10,205,291 | B2 | 2/2019 | Scruggs et al. |
| 10,226,187 | B2 | 3/2019 | Al-Ali et al. |
| 10,231,657 | B2 | 3/2019 | Al-Ali et al. |
| 10,231,670 | B2 | 3/2019 | Blank et al. |
| RE47,353 | E | 4/2019 | Kiani et al. |
| 10,279,247 | B2 | 5/2019 | Kiani |
| 10,292,664 | B2 | 5/2019 | Al-Ali |
| 10,299,720 | B2 | 5/2019 | Brown et al. |
| 10,327,337 | B2 | 6/2019 | Schmidt et al. |
| 10,327,713 | B2 | 6/2019 | Barker et al. |
| 10,332,630 | B2 | 6/2019 | Al-Ali |
| 10,383,520 | B2 | 8/2019 | Wojtczuk et al. |
| 10,383,527 | B2 | 8/2019 | Al-Ali |
| 10,388,120 | B2 | 8/2019 | Muhsin et al. |
| D864,120 | S | 10/2019 | Forrest et al. |
| 10,441,181 | B1 | 10/2019 | Telfort et al. |
| 10,441,196 | B2 | 10/2019 | Eckerbom et al. |
| 10,448,844 | B2 | 10/2019 | Al-Ali et al. |
| 10,448,871 | B2 | 10/2019 | Al-Ali et al. |
| 10,456,038 | B2 | 10/2019 | Lamego et al. |
| 10,463,340 | B2 | 11/2019 | Telfort et al. |
| 10,471,159 | B1 | 11/2019 | Lapotko et al. |
| 10,505,311 | B2 | 12/2019 | Al-Ali et al. |
| 10,524,738 | B2 | 1/2020 | Olsen |
| 10,532,174 | B2 | 1/2020 | Al-Ali |
| 10,537,285 | B2 | 1/2020 | Shreim et al. |
| 10,542,903 | B2 | 1/2020 | Al-Ali et al. |
| 10,555,678 | B2 | 2/2020 | Dalvi et al. |
| 10,568,553 | B2 | 2/2020 | O'Neil et al. |
| RE47,882 | E | 3/2020 | Al-Ali |
| 10,608,817 | B2 | 3/2020 | Haider et al. |
| D880,477 | S | 4/2020 | Forrest et al. |
| 10,617,302 | B2 | 4/2020 | Al-Ali et al. |
| 10,617,335 | B2 | 4/2020 | Al-Ali et al. |
| 10,637,181 | B2 | 4/2020 | Al-Ali et al. |
| D886,849 | S | 6/2020 | Muhsin et al. |
| D887,548 | S | 6/2020 | Abdul-Hafiz et al. |
| D887,549 | S | 6/2020 | Abdul-Hafiz et al. |
| 10,667,764 | B2 | 6/2020 | Ahmed et al. |
| D890,708 | S | 7/2020 | Forrest et al. |
| 10,721,785 | B2 | 7/2020 | Al-Ali |
| 10,736,518 | B2 | 8/2020 | Al-Ali et al. |
| 10,750,984 | B2 | 8/2020 | Pauley et al. |
| D897,098 | S | 9/2020 | Al-Ali |
| 10,779,098 | B2 | 9/2020 | Iswanto et al. |
| 10,827,961 | B1 | 11/2020 | Iyengar et al. |
| 10,828,007 | B1 | 11/2020 | Telfort et al. |
| 10,832,818 | B2 | 11/2020 | Muhsin et al. |
| 10,849,554 | B2 | 12/2020 | Shreim et al. |
| 10,856,750 | B2 | 12/2020 | Indorf et al. |
| D906,970 | S | 1/2021 | Forrest et al. |
| D908,213 | S | 1/2021 | Abdul-Hafiz et al. |
| 10,918,281 | B2 | 2/2021 | Al-Ali et al. |
| 10,932,705 | B2 | 3/2021 | Muhsin et al. |
| 10,932,729 | B2 | 3/2021 | Kiani et al. |
| 10,939,878 | B2 | 3/2021 | Kiani et al. |
| 10,956,950 | B2 | 3/2021 | Al-Ali et al. |
| D916,135 | S | 4/2021 | Indorf et al. |
| D917,046 | S | 4/2021 | Abdul-Hafiz et al. |
| D917,550 | S | 4/2021 | Indorf et al. |
| D917,564 | S | 4/2021 | Indorf et al. |
| D917,704 | S | 4/2021 | Al-Ali et al. |
| 10,987,066 | B2 | 4/2021 | Chandran et al. |
| 10,991,135 | B2 | 4/2021 | Al-Ali et al. |
| D919,094 | S | 5/2021 | Al-Ali et al. |
| D919,100 | S | 5/2021 | Al-Ali et al. |
| 11,006,867 | B2 | 5/2021 | Al-Ali |
| D921,202 | S | 6/2021 | Al-Ali et al. |
| 11,024,064 | B2 | 6/2021 | Muhsin et al. |
| 11,026,604 | B2 | 6/2021 | Chen et al. |
| D925,597 | S | 7/2021 | Chandran et al. |
| D927,699 | S | 8/2021 | Al-Ali et al. |
| 11,076,777 | B2 | 8/2021 | Lee et al. |
| 11,114,188 | B2 | 9/2021 | Poeze et al. |
| D933,232 | S | 10/2021 | Al-Ali et al. |
| D933,233 | S | 10/2021 | Al-Ali et al. |
| D933,234 | S | 10/2021 | Al-Ali et al. |
| 11,145,408 | B2 | 10/2021 | Sampath et al. |
| 11,147,518 | B1 | 10/2021 | Al-Ali et al. |
| 11,185,262 | B2 | 11/2021 | Al-Ali et al. |
| 11,191,484 | B2 | 12/2021 | Kiani et al. |
| D946,596 | S | 3/2022 | Ahmed |
| D946,597 | S | 3/2022 | Ahmed |
| D946,598 | S | 3/2022 | Ahmed |
| D946,617 | S | 3/2022 | Ahmed |
| 11,272,839 | B2 | 3/2022 | Al-Ali et al. |
| 11,289,199 | B2 | 3/2022 | Al-Ali |
| RE49,034 | E | 4/2022 | Al-Ali |
| 11,298,021 | B2 | 4/2022 | Muhsin et al. |
| D950,580 | S | 5/2022 | Ahmed |
| D950,599 | S | 5/2022 | Ahmed |
| D950,738 | S | 5/2022 | Al-Ali et al. |
| D957,648 | S | 7/2022 | Al-Ali |
| 11,382,567 | B2 | 7/2022 | O'Brien et al. |
| 11,389,093 | B2 | 7/2022 | Triman et al. |
| 11,406,286 | B2 | 8/2022 | Al-Ali et al. |
| 11,417,426 | B2 | 8/2022 | Muhsin et al. |
| 11,439,329 | B2 | 9/2022 | Lamego |
| 11,445,948 | B2 | 9/2022 | Scruggs et al. |
| D965,789 | S | 10/2022 | Al-Ali et al. |
| D967,433 | S | 10/2022 | Al-Ali et al. |
| 11,464,410 | B2 | 10/2022 | Muhsin |
| 11,504,058 | B1 | 11/2022 | Sharma et al. |
| 11,504,066 | B1 | 11/2022 | Dalvi et al. |
| D971,933 | S | 12/2022 | Ahmed |
| D973,072 | S | 12/2022 | Ahmed |
| D973,685 | S | 12/2022 | Ahmed |
| D973,686 | S | 12/2022 | Ahmed |
| D974,193 | S | 1/2023 | Forrest et al. |
| D979,516 | S | 2/2023 | Al-Ali et al. |
| D980,091 | S | 3/2023 | Forrest et al. |
| 11,596,363 | B2 | 3/2023 | Lamego |
| 11,627,919 | B2 | 4/2023 | Kiani et al. |
| 11,637,437 | B2 | 4/2023 | Al-Ali et al. |
| D985,498 | S | 5/2023 | Al-Ali et al. |
| 11,653,862 | B2 | 5/2023 | Dalvi et al. |
| D989,112 | S | 6/2023 | Muhsin et al. |
| D989,327 | S | 6/2023 | Al-Ali et al. |
| 11,678,829 | B2 | 6/2023 | Al-Ali et al. |

(56) References Cited

U.S. PATENT DOCUMENTS

| | | | |
|---|---|---|---|
| 11,679,579 | B2 | 6/2023 | Al-Ali |
| 11,684,296 | B2 | 6/2023 | Vo et al. |
| 11,692,934 | B2 | 7/2023 | Normand et al. |
| 11,701,043 | B2 | 7/2023 | Al-Ali et al. |
| D997,365 | S | 8/2023 | Hwang |
| 11,721,105 | B2 | 8/2023 | Ranasinghe et al. |
| 11,730,379 | B2 | 8/2023 | Ahmed et al. |
| D998,625 | S | 9/2023 | Indorf et al. |
| D998,630 | S | 9/2023 | Indorf et al. |
| D998,631 | S | 9/2023 | Indorf et al. |
| D999,244 | S | 9/2023 | Indorf et al. |
| D999,245 | S | 9/2023 | Indorf et al. |
| D999,246 | S | 9/2023 | Indorf et al. |
| 11,766,198 | B2 | 9/2023 | Pauley et al. |
| D1,000,975 | S | 10/2023 | Al-Ali et al. |
| 11,803,623 | B2 | 10/2023 | Kiani et al. |
| 11,832,940 | B2 | 12/2023 | Diab et al. |
| D1,013,179 | S | 1/2024 | Al-Ali et al. |
| 11,872,156 | B2 | 1/2024 | Telfort et al. |
| 11,879,960 | B2 | 1/2024 | Ranasinghe et al. |
| 11,883,129 | B2 | 1/2024 | Olsen |
| D1,022,729 | S | 4/2024 | Forrest et al. |
| 11,951,186 | B2 | 4/2024 | Krishnamani et al. |
| 11,974,833 | B2 | 5/2024 | Forrest et al. |
| 2001/0034477 | A1 | 10/2001 | Mansfield et al. |
| 2001/0039483 | A1 | 11/2001 | Brand et al. |
| 2002/0010401 | A1 | 1/2002 | Bushmakin et al. |
| 2002/0058864 | A1 | 5/2002 | Mansfield et al. |
| 2002/0133080 | A1 | 9/2002 | Apruzzese et al. |
| 2002/0193670 | A1 | 12/2002 | Garfield et al. |
| 2003/0013975 | A1 | 1/2003 | Kiani |
| 2003/0015368 | A1 | 1/2003 | Cybulski et al. |
| 2003/0018243 | A1 | 1/2003 | Gerhardt et al. |
| 2003/0135087 | A1 | 7/2003 | Hickle et al. |
| 2003/0144582 | A1 | 7/2003 | Cohen et al. |
| 2003/0149349 | A1 | 8/2003 | Jensen |
| 2003/0156288 | A1 | 8/2003 | Barnum et al. |
| 2003/0196660 | A1 | 10/2003 | Haveri |
| 2003/0212312 | A1 | 11/2003 | Coffin, IV et al. |
| 2004/0015093 | A1 | 1/2004 | Knapp, II et al. |
| 2004/0106163 | A1 | 6/2004 | Workman, Jr. et al. |
| 2004/0149282 | A1 | 8/2004 | Hickle |
| 2004/0158162 | A1 | 8/2004 | Narimatsu |
| 2004/0167416 | A1 | 8/2004 | Lee |
| 2004/0215094 | A1 | 10/2004 | Baumer et al. |
| 2004/0226771 | A1 | 11/2004 | Werblud |
| 2004/0228494 | A1 | 11/2004 | Smith |
| 2005/0033128 | A1 | 2/2005 | Ali et al. |
| 2005/0055276 | A1 | 3/2005 | Kiani et al. |
| 2005/0114455 | A1 | 5/2005 | Conroy et al. |
| 2005/0234317 | A1 | 10/2005 | Kiani |
| 2005/0272987 | A1 | 12/2005 | Kiani-Azarbayjany et al. |
| 2005/0283059 | A1 | 12/2005 | Vijay et al. |
| 2006/0047215 | A1 | 3/2006 | Newman et al. |
| 2006/0059324 | A1 | 3/2006 | Simske et al. |
| 2006/0073719 | A1 | 4/2006 | Kiani |
| 2006/0094943 | A1 | 5/2006 | Van Slyke |
| 2006/0144397 | A1 | 7/2006 | Wallace et al. |
| 2006/0155167 | A1 | 7/2006 | Elliott |
| 2006/0161054 | A1 | 7/2006 | Reuss et al. |
| 2006/0184052 | A1 | 8/2006 | Iwasawa |
| 2006/0189871 | A1 | 8/2006 | Al-Ali et al. |
| 2006/0190051 | A1 | 8/2006 | Gerber et al. |
| 2006/0198533 | A1 | 9/2006 | Wang |
| 2006/0238333 | A1 | 10/2006 | Welch et al. |
| 2006/0264767 | A1 | 11/2006 | Shennib |
| 2007/0016030 | A1 | 1/2007 | Stringer |
| 2007/0049837 | A1 | 3/2007 | Shertukde et al. |
| 2007/0056582 | A1 | 3/2007 | Wood et al. |
| 2007/0058818 | A1 | 3/2007 | Yoshimine |
| 2007/0073116 | A1 | 3/2007 | Kiani et al. |
| 2007/0106179 | A1 | 5/2007 | Bagha et al. |
| 2007/0118054 | A1 | 5/2007 | Pinhas |
| 2007/0135725 | A1 | 6/2007 | Hatlestad |
| 2007/0147639 | A1 | 6/2007 | Richardson et al. |
| 2007/0165872 | A1 | 7/2007 | Bridger et al. |
| 2007/0167855 | A1 | 7/2007 | Shin et al. |
| 2007/0173730 | A1 | 7/2007 | Bikko |
| 2007/0180140 | A1 | 8/2007 | Welch et al. |
| 2007/0185397 | A1 | 8/2007 | Govari et al. |
| 2007/0208262 | A1 | 9/2007 | Kovacs |
| 2007/0244377 | A1 | 10/2007 | Cozad et al. |
| 2007/0255153 | A1 | 11/2007 | Kumar et al. |
| 2007/0282174 | A1 | 12/2007 | Sabatino |
| 2007/0282212 | A1 | 12/2007 | Sierra et al. |
| 2007/0282478 | A1 | 12/2007 | Al-Ali et al. |
| 2008/0039735 | A1 | 2/2008 | Hickerson |
| 2008/0064965 | A1 | 3/2008 | Jay et al. |
| 2008/0076972 | A1 | 3/2008 | Dorogusker et al. |
| 2008/0077026 | A1 | 3/2008 | Banet et al. |
| 2008/0077198 | A1 | 3/2008 | Webb et al. |
| 2008/0077435 | A1 | 3/2008 | Muradia |
| 2008/0093157 | A1 | 4/2008 | Drummond et al. |
| 2008/0094228 | A1 | 4/2008 | Welch et al. |
| 2008/0097249 | A1 | 4/2008 | Pool et al. |
| 2008/0103375 | A1 | 5/2008 | Kiani |
| 2008/0114220 | A1 | 5/2008 | Banet et al. |
| 2008/0137876 | A1 | 6/2008 | Kassal et al. |
| 2008/0139953 | A1 | 6/2008 | Baker et al. |
| 2008/0143496 | A1 | 6/2008 | Linjama |
| 2008/0188760 | A1 | 8/2008 | Al-Ali et al. |
| 2008/0219464 | A1 | 9/2008 | Smith |
| 2008/0221418 | A1 | 9/2008 | Al-Ali et al. |
| 2008/0251313 | A1 | 10/2008 | Knight et al. |
| 2008/0281219 | A1 | 11/2008 | Glickman et al. |
| 2009/0018409 | A1 | 1/2009 | Banet et al. |
| 2009/0018429 | A1 | 1/2009 | Saliga et al. |
| 2009/0036759 | A1 | 2/2009 | Ault et al. |
| 2009/0076363 | A1 | 3/2009 | Bly et al. |
| 2009/0093687 | A1 | 4/2009 | Telfort et al. |
| 2009/0095926 | A1 | 4/2009 | MacNeish, III |
| 2009/0170664 | A1 | 7/2009 | Shirasaki et al. |
| 2009/0187065 | A1 | 7/2009 | Basinger |
| 2009/0247924 | A1 | 10/2009 | Lamego et al. |
| 2009/0247984 | A1 | 10/2009 | Lamego et al. |
| 2009/0275813 | A1 | 11/2009 | Davis |
| 2009/0275844 | A1 | 11/2009 | Al-Ali |
| 2009/0299157 | A1 | 12/2009 | Telfort et al. |
| 2009/0299742 | A1 | 12/2009 | Toman et al. |
| 2009/0316925 | A1 | 12/2009 | Eisenfeld et al. |
| 2010/0004518 | A1 | 1/2010 | Vo et al. |
| 2010/0030040 | A1 | 2/2010 | Poeze et al. |
| 2010/0090901 | A1 | 4/2010 | Smith et al. |
| 2010/0094096 | A1 | 4/2010 | Petruzzelli et al. |
| 2010/0099964 | A1 | 4/2010 | O'Reilly et al. |
| 2010/0195864 | A1 | 8/2010 | Lutz et al. |
| 2010/0204996 | A1 | 8/2010 | Zeng et al. |
| 2010/0234718 | A1 | 9/2010 | Sampath et al. |
| 2010/0256505 | A1 | 10/2010 | Xu |
| 2010/0270257 | A1 | 10/2010 | Wachman et al. |
| 2010/0274099 | A1 | 10/2010 | Telfort et al. |
| 2010/0305416 | A1 | 12/2010 | Bédard et al. |
| 2011/0028802 | A1 | 2/2011 | Addison |
| 2011/0028806 | A1 | 2/2011 | Merritt et al. |
| 2011/0028809 | A1 | 2/2011 | Goodman |
| 2011/0034831 | A1 | 2/2011 | Christensen et al. |
| 2011/0040197 | A1 | 2/2011 | Welch et al. |
| 2011/0066062 | A1 | 3/2011 | Banet et al. |
| 2011/0082711 | A1 | 4/2011 | Poeze et al. |
| 2011/0087081 | A1 | 4/2011 | Kiani et al. |
| 2011/0087083 | A1 | 4/2011 | Poeze et al. |
| 2011/0105854 | A1 | 5/2011 | Kiani et al. |
| 2011/0118561 | A1 | 5/2011 | Tari et al. |
| 2011/0125060 | A1 | 5/2011 | Telfort et al. |
| 2011/0137297 | A1 | 6/2011 | Kiani et al. |
| 2011/0172498 | A1 | 7/2011 | Olsen et al. |
| 2011/0172551 | A1 | 7/2011 | Al-Ali |
| 2011/0172561 | A1 | 7/2011 | Al-Ali et al. |
| 2011/0172967 | A1 | 7/2011 | Al-Ali et al. |
| 2011/0196211 | A1 | 8/2011 | Al-Ali et al. |
| 2011/0208015 | A1 | 8/2011 | Welch et al. |
| 2011/0209915 | A1 | 9/2011 | Fechter et al. |
| 2011/0213271 | A1 | 9/2011 | Telfort et al. |
| 2011/0213272 | A1 | 9/2011 | Telfort et al. |

(56) References Cited

U.S. PATENT DOCUMENTS

| | | | |
|---|---|---|---|
| 2011/0213273 | A1 | 9/2011 | Telfort et al. |
| 2011/0213274 | A1 | 9/2011 | Telfort et al. |
| 2011/0224567 | A1 | 9/2011 | Al-Ali |
| 2011/0230733 | A1 | 9/2011 | Al-Ali |
| 2011/0237969 | A1 | 9/2011 | Eckerbom et al. |
| 2011/0279963 | A1 | 11/2011 | Kumar et al. |
| 2011/0288383 | A1 | 11/2011 | Diab |
| 2011/0288431 | A1 | 11/2011 | Alshaer et al. |
| 2011/0301444 | A1 | 12/2011 | Al-Ali |
| 2012/0041316 | A1 | 2/2012 | Al Ali et al. |
| 2012/0046557 | A1 | 2/2012 | Kiani |
| 2012/0088984 | A1 | 4/2012 | Al-Ali et al. |
| 2012/0116175 | A1 | 5/2012 | Al-Ali et al. |
| 2012/0123231 | A1 | 5/2012 | O'Reilly |
| 2012/0165629 | A1 | 6/2012 | Merritt et al. |
| 2012/0209082 | A1 | 8/2012 | Al-Ali |
| 2012/0209084 | A1 | 8/2012 | Olsen et al. |
| 2012/0226117 | A1 | 9/2012 | Lamego et al. |
| 2012/0230523 | A1 | 9/2012 | Ehrlund |
| 2012/0232427 | A1 | 9/2012 | Bakema et al. |
| 2012/0265039 | A1 | 10/2012 | Kiani |
| 2012/0283524 | A1 | 11/2012 | Kiani et al. |
| 2012/0286955 | A1 | 11/2012 | Welch et al. |
| 2012/0302920 | A1 | 11/2012 | Bridger et al. |
| 2012/0319816 | A1 | 12/2012 | Al-Ali |
| 2013/0023775 | A1 | 1/2013 | Lamego et al. |
| 2013/0041591 | A1 | 2/2013 | Lamego |
| 2013/0060108 | A1 | 3/2013 | Schurman et al. |
| 2013/0060147 | A1 | 3/2013 | Welch et al. |
| 2013/0090567 | A1 | 4/2013 | Al-Ali et al. |
| 2013/0096405 | A1 | 4/2013 | Garfio |
| 2013/0096936 | A1 | 4/2013 | Sampath et al. |
| 2013/0116578 | A1 | 5/2013 | An et al. |
| 2013/0178749 | A1 | 7/2013 | Lamego |
| 2013/0243021 | A1 | 9/2013 | Siskavich |
| 2013/0253334 | A1 | 9/2013 | Al-Ali et al. |
| 2013/0262730 | A1 | 10/2013 | Al-Ali et al. |
| 2013/0267804 | A1 | 10/2013 | Al-Ali |
| 2013/0274572 | A1 | 10/2013 | Al-Ali et al. |
| 2013/0296672 | A1 | 11/2013 | O'Neil et al. |
| 2013/0296713 | A1 | 11/2013 | Al-Ali et al. |
| 2013/0317327 | A1 | 11/2013 | Al-Ali et al. |
| 2013/0324808 | A1 | 12/2013 | Al-Ali et al. |
| 2013/0324817 | A1 | 12/2013 | Diab |
| 2013/0331660 | A1 | 12/2013 | Al-Ali et al. |
| 2013/0345921 | A1 | 12/2013 | Al-Ali et al. |
| 2014/0012100 | A1 | 1/2014 | Al-Ali et al. |
| 2014/0051952 | A1 | 2/2014 | Reichgott et al. |
| 2014/0051953 | A1 | 2/2014 | Lamego et al. |
| 2014/0081175 | A1 | 3/2014 | Telfort |
| 2014/0120564 | A1 | 5/2014 | Workman et al. |
| 2014/0121482 | A1 | 5/2014 | Merritt et al. |
| 2014/0127137 | A1 | 5/2014 | Bellott et al. |
| 2014/0128699 | A1 | 5/2014 | Al-Ali et al. |
| 2014/0135588 | A1 | 5/2014 | Al-Ali et al. |
| 2014/0142399 | A1 | 5/2014 | Al-Ali et al. |
| 2014/0142402 | A1 | 5/2014 | Al-Ali et al. |
| 2014/0163344 | A1 | 6/2014 | Al-Ali |
| 2014/0163402 | A1 | 6/2014 | Lamego et al. |
| 2014/0166076 | A1 | 6/2014 | Kiani et al. |
| 2014/0171763 | A1 | 6/2014 | Diab |
| 2014/0180038 | A1 | 6/2014 | Kiani |
| 2014/0180154 | A1 | 6/2014 | Sierra et al. |
| 2014/0180160 | A1 | 6/2014 | Brown et al. |
| 2014/0187973 | A1 | 7/2014 | Brown et al. |
| 2014/0200422 | A1 | 7/2014 | Weber et al. |
| 2014/0213864 | A1 | 7/2014 | Abdul-Hafiz et al. |
| 2014/0266790 | A1 | 9/2014 | Al-Ali et al. |
| 2014/0275808 | A1 | 9/2014 | Poeze et al. |
| 2014/0275835 | A1 | 9/2014 | Lamego et al. |
| 2014/0275871 | A1 | 9/2014 | Lamego et al. |
| 2014/0275872 | A1 | 9/2014 | Merritt et al. |
| 2014/0276115 | A1 | 9/2014 | Dalvi et al. |
| 2014/0288400 | A1 | 9/2014 | Diab et al. |
| 2014/0316217 | A1 | 10/2014 | Purdon et al. |
| 2014/0316218 | A1 | 10/2014 | Purdon et al. |
| 2014/0316228 | A1 | 10/2014 | Blank et al. |
| 2014/0323825 | A1 | 10/2014 | Al-Ali et al. |
| 2014/0323897 | A1 | 10/2014 | Brown et al. |
| 2014/0323898 | A1 | 10/2014 | Purdon et al. |
| 2014/0330092 | A1 | 11/2014 | Al-Ali et al. |
| 2014/0330098 | A1 | 11/2014 | Merritt et al. |
| 2014/0333440 | A1 | 11/2014 | Kiani |
| 2014/0357966 | A1 | 12/2014 | Al-Ali et al. |
| 2014/0371548 | A1 | 12/2014 | Al-Ali et al. |
| 2014/0378784 | A1 | 12/2014 | Kiani et al. |
| 2015/0005600 | A1 | 1/2015 | Blank et al. |
| 2015/0011907 | A1 | 1/2015 | Purdon et al. |
| 2015/0012231 | A1 | 1/2015 | Poeze et al. |
| 2015/0018650 | A1 | 1/2015 | Al-Ali et al. |
| 2015/0032029 | A1 | 1/2015 | Al-Ali et al. |
| 2015/0038859 | A1 | 2/2015 | Dalvi et al. |
| 2015/0045637 | A1 | 2/2015 | Dalvi |
| 2015/0045685 | A1 | 2/2015 | Al-Ali et al. |
| 2015/0051462 | A1 | 2/2015 | Olsen |
| 2015/0073241 | A1 | 3/2015 | Lamego |
| 2015/0080754 | A1 | 3/2015 | Purdon et al. |
| 2015/0087936 | A1 | 3/2015 | Al-Ali et al. |
| 2015/0094546 | A1 | 4/2015 | Ai-Ali |
| 2015/0097701 | A1 | 4/2015 | Muhsin et al. |
| 2015/0099950 | A1 | 4/2015 | Al-Ali et al. |
| 2015/0099951 | A1 | 4/2015 | Al-Ali et al. |
| 2015/0099955 | A1 | 4/2015 | Al-Ali et al. |
| 2015/0099998 | A1 | 4/2015 | Christensen et al. |
| 2015/0101844 | A1 | 4/2015 | Al-Ali et al. |
| 2015/0106121 | A1 | 4/2015 | Muhsin et al. |
| 2015/0112151 | A1 | 4/2015 | Muhsin et al. |
| 2015/0116076 | A1 | 4/2015 | Al-Ali et al. |
| 2015/0126830 | A1 | 5/2015 | Schurman et al. |
| 2015/0133755 | A1 | 5/2015 | Smith et al. |
| 2015/0140863 | A1 | 5/2015 | Al-Ali et al. |
| 2015/0141781 | A1 | 5/2015 | Weber et al. |
| 2015/0165312 | A1 | 6/2015 | Kiani |
| 2015/0196237 | A1 | 7/2015 | Lamego |
| 2015/0196249 | A1 | 7/2015 | Brown et al. |
| 2015/0201874 | A1 | 7/2015 | Diab |
| 2015/0208966 | A1 | 7/2015 | Al-Ali |
| 2015/0216459 | A1 | 8/2015 | Al-Ali et al. |
| 2015/0230755 | A1 | 8/2015 | Al-Ali et al. |
| 2015/0238722 | A1 | 8/2015 | Ai-Ali |
| 2015/0245773 | A1 | 9/2015 | Lamego et al. |
| 2015/0245794 | A1 | 9/2015 | Al-Ali |
| 2015/0257689 | A1 | 9/2015 | Al-Ali et al. |
| 2015/0272514 | A1 | 10/2015 | Kiani et al. |
| 2015/0351697 | A1 | 12/2015 | Weber et al. |
| 2015/0351704 | A1 | 12/2015 | Kiani et al. |
| 2015/0359429 | A1 | 12/2015 | Al-Ali et al. |
| 2015/0366472 | A1 | 12/2015 | Kiani |
| 2015/0366507 | A1 | 12/2015 | Blank et al. |
| 2015/0374298 | A1 | 12/2015 | Al-Ali et al. |
| 2015/0380875 | A1 | 12/2015 | Coverston et al. |
| 2016/0000362 | A1 | 1/2016 | Diab et al. |
| 2016/0007930 | A1 | 1/2016 | Weber et al. |
| 2016/0029932 | A1 | 2/2016 | Al-Ali |
| 2016/0029933 | A1 | 2/2016 | Al-Ali et al. |
| 2016/0045118 | A1 | 2/2016 | Kiani |
| 2016/0051205 | A1 | 2/2016 | Al-Ali et al. |
| 2016/0058338 | A1 | 3/2016 | Schurman et al. |
| 2016/0058347 | A1 | 3/2016 | Reichgott et al. |
| 2016/0066823 | A1 | 3/2016 | Al-Ali et al. |
| 2016/0066824 | A1 | 3/2016 | Al-Ali et al. |
| 2016/0066879 | A1 | 3/2016 | Telfort et al. |
| 2016/0072429 | A1 | 3/2016 | Kiani et al. |
| 2016/0073967 | A1 | 3/2016 | Lamego et al. |
| 2016/0081552 | A1 | 3/2016 | Wojtczuk et al. |
| 2016/0095543 | A1 | 4/2016 | Telfort et al. |
| 2016/0095548 | A1 | 4/2016 | Al-Ali et al. |
| 2016/0103598 | A1 | 4/2016 | Al-Ali et al. |
| 2016/0113527 | A1 | 4/2016 | Ai-Ali |
| 2016/0143548 | A1 | 5/2016 | Al-Ali |
| 2016/0166182 | A1 | 6/2016 | Al-Ali et al. |
| 2016/0166183 | A1 | 6/2016 | Poeze et al. |
| 2016/0166188 | A1 | 6/2016 | Bruinsma et al. |
| 2016/0166210 | A1 | 6/2016 | Ai-Ali |

(56) References Cited

U.S. PATENT DOCUMENTS

| | | | |
|---|---|---|---|
| 2016/0192869 | A1 | 7/2016 | Kiani et al. |
| 2016/0196388 | A1 | 7/2016 | Lamego |
| 2016/0197436 | A1 | 7/2016 | Barker et al. |
| 2016/0213281 | A1 | 7/2016 | Eckerbom et al. |
| 2016/0228043 | A1 | 8/2016 | O'Neil et al. |
| 2016/0233632 | A1 | 8/2016 | Scruggs et al. |
| 2016/0234944 | A1 | 8/2016 | Schmidt et al. |
| 2016/0270735 | A1 | 9/2016 | Diab et al. |
| 2016/0283665 | A1 | 9/2016 | Sampath et al. |
| 2016/0287090 | A1 | 10/2016 | Al-Ali et al. |
| 2016/0287786 | A1 | 10/2016 | Kiani |
| 2016/0296169 | A1 | 10/2016 | McHale et al. |
| 2016/0310052 | A1 | 10/2016 | Al-Ali et al. |
| 2016/0314260 | A1 | 10/2016 | Kiani |
| 2016/0324486 | A1 | 11/2016 | Al-Ali et al. |
| 2016/0324488 | A1 | 11/2016 | Olsen |
| 2016/0327984 | A1 | 11/2016 | Al-Ali et al. |
| 2016/0328528 | A1 | 11/2016 | Al-Ali et al. |
| 2016/0331332 | A1 | 11/2016 | Al-Ali |
| 2016/0367173 | A1 | 12/2016 | Dalvi et al. |
| 2017/0000394 | A1 | 1/2017 | Al-Ali et al. |
| 2017/0007134 | A1 | 1/2017 | Al-Ali et al. |
| 2017/0007198 | A1 | 1/2017 | Al-Ali et al. |
| 2017/0014083 | A1 | 1/2017 | Diab et al. |
| 2017/0014084 | A1 | 1/2017 | Al-Ali et al. |
| 2017/0024748 | A1 | 1/2017 | Haider |
| 2017/0027456 | A1 | 2/2017 | Kinast et al. |
| 2017/0042488 | A1 | 2/2017 | Muhsin |
| 2017/0055851 | A1 | 3/2017 | Al-Ali |
| 2017/0055882 | A1 | 3/2017 | Al-Ali et al. |
| 2017/0055887 | A1 | 3/2017 | Al-Ali |
| 2017/0055896 | A1 | 3/2017 | Ai-Ali |
| 2017/0079594 | A1 | 3/2017 | Telfort et al. |
| 2017/0086723 | A1 | 3/2017 | Al-Ali et al. |
| 2017/0143281 | A1 | 5/2017 | Olsen |
| 2017/0147774 | A1 | 5/2017 | Kiani |
| 2017/0156620 | A1 | 6/2017 | Al-Ali et al. |
| 2017/0173632 | A1 | 6/2017 | Al-Ali |
| 2017/0187146 | A1 | 6/2017 | Kiani et al. |
| 2017/0188919 | A1 | 7/2017 | Al-Ali et al. |
| 2017/0196464 | A1 | 7/2017 | Jansen et al. |
| 2017/0196470 | A1 | 7/2017 | Lamego et al. |
| 2017/0202490 | A1 | 7/2017 | Al-Ali et al. |
| 2017/0224262 | A1 | 8/2017 | Al-Ali |
| 2017/0228516 | A1 | 8/2017 | Sampath et al. |
| 2017/0245790 | A1 | 8/2017 | Al-Ali et al. |
| 2017/0251974 | A1 | 9/2017 | Shreim et al. |
| 2017/0251975 | A1 | 9/2017 | Shreim et al. |
| 2017/0258403 | A1 | 9/2017 | Abdul-Hafiz et al. |
| 2017/0311891 | A1 | 11/2017 | Kiani et al. |
| 2017/0325728 | A1 | 11/2017 | Al-Ali et al. |
| 2017/0332976 | A1 | 11/2017 | Al-Ali |
| 2017/0340293 | A1 | 11/2017 | Al-Ali et al. |
| 2017/0360310 | A1 | 12/2017 | Kiani |
| 2017/0367632 | A1 | 12/2017 | Al-Ali et al. |
| 2018/0008146 | A1 | 1/2018 | Al-Ali et al. |
| 2018/0014752 | A1 | 1/2018 | Al-Ali et al. |
| 2018/0028124 | A1 | 2/2018 | Al-Ali et al. |
| 2018/0055385 | A1 | 3/2018 | Al-Ali |
| 2018/0055390 | A1 | 3/2018 | Kiani et al. |
| 2018/0055430 | A1 | 3/2018 | Diab et al. |
| 2018/0064381 | A1 | 3/2018 | Shakespeare et al. |
| 2018/0069776 | A1 | 3/2018 | Lamego et al. |
| 2018/0103874 | A1 | 4/2018 | Lee et al. |
| 2018/0242926 | A1 | 8/2018 | Muhsin et al. |
| 2018/0247353 | A1 | 8/2018 | Al-Ali et al. |
| 2018/0247712 | A1 | 8/2018 | Muhsin et al. |
| 2018/0256087 | A1 | 9/2018 | Al-Ali et al. |
| 2018/0296161 | A1 | 10/2018 | Shreim et al. |
| 2018/0300919 | A1 | 10/2018 | Muhsin et al. |
| 2018/0310822 | A1 | 11/2018 | Indorf et al. |
| 2018/0310823 | A1 | 11/2018 | Al-Ali et al. |
| 2018/0317826 | A1 | 11/2018 | Muhsin et al. |
| 2019/0015023 | A1 | 1/2019 | Monfre |
| 2019/0117070 | A1 | 4/2019 | Muhsin et al. |

| | | | |
|---|---|---|---|
| 2019/0200941 | A1 | 7/2019 | Chandran et al. |
| 2019/0239787 | A1 | 8/2019 | Pauley et al. |
| 2019/0320906 | A1 | 10/2019 | Olsen |
| 2019/0374139 | A1 | 12/2019 | Kiani et al. |
| 2019/0374173 | A1 | 12/2019 | Kiani et al. |
| 2019/0374713 | A1 | 12/2019 | Kiani et al. |
| 2020/0060869 | A1 | 2/2020 | Telfort et al. |
| 2020/0111552 | A1 | 4/2020 | Ahmed |
| 2020/0113435 | A1 | 4/2020 | Muhsin |
| 2020/0113488 | A1 | 4/2020 | Al-Ali et al. |
| 2020/0113496 | A1 | 4/2020 | Scruggs et al. |
| 2020/0113497 | A1 | 4/2020 | Triman et al. |
| 2020/0113520 | A1 | 4/2020 | Abdul-Hafiz et al. |
| 2020/0138288 | A1 | 5/2020 | Al-Ali et al. |
| 2020/0138368 | A1 | 5/2020 | Kiani et al. |
| 2020/0163597 | A1 | 5/2020 | Dalvi et al. |
| 2020/0196877 | A1 | 6/2020 | Vo et al. |
| 2020/0253474 | A1 | 8/2020 | Muhsin et al. |
| 2020/0253544 | A1 | 8/2020 | Belur Nagaraj et al. |
| 2020/0275841 | A1 | 9/2020 | Telfort et al. |
| 2020/0288983 | A1 | 9/2020 | Telfort et al. |
| 2020/0321793 | A1 | 10/2020 | Al-Ali et al. |
| 2020/0329983 | A1 | 10/2020 | Al-Ali et al. |
| 2020/0329984 | A1 | 10/2020 | Al-Ali et al. |
| 2020/0329993 | A1 | 10/2020 | Al-Ali et al. |
| 2020/0330037 | A1 | 10/2020 | Al-Ali et al. |
| 2021/0022628 | A1 | 1/2021 | Telfort et al. |
| 2021/0104173 | A1 | 4/2021 | Pauley et al. |
| 2021/0113121 | A1 | 4/2021 | Diab et al. |
| 2021/0117525 | A1 | 4/2021 | Kiani et al. |
| 2021/0118581 | A1 | 4/2021 | Kiani et al. |
| 2021/0121582 | A1 | 4/2021 | Krishnamani et al. |
| 2021/0161465 | A1 | 6/2021 | Barker et al. |
| 2021/0236729 | A1 | 8/2021 | Kiani et al. |
| 2021/0244378 | A1 | 8/2021 | Telfort |
| 2021/0256835 | A1 | 8/2021 | Ranasinghe et al. |
| 2021/0275101 | A1 | 9/2021 | Vo et al. |
| 2021/0290060 | A1 | 9/2021 | Ahmed |
| 2021/0290072 | A1 | 9/2021 | Forrest |
| 2021/0290080 | A1 | 9/2021 | Ahmed |
| 2021/0290120 | A1 | 9/2021 | Al-Ali |
| 2021/0290177 | A1 | 9/2021 | Novak, Jr. |
| 2021/0290184 | A1 | 9/2021 | Ahmed |
| 2021/0296008 | A1 | 9/2021 | Novak, Jr. |
| 2021/0330228 | A1 | 10/2021 | Olsen et al. |
| 2021/0386382 | A1 | 12/2021 | Olsen et al. |
| 2021/0402110 | A1 | 12/2021 | Pauley et al. |
| 2022/0039707 | A1 | 2/2022 | Sharma et al. |
| 2022/0053892 | A1 | 2/2022 | Al-Ali et al. |
| 2022/0071562 | A1 | 3/2022 | Kiani |
| 2022/0096603 | A1 | 3/2022 | Kiani et al. |
| 2022/0151521 | A1 | 5/2022 | Krishnamani et al. |
| 2022/0218244 | A1 | 7/2022 | Kiani et al. |
| 2022/0287574 | A1 | 9/2022 | Telfort et al. |
| 2022/0296161 | A1 | 9/2022 | Al-Ali et al. |
| 2022/0361819 | A1 | 11/2022 | Al-Ali et al. |
| 2022/0379059 | A1 | 12/2022 | Yu et al. |
| 2022/0392610 | A1 | 12/2022 | Kiani et al. |
| 2023/0028745 | A1 | 1/2023 | Al-Ali |
| 2023/0038389 | A1 | 2/2023 | Vo |
| 2023/0045647 | A1 | 2/2023 | Vo |
| 2023/0058052 | A1 | 2/2023 | Al-Ali |
| 2023/0058342 | A1 | 2/2023 | Kiani |
| 2023/0069789 | A1 | 3/2023 | Koo et al. |
| 2023/0087671 | A1 | 3/2023 | Telfort et al. |
| 2023/0110152 | A1 | 4/2023 | Forrest et al. |
| 2023/0111198 | A1 | 4/2023 | Yu et al. |
| 2023/0115397 | A1 | 4/2023 | Vo et al. |
| 2023/0116371 | A1 | 4/2023 | Mills et al. |
| 2023/0135297 | A1 | 5/2023 | Kiani et al. |
| 2023/0138098 | A1 | 5/2023 | Telfort et al. |
| 2023/0145155 | A1 | 5/2023 | Krishnamani et al. |
| 2023/0147750 | A1 | 5/2023 | Barker et al. |
| 2023/0210417 | A1 | 7/2023 | Al-Ali et al. |
| 2023/0222805 | A1 | 7/2023 | Muhsin et al. |
| 2023/0222887 | A1 | 7/2023 | Muhsin et al. |
| 2023/0226331 | A1 | 7/2023 | Kiani et al. |
| 2023/0284916 | A1 | 9/2023 | Telfort |
| 2023/0284943 | A1 | 9/2023 | Scruggs et al. |

(56) References Cited

U.S. PATENT DOCUMENTS

| | | | |
|---|---|---|---|
| 2023/0301562 | A1 | 9/2023 | Scruggs et al. |
| 2023/0346993 | A1 | 11/2023 | Kiani et al. |
| 2023/0368221 | A1 | 11/2023 | Haider |
| 2023/0371893 | A1 | 11/2023 | Al-Ali et al. |
| 2023/0389837 | A1 | 12/2023 | Krishnamani et al. |
| 2024/0016418 | A1 | 1/2024 | Devadoss et al. |
| 2024/0016419 | A1 | 1/2024 | Devadoss et al. |
| 2024/0047061 | A1 | 2/2024 | Al-Ali et al. |
| 2024/0049310 | A1 | 2/2024 | Al-Ali et al. |
| 2024/0049986 | A1 | 2/2024 | Al-Ali et al. |
| 2024/0081656 | A1 | 3/2024 | DeJong et al. |
| 2024/0122486 | A1 | 4/2024 | Kiani |

FOREIGN PATENT DOCUMENTS

| | | |
|---|---|---|
| CN | 201497610 | 6/2010 |
| CN | 202005761 | 10/2011 |
| EP | 0 716 628 | 12/1998 |
| EP | 0 659 058 | 1/1999 |
| EP | 0 956 820 | 11/1999 |
| EP | 1 518 442 | 3/2005 |
| EP | 2 014 234 | 1/2009 |
| EP | 1 207 536 | 2/2010 |
| EP | 2 488 106 | 8/2012 |
| EP | 2 488 978 | 8/2012 |
| FR | 2 847 796 | 6/2004 |
| GB | 2 358 546 | 7/2001 |
| JP | S53-094482 | 8/1978 |
| JP | S56-031742 | 3/1981 |
| JP | 60-059900 | 4/1985 |
| JP | 62-014898 | 1/1987 |
| JP | 01-309872 | 12/1989 |
| JP | H04-317637 | 11/1992 |
| JP | H07-152553 | 6/1995 |
| JP | 10-155755 | 6/1998 |
| JP | 2001-50713 | 2/2001 |
| JP | 2003-329719 | 11/2003 |
| JP | 2005-522292 | 7/2005 |
| JP | 2005-531230 | 10/2005 |
| JP | 2012-513872 | 6/2012 |
| JP | 2013-508029 | 3/2013 |
| JP | 2013-508030 | 3/2013 |
| NO | 20040819 | 2/2004 |
| WO | WO 94/005207 | 3/1994 |
| WO | WO 94/013207 | 6/1994 |
| WO | WO 95/029632 | 11/1995 |
| WO | WO 99/053277 | 10/1999 |
| WO | WO 00/010462 | 3/2000 |
| WO | WO 01/034033 | 5/2001 |
| WO | WO 01/087005 | 11/2001 |
| WO | WO 01/097691 | 12/2001 |
| WO | WO 02/003042 | 1/2002 |
| WO | WO 01/078059 | 3/2002 |
| WO | WO 02/024067 | 7/2002 |
| WO | WO 03/058646 | 7/2003 |
| WO | WO 03/087737 | 10/2003 |
| WO | WO 2004/000111 | 12/2003 |
| WO | WO 2004/004411 | 1/2004 |
| WO | WO 2004/078038 | 9/2004 |
| WO | WO 2005/096931 | 10/2005 |
| WO | WO 2005/099562 | 10/2005 |
| WO | WO 2008/017246 | 2/2008 |
| WO | WO 2008/148172 | 12/2008 |
| WO | WO 2009/137524 | 11/2009 |
| WO | WO 2009/155593 | 12/2009 |
| WO | WO 2010/078168 | 7/2010 |
| WO | WO 2011/047211 | 4/2011 |
| WO | WO 2011/047213 | 4/2011 |
| WO | WO 2011/047216 | 8/2011 |
| WO | WO 2011/047207 | 9/2011 |
| WO | WO 2011/047209 | 3/2012 |
| WO | WO 2013/056141 | 4/2013 |

OTHER PUBLICATIONS

US 2024/0016391 A1, 01/2024, Lapotko et al. (withdrawn)
Analog Devices, "12-Bit Serial Input Multiplying D/A Converter", DAC8043A, Product Data Sheet, Analog Devices, Inc., 2000, pp. 8.
Avago Technologies, "HCNR200 and HCNR201, High-Linearity Analog Optocouplers", Data Sheet, Avago Technologies, Nov. 18, 2008, pp. 19.
Eldor et al., "A device for monitoring ventilation during anesthesia; the paratracheal audible respiratory monitor", Canadian Journal of Anesthesia, 1990, vol. 9, No. 1, p. 95-98.
Office Action for EP Application No. 10779086.7 dated Mar. 5, 2013.
EP Office Action dated May 18, 2011 in application No. 03711767.8.
European Search Report for Application No. 13185148.7 dated Dec. 6, 2013.
International Preliminary Report on Patentability (IPRP) in PCT/US2010/052754, dated Apr. 26, 2012.
International Preliminary Report on Patentability dated Apr. 15, 2014 for PCT Application No. PCT/US2012/060084.
International Preliminary Report on Patentability in PCT/US2010/052763 dated Apr. 17, 2012 in 9 pages.
International Search Report & Written Opinion for PCT/US2010/052756, mailed Feb. 6, 2012; 17 pages.
International Search Report & Written Opinion, PCT Application PCT/US2010/052758, Feb. 10, 2011; 12 pages.
International Search Report & Written Opinion, PCT Application PCT/US2010/058981, Feb. 17, 2011; 11 pages.
International Search Report and Written Opinion dated Dec. 21, 2012 for PCT Application No. PCT/US2012/060084.
International Search Report and Written Opinion for PCT/US2009/042902, mailed Dec. 8, 2009.
International Search Report and Written Opinion in PCT/US2010/052754 mailed Jul. 27, 2011.
International Search Report and Written Opinion in PCT/US2010/052763, mailed May 13, 2011.
International Search Report and Written Opinion received in PCT Application No. PCT/US2010/052760 as mailed Mar. 8, 2011 in 11 pages.
International Search Report and Written Opinion issued in PCT Application No. PCT/US2009/069287, Jun. 30, 2010.
International Search Report, PCT Application PCT/CA2003/000536, Dec. 11, 2003; 2 pages.
Japanese Office Action re Application No. 2007-506626, dated Mar. 1, 2011.
Office Action in Japanese Application No. 2011-544508 mailed Apr. 30, 2014.
PCT Invitation to Pay Fees and Initial Search Report in PCT/US2009/069287, dated Apr. 21, 2010.
PCT Invitation to Pay Fees and Initial Search Report in PCT/US2010/052754, dated Mar. 15, 2011.
PCT Invitation to Pay Fees and Initial Search Report in PCT/US2010/052756, dated Oct. 5, 2011.
Sierra et al., "Monitoring Respiratory Rate based on Tracheal Sounds. First Experiences", Proceedings of the 26the Annual International Conference of the IEEE EMBS, Sep. 1-5, 2004, pp. 317-320.
WelchAllyn "ECG ASIC, ECG 3-lead, 5-lead, 12-lead and RESP Signal Processing, ECG ASIC Part No. 000.91163", May 2001, pp. 84.
White, "Advanced Compression Techniques, Tips & Tricks", Part 1 and Part 2, Dec. 2000 and Jan. 2001 in 7 pages.
Office Action for EP Application No. 10779086.7 dated Jul. 11, 2016.
Office Action for European Patent Application No. 13185148.7 dated Apr. 4, 2017.
Oversampling by Wikipedia, the free encyclopedia, pub. Online Oct. 7, 2012 at "https://wikipedia.org/w/index.php?title=Oversampling&oldid=516454012", accessed Sep. 3, 2015.
Pseudorandom noise by Wikipedia, the free encyclopedia, pub. Online Jul. 25, 2012 at "https://wikipedia.org/w/index.php?title=Pseudorandom_noise&oldid=504121479", accessed Sep. 3, 2015.

(56) References Cited

OTHER PUBLICATIONS

Noise generator by Wikipedia, the free encyclopedia, pub. Online May 6, 2012 at "https://wikipedia.org/w/index.php?title=Noise_generator&oldid=490897729", accessed Sep. 3, 2015.
Office Action for EP Application No. 10779086.7 dated May 12, 2017.
Office Action for EP Application No. 13185148.7 dated Nov. 7, 2017.
EP Office Action dated Oct. 16, 2018 in application No. 10773191.1.
Office Action for EP Application No. 10779086.7 dated Dec. 10, 2018.
Office Action in European Application No. 12784142.7 dated Apr. 10, 2018 in 5 pages.
Office Action for Application No. 13185148.7 dated Jun. 7, 2018.
Office Action in European Application No. 13185148.7 dated Apr. 4, 2019.
Office Action in European Application No. 20191376.1 dated Dec. 18, 2020 in 7 pages.
Office Action in European Application No. 19182152.9 dated Nov. 4, 2019 in 10 pages.
Office Action in European Application No. 20175965.1 dated Oct. 12, 2020 in 7 pages.
GE Healthcare, "Transport ProTM Patient Monitor" Operator's Manual, Software Version 2.1, Apr. 9, 2007, 286 pages.

ACOUSTIC PATIENT SENSOR COUPLER

RELATED APPLICATIONS

This application is a continuation of U.S. application Ser. No. 17/241,705, filed Apr. 27, 2021, titled "Acoustic Patient Sensor Coupler," which application is a continuation of U.S. application Ser. No. 15/926,555, filed Mar. 20, 2018, titled "Acoustic Patient Sensor Coupler," which application is a continuation of U.S. application Ser. No. 14/030,268, filed Sep. 18, 2013, titled "Acoustic Patient Sensor Coupler," which application is a nonprovisional of U.S. Provisional Application No. 61/703,731, filed Sep. 20, 2012, titled "Acoustic Patient Sensor Coupler", the disclosure of which is hereby incorporated by reference in its entirety. In addition, this application relates to the following U.S. patent applications, the disclosures of which are incorporated in their entirety by reference herein:

| application Ser. No. | Filing Date | Title |
|---|---|---|
| 12/044883 | Mar. 7, 2008 | Systems And Methods For Determining A Physiological Condition Using An Acoustic Monitor |
| 12/904836 | Oct. 14, 2010 | Bidirectional Physiological Information Display |
| 12/904823 | Oct. 14, 2010 | Bidirectional Physiological Information Display |
| 12/643939 | Dec. 21, 2009 | Acoustic Sensor Assembly |
| 12/904931 | Oct. 14, 2010 | Acoustic Respiratory Monitoring Sensor Having Multiple Sensing Elements |
| 12/904890 | Oct. 14, 2010 | Acoustic Respiratory Monitoring Sensor Having Multiple Sensing Elements |
| 12/904938 | Oct. 14, 2010 | Acoustic Respiratory Monitoring Sensor Having Multiple Sensing Elements |
| 12/904907 | Oct. 14, 2010 | Acoustic Patient Sensor |
| 12/904789 | Oct. 14, 2010 | Acoustic Respiratory Monitoring Systems and Methods |
| 12/904775 | Oct. 14, 2010 | Pulse Oximetry System With Low Noise Cable Hub |
| 13/554908 | Jul. 20, 2012 | Acoustic Respiratory Monitoring Sensor With Suspended Sensing Unit |
| 12/905036 | Oct. 14, 2010 | Physiological Acoustic Monitoring System |
| 61/547007 | Oct. 13, 2011 | Physiological Acoustic Monitoring System |
| 13/099263 | May 2, 2011 | Reflective Non-Invasive Sensor |

Many of the embodiments described herein are compatible with embodiments described in the above related applications. Moreover, some or all of the features described herein can be used or otherwise combined with many of the features described in the applications listed above.

BACKGROUND

The "piezoelectric effect" is the appearance of an electric potential and current across certain faces of a crystal when it is subjected to mechanical stresses. Due to their capacity to convert mechanical deformation into an electric voltage, piezoelectric crystals have been broadly used in devices such as transducers, strain gauges and microphones. However, before the crystals can be used in many of these applications they must be rendered into a form which suits the requirements of the application. In many applications, especially those involving the conversion of acoustic waves into a corresponding electric signal, piezoelectric membranes have been used.

Piezoelectric membranes are typically manufactured from polyvinylidene fluoride plastic film. The film is endowed with piezoelectric properties by stretching the plastic while it is placed under a high-poling voltage. By stretching the film, the film is polarized and the molecular structure of the plastic aligned. A thin layer of conductive metal (typically nickel-copper) is deposited on each side of the film to form electrode coatings to which connectors can be attached.

Piezoelectric membranes have a number of attributes that make them interesting for use in sound detection, including: a wide frequency range of between 0.001 Hz to 1 GHz; a low acoustical impedance close to water and human tissue; a high dielectric strength; a good mechanical strength; and piezoelectric membranes are moisture resistant and inert to many chemicals.

Due in large part to the above attributes, piezoelectric membranes are particularly suited for the capture of acoustic waves and the conversion thereof into electric signals and, accordingly, have found application in the detection of body sounds. However, there is still a need for reliable acoustic respiratory monitoring systems.

SUMMARY

Embodiments of an acoustic sensor and physiological monitoring system described herein are configured to provide accurate and robust measurement of bodily sounds under a variety of conditions, such as in noisy environments or in situations in which stress, strain, or movement can be imparted onto the sensor with respect to a patient.

According an aspect of the disclosure, an acoustic sensor includes one or more sensing elements supported by a frame or other support structure. The sensing elements contact the frame at certain locations and are spaced from the frame at others. The sensing elements and frame define a cavity in which the sensing elements vibrate in response to acoustic signals received from a medical patient. However, skin elasticity and the force used to attach the acoustic sensor to the medical patient's skin can affect the volume and/or air pressure within the cavity defined by the sensing elements and frame. Variability in skin elasticity or attachment force can lead to variability in cavity resonance, which can cause unwanted variability in sensor performance. For example, an acoustic sensor that is attached to very elastic skin may provide a different output signal than an acoustic sensor that is attached to firmer or tighter skin. Similarly, an acoustic sensor loosely attached to patient's skin may provide a different output signal than an acoustic sensor tightly attached a patient's skin.

To compensate for skin elasticity and attachment variability, in one embodiment the acoustic sensor support includes one or more pressure equalization pathways. The pathways provide an air-flow channel from the cavity defined by the sensing elements and frame to the ambient air pressure. By equalizing pressure within the cavity with ambient during sensing, variability in sensor performance may be reduced and/or eliminated. In some embodiments, the pressure equalization pathways include one or more holes, notches, ports, or channels that extend from within the sensor's cavity to a location in communication with ambient air pressure.

While certain embodiments described herein are compatible with single-sensing element designs, according to certain aspects, multiple acoustic sensing elements are employed to provide enhanced physiological monitoring. For example, multiple acoustic sensing elements can be included in one or more sensor packages coupled to a patient and/or at various other locations in the monitoring environment, such as on one or more sensor packages or other components not coupled to the patient.

In some configurations, a plurality of acoustic sensing elements are advantageously arranged in a single acoustic sensor package. In some such embodiments, physical and/or electrical symmetry between the sensing elements can be exploited. In some cases, for example, the electrical poles of two or more sensing elements are connected so as to provide improved electrical shielding, enhanced signal to noise ratio, reduced design complexity and associated cost. In one such configuration, multiple sensing elements are arranged in stack on a sensor frame or other support structure. Generally, shielding can be beneficially achieved using one or more portions that are integral to the sensing elements rather than using physically separate components.

Systems and methods described herein achieve noise compensation in a variety of ways. For example, sensing elements (or groups thereof) can be arranged such that a physiological signal sensing element provides a physiological signal having both a component indicative of a target physiological signal (e.g., respiratory, heart or digestive sounds) and an interfering noise component. At least one other sensing element, on the other hand, provides a reference signal. The reference signal may include a significant noise component, but not a significant target physiological component, for example, and can advantageously be used to produce a physiological signal having a reduced noise component. For example, certain embodiments employ adaptive filtering techniques to attenuate the noise component. In various embodiments, the noise component can come from a variety of sources, an can include, without limitation, ambient noise, interfering bodily sounds emanating from the patient (e.g., respiratory, heart or digestive sounds), noise coming from skin-coupled devices (e.g., surgical or other medical equipment), etc., further specific examples of which are provided herein.

Moreover, according certain aspects, the sensing elements are selectively configurable in a plurality of modes. For example, the sensing elements can be configured as either physiological signal sensing elements or noise sensing elements, as desired. As one illustrative example, a first sensor is used to detect respiratory sounds, while a second sensor used to detect heart sounds. In a first monitoring mode, the system uses the first sensor to detect the target respiratory sounds, and uses the second sensor as a noise reference sensor to minimize the effect of heart sounds (and/or other interfering noise) on the respiratory signal. Conversely, the system can switch to a second mode where the first sensor is used as the reference sensor to reduce the effect of respiratory sounds (and/or other interfering noise) on the signal produced by the second sensor. A wide variety of embodiments incorporating selective sensing element configurations are described herein.

Additionally, sensing elements (or groups thereof) can be arranged with respect to one another such that components of their output signals resulting from a common source (e.g., the patient's body) will be correlated or otherwise generally similar. The signal components from interfering noise sources, on the other hand, can be expected to be uncorrelated or otherwise have certain dissimilarities (e.g., phase or time shift). In these cases, the output signals from the first and second acoustic sensing elements can be combined in ways that accentuate commonalities between the two signals while attenuating differences.

In certain embodiments, a medical device is provided for non-invasively outputting a reduced noise signal responsive to acoustic vibrations indicative of one or more physiological parameters of a medical patient. In some embodiments, the medical device includes a first acoustic sensing element configured to be acoustically coupled to the body of a patient, the first acoustic sensing element being configured to output a first signal comprising a physiological signal component and a noise component. The medical device can also include a second acoustic sensing element being configured to output a second signal comprising at least a noise component. The medical device of some embodiments includes a noise attenuator configured to produce a reduced noise signal in response to the first and second signals. The reduced noise signal can include a physiological signal component and a noise component. In certain embodiments, the ratio of the physiological signal component of the reduced noise signal to the noise component of the reduced noise signal is greater than the ratio of the physiological signal component of the first signal to the noise component of the first signal.

According to certain aspects, a method of providing a reduced noise signal responsive to acoustic vibrations indicative of one or more physiological parameters of a medical patient is provided. The method can include outputting a first signal using first acoustic sensing element coupled to the body of a patient. The signal may comprise a physiological component and a noise component. The method can further including outputting a second signal using the second acoustic sensing element, the second signal comprising at least a noise component. In certain embodiments, the method further includes processing the first and second signals using a noise attenuator to produce a reduced noise signal in response to the first and second signals. The reduced noise signal can include a physiological signal component and a acoustic noise component. In certain embodiments, the ratio of the physiological signal component of the reduced noise signal to the noise component of the reduced noise signal greater than the ratio of the physiological signal component of the first signal to the noise component of the first signal.

In certain embodiments, a medical device is provided for non-invasively generating a reduced noise signal responsive to acoustic vibrations indicative of one or more physiological parameters of a medical patient. The medical device can include at least one first acoustic sensing element configured to generate a first signal in response to acoustic vibrations. The medical device of certain embodiments also includes at least one second acoustic sensing element configured to generate a second signal in response to acoustic vibrations. In certain embodiments, the medical device further includes a noise attenuation module configured to generate a reduced noise signal indicative of one or more physiological parameters of a medical patient in response to at least one of the first and second signals.

A medical sensor is provided in some embodiments for non-invasively outputting signals responsive to acoustic vibrations indicative of one or more physiological parameters of a medical patient. The medical sensor can include a first acoustic sensing element for generating a first signal. The medical sensor can also include a second acoustic sensing element for generating a second signal. The first and second signals in some embodiments are configured to be provided to a noise attenuator adapted to reduce a noise component of the first or second signal.

In certain embodiments, an acoustic sensor is provided for non-invasively outputting signals responsive to acoustic vibrations indicative of one or more physiological parameters of a medical patient. In certain embodiments, the acoustic sensor includes a sensor support. The acoustic sensor can also include a first acoustic sensing element at least partially supported by the sensor support and configured to output a first signal responsive to acoustic vibrations. The acoustic sensor of some embodiments includes a second acoustic sensing element at least partially supported by the sensor support and configured to output a second signal responsive to acoustic vibrations. In some embodiments, the first and second acoustic sensing elements are configured to provide the first and second signals to a noise attenuator configured to output a reduced noise signal having a higher signal to noise ratio than either of the first and second signals.

In certain embodiments, a method is provided of non-invasively outputting signals responsive to acoustic vibrations indicative of one or more physiological parameters of a medical patient. The method can include providing a sensor comprising a sensor support, a first acoustic sensing element at least partially supported by the sensor support, and a second acoustic sensing element at least partially supported by the sensor support. The method can further include outputting a first signal using the first acoustic sensing element. In certain embodiments, the first signal is responsive to acoustic vibrations, and the first acoustic sensing element is coupled to a medical patient. The method can include outputting a second signal using the second acoustic sensing element. In certain embodiments, the second signal responsive to acoustic vibrations, and the second acoustic sensing element coupled to the medical patient. In certain embodiments, the method includes providing the first signal and the second signal to a noise attenuator configured to output a reduced noise signal having a higher signal to noise ratio than either of the first and second signals.

In certain embodiments, an acoustic sensor is provided for non-invasively outputting signals responsive to acoustic vibrations indicative of one or more physiological parameters of a medical patient. The acoustic sensor can include a sensor support, and a first piezoelectric film at least partially supported by the sensor support and comprising a first electrode and a second electrode. In certain embodiments, the sensor includes a second piezoelectric film at least partially supported by the sensor support and comprising a first electrode and second electrode. In some embodiments, the first electrode of the first piezoelectric film and the first electrode of the second piezoelectric film are coupled to a common potential, and the second electrode of the first piezoelectric film and the second electrode of the second piezoelectric film are coupled to a noise attenuator.

In certain embodiments, an acoustic sensor is provided for non-invasively outputting signals responsive to acoustic vibrations indicative of one or more physiological parameters of a medical patient. In some embodiments, the acoustic sensor includes a sensor support. In some embodiments, the acoustic sensor includes a first acoustic sensing element at least partially supported by the sensor support and comprising an inner portion and an outer portion. In some embodiments, the acoustic sensor includes a second acoustic sensing element at least partially supported by the sensor support and comprising an inner portion and an outer portion. In certain embodiments, the acoustic sensor is configured such that the inner portions are positioned between the outer portions, the outer portions forming an electrical shielding barrier around the inner portions.

In certain embodiments, a method is provided of manufacturing an acoustic sensor for non-invasively outputting signals responsive to acoustic vibrations indicative of one or more physiological parameters of a medical patient. The method can include providing a first acoustic sensing element comprising an inner portion and an outer portion. The method can also include providing a second acoustic sensing element comprising an inner portion and an outer portion. In certain embodiments, the method includes attaching the first acoustic sensing element to a sensor support. The method in some embodiments includes attaching the second sensing element to the sensor support over the first acoustic sensing element. In certain embodiments, the inner portions of the first and second acoustic sensing elements are disposed between the outer portions of the first and second acoustic sensing elements, and the outer portions form an electrical shielding barrier around the inner portions.

An acoustic sensor is provided in some embodiments that is configured to non-invasively detect acoustic vibrations associated with a medical patient, the acoustic vibrations indicative of one or more physiological parameters of the medical patient. The sensor can include a sensor support and first and second sensing membranes supported by the sensor support, each of said first and second sensing membranes comprising first and second surfaces on opposite sides of each of said first and second sensing membranes. In some embodiments, the first and second sensing membranes are aligned such that said first surfaces face each other. The first surfaces in some embodiments are configured to provide an electrical signal indicative of a physiological parameter of a medical patient, and said second surfaces are configured to provide electrical shielding around said first surfaces.

In some embodiments, an acoustic sensor is provided that is configured to non-invasively detect acoustic vibrations associated with a medical patient. The acoustic vibrations can be indicative of one or more physiological parameters of the medical patient. In certain embodiments, the sensor includes at least one sound-sensing membrane is configured to detect acoustic vibrations associated with a medical patient when the acoustic sensor is attached to the medical patient. The sensor can also include a sensor support defining an acoustic cavity and configured to support the at least one sensing membrane over the acoustic cavity. The sensor support may include at least one pressure equalization pathway formed in a wall of the sensor support, the at least one pressure equalization pathway extending from the acoustic cavity to ambient air pressure.

In certain embodiments, an acoustic sensor is configured to non-invasively detect acoustic vibrations associated with a medical patient, the acoustic vibrations indicative of one or more physiological parameters of the medical patient. The sensor can include at least one sound-sensing membrane configured to detect acoustic vibrations associated with a medical patient when the acoustic sensor is attached to the medical patient. The sensor can further include a sensor support configured to support the at least one sensing membrane against the medical patient's skin. In some embodiments, the sensor is configured to provide an electrical signal in response to acoustic vibrations detected by the at least one sound-sensing membrane substantially independent of a force used to attach the sensor to the medical patient's skin.

In certain embodiments, an acoustic sensor can non-invasively detect acoustic vibrations indicative of one or more physiological parameters of a patient. The acoustic sensor can include a frame and a sensing element supported by the frame. The sensing element can output a signal responsive to acoustic vibrations associated with a patient when the acoustic sensor is attached to the patient. Further, the acoustic sensor can include an acoustic coupler supported by the frame and which can be coupled with an area of the skin of the patient. The acoustic coupler can include a bottom surface having a dielectric material that electrically decouples the area of the skin of the patient from the sensing element when the acoustic sensor is attached to the patient.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be re-used to indicate correspondence between referenced elements. The drawings are provided to illustrate embodiments of the inventions described herein and not to limit the scope thereof.

DETAILED DESCRIPTION

Various embodiments will be described hereinafter with reference to the accompanying drawings. These embodiments are illustrated and described by example only, and are not intended to be limiting.

Overview

In various embodiments, an acoustic sensor configured to operate with a physiological monitoring system includes an acoustic signal processing system that measures and/or determines any of a variety of physiological parameters of a medical patient. For example, in an embodiment, the physiological monitoring system includes an acoustic monitor. The acoustic monitor may be an acoustic respiratory monitor which can determine any of a variety of respiratory parameters of a patient, including respiratory rate, expiratory flow, tidal volume, minute volume, apnea duration, breath sounds, riles, rhonchi, stridor, and changes in breath sounds such as decreased volume or change in airflow. In addition, in some cases the acoustic signal processing system monitors other physiological sounds, such as heart rate to help with probe off detection, heart sounds (S1, S2, S3, S4, and murmurs), and change in heart sounds such as normal to murmur or split heart sounds indicating fluid overload. Moreover, the acoustic signal processing system may (1) use a second probe over the chest for additional heart sound detection; (2)

keep the user inputs to a minimum (example, height); and/or (3) use a Health Level 7 (HL7) interface to automatically input patient demography.

In certain embodiments, the physiological monitoring system includes an electrocardiograph (ECG or EKG) that measures and/or determines electrical signals generated by the cardiac system of a patient. The ECG includes one or more sensors for measuring the electrical signals. In some embodiments, the electrical signals are obtained using the same sensors used to obtain acoustic signals.

In still other embodiments, the physiological monitoring system includes one or more additional sensors used to determine other desired physiological parameters. For example, in some embodiments, a photoplethysmograph sensor determines the concentrations of analytes contained in the patient's blood, such as oxyhemoglobin, carboxyhemoglobin, methemoglobin, other dyshemoglobins, total hemoglobin, fractional oxygen saturation, glucose, bilirubin, and/or other analytes. In other embodiments, a capnograph determines the carbon dioxide content in inspired and expired air from a patient. In other embodiments, other sensors determine blood pressure, pressure sensors, flow rate, air flow, and fluid flow (first derivative of pressure). Other sensors may include a pneumotachometer for measuring air flow and a respiratory effort belt. In certain embodiments, these sensors are combined in a single processing system which processes signal output from the sensors on a single multi-function circuit board.

Figure 1A:
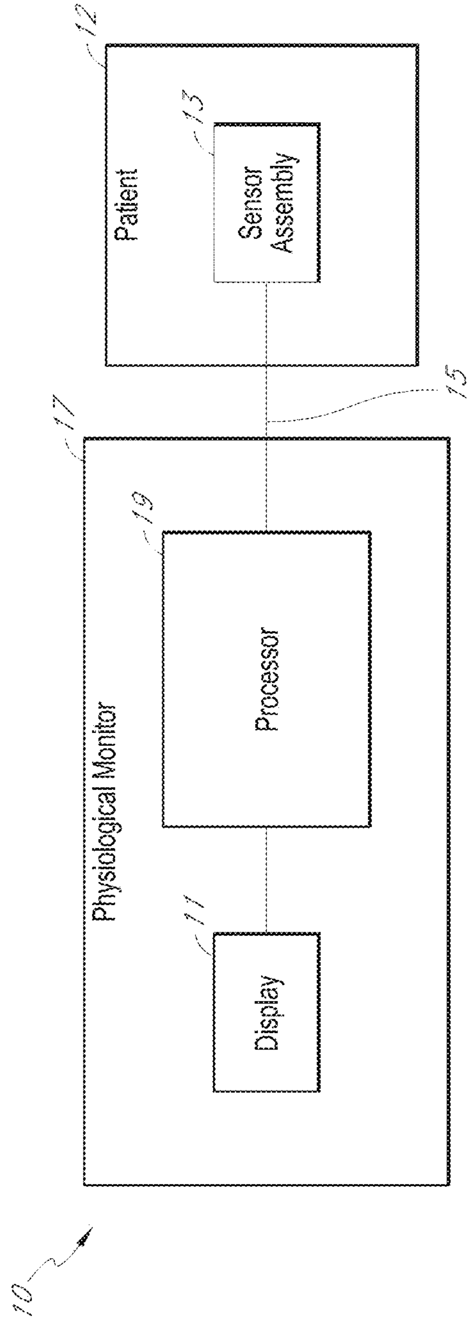
FIGS. 1A-B are block diagrams illustrating physiological monitoring systems in accordance with embodiments of the disclosure.
Figure 1B:
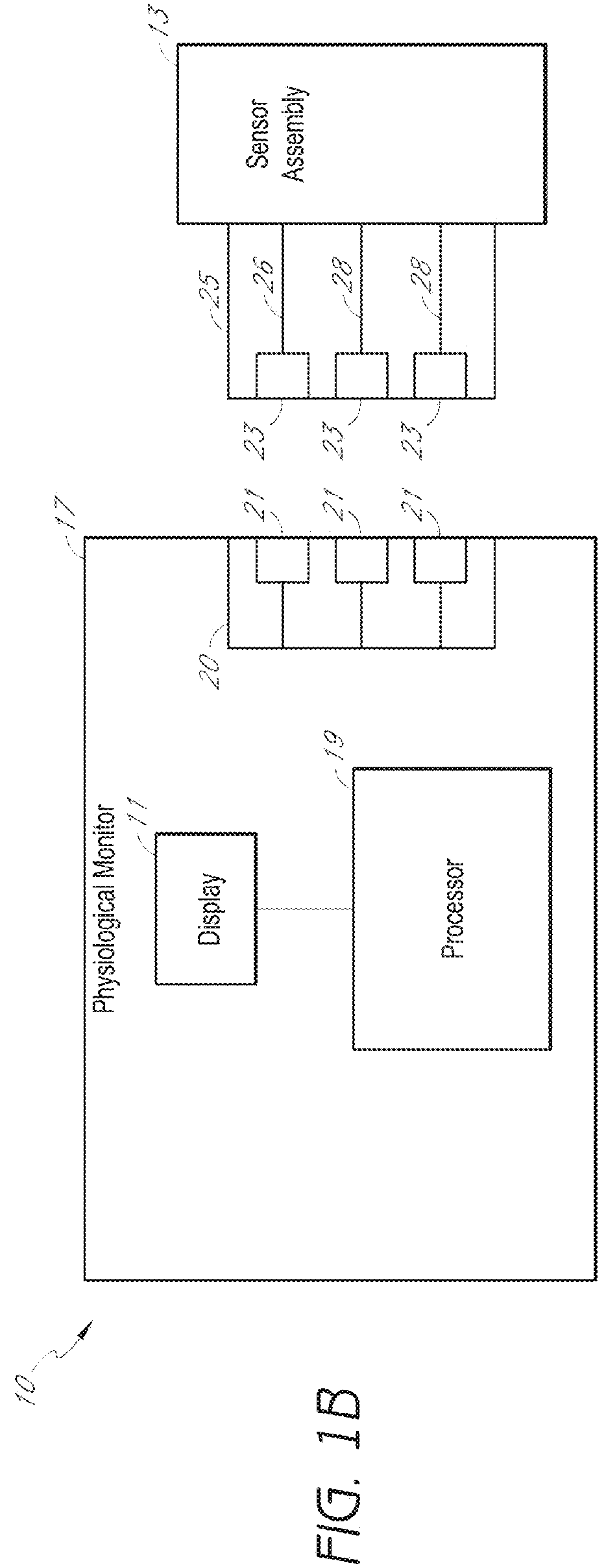
Figure 1C:
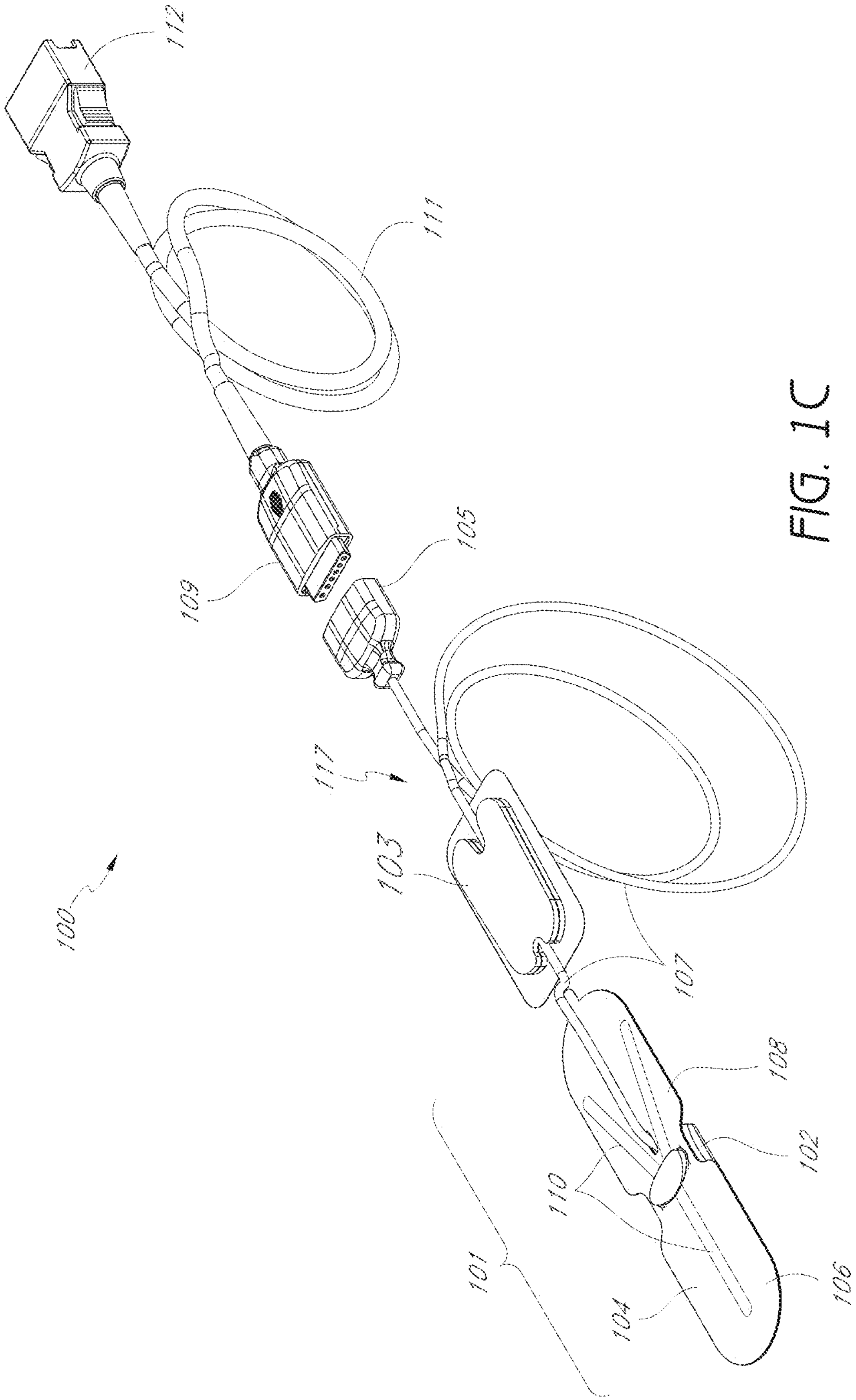
FIG. 1C is a top perspective view illustrating portions of a sensor system in accordance with an embodiment of the disclosure.

Referring to the drawings, FIGS. 1A through 1C illustrate example patient monitoring systems, sensors, and cables that can be used to provide acoustic physiological monitoring of a patient, such as respiratory monitoring. FIGS. 2A-18 illustrate embodiments of sensors and systems, such as those incorporating multiple acoustic sensing elements to provide certain beneficial results, including enhanced signal-to-noise ratio (SNR), electrical shielding and noise compensation, for example. Embodiments of FIGS. 2A-13B can be implemented at least in part using the systems and sensors described in FIGS. 1A through 1C. FIGS. 9A-13B show additional acoustic sensors and associated components compatible with embodiments described herein.

Turning to FIG. 1A, an embodiment of a physiological monitoring system 10 is shown. In the physiological monitoring system 10, a medical patient 12 is monitored using one or more sensor 13, each of which transmits a signal over a cable 15 or other communication link or medium to a physiological monitor 17. The physiological monitor 17 includes a processor 19 and, optionally, a display 11. The one or more sensors 13 include sensing elements such as, for example, acoustic piezoelectric devices, electrical ECG leads, pulse oximetry sensors, or the like. The sensors 13 can generate respective signals by measuring a physiological parameter of the patient 12. The signals are then processed by one or more processors 19. The one or more processors 19 then communicate the processed signal to the display 11. In an embodiment, the display 11 is incorporated in the physiological monitor 17. In another embodiment, the display 11 is separate from the physiological monitor 17. In one embodiment, the monitoring system 10 is a portable monitoring system. In another embodiment, the monitoring system 10 is a pod, without a display, that is adapted to provide physiological parameter data to a display.

For clarity, a single block is used to illustrate the one or more sensors 13 shown in FIG. 1A. It should be understood that the sensor 13 shown is intended to represent one or more sensors. In an embodiment, the one or more sensors 13 include a single sensor of one of the types described below. In another embodiment, the one or more sensors 13 include at least two acoustic sensors. In still another embodiment, the one or more sensors 13 include at least two acoustic sensors and one or more ECG sensors, pulse oximetry sensors, bioimpedance sensors, capnography sensors, and the like. In each of the foregoing embodiments, additional sensors of different types are also optionally included. Other combinations of numbers and types of sensors are also suitable for use with the physiological monitoring system 10.

In some embodiments of the system shown in FIG. 1A, all of the hardware used to receive and process signals from the sensors are housed within the same housing. In other embodiments, some of the hardware used to receive and process signals is housed within a separate housing. In addition, the physiological monitor 17 of certain embodiments includes hardware, software, or both hardware and software, whether in one housing or multiple housings, used to receive and process the signals transmitted by the sensors 13.

As shown in FIG. 1B, the acoustic sensor 13 can include a cable 25. The cable 25 can include three conductors within an electrical shielding. One conductor 26 can provide power to a physiological monitor 17, one conductor 28 can provide a ground signal to the physiological monitor 17, and one conductor 28 can transmit signals from the sensor 13 to the physiological monitor 17. For multiple sensors 103, one or more additional cables 115 can be provided.

In some embodiments, the ground signal is an earth ground, but in other embodiments, the ground signal is a patient ground, sometimes referred to as a patient reference, a patient reference signal, a return, or a patient return. In some embodiments, the cable 25 carries two conductors within an electrical shielding layer, and the shielding layer acts as the ground conductor. Electrical interfaces 23 in the cable 25 can enable the cable to electrically connect to electrical interfaces 21 in a connector 20 of the physiological monitor 17. In another embodiment, the sensor 13 and the physiological monitor 17 communicate wirelessly.

FIG. 1C illustrates an embodiment of a sensor system 100 including a sensor 101 suitable for use with any of the physiological monitors shown in FIGS. 1A and 1B. The sensor system 100 includes a sensor 101, a sensor cable 117, a patient anchor 103 attached to the sensor cable 117, and a connector 105 attached to the sensor cable 117. The sensor 101 includes a shell 102 configured to house certain componentry of the sensor 101, and an attachment subassembly 104 positioned the sensor 101 and configured to attach the sensor 101 to the patient. The sensor 101 can be removably attached to an instrument cable as described below with respect to FIGS. 1D through 1E. 111 via an instrument cable connector 109. The instrument cable 111 can be attached to a physiological monitor (not shown) via connector 112.

The component or group of components between the sensor 101 and the monitor in any particular embodiment may be referred to generally as a cabling apparatus. For example, where one or more of the following components are included, such components or combinations thereof may be referred to as a coupling apparatus: the sensor cable 117, the connector 105, the cable connector 109, the instrument cable 111, and/or the connector 112. It should be noted that one or more of these components may not be included, and that one or more other components may be included between the sensor 101 and the monitor, forming the cabling apparatus.

The acoustic sensor 101 can further include circuitry for detecting and transmitting information related to biological sounds to the physiological monitor. These biological sounds can include heart, breathing, and/or digestive system sounds, in addition to many other physiological phenomena. The acoustic sensor 101 in certain embodiments is a biological sound sensor, such as the sensors described herein. In some embodiments, the biological sound sensor is one of the sensors such as those described in U.S. patent application Ser. No. 12/044,883, filed Mar. 7, 2008, which is incorporated in its entirety by reference herein (the '883 application). In other embodiments, the acoustic sensor 101 is a biological sound sensor such as those described in U.S. Pat. No. 6,661,161 or U.S. patent application Ser. No. 12/643,939, filed on Dec. 21, 2009 (the '939 application), both of which are incorporated by reference herein in their entirety. Other embodiments include other suitable acoustic sensors. For example, in certain embodiments, compatible acoustic sensors can be configured to provide a variety of auscultation functions, including live and/or recorded audio output (e.g., continuous audio output) for listening to patient bodily or speech sounds. Examples of such sensors and sensors capable of providing other compatible functionality can be found in U.S. patent application Ser. No. 12/904,789, entitled ACOUSTIC RESPIRATORY MONITORING SYSTEMS AND METHODS, filed on Oct. 14, 2010, which is incorporated by reference herein in its entirety.

In an embodiment, the acoustic sensor 101 includes one or more sensing elements (not shown), such as, for example, a piezoelectric device or other acoustic sensing device. Where a piezoelectric membrane is used, a thin layer of conductive metal can be deposited on each side of the film as electrode coatings, forming electrical poles. The opposing surfaces or poles may be referred to as an anode and cathode, respectively. Each sensing element can generate a voltage potential across the electrical poles that is responsive to vibrations generated by the patient.

The shell 102 according to certain embodiments houses a frame (not shown) or other support structure configured to support various components of the sensor 101. The one or more sensing elements can be generally wrapped in tension around the frame. For example, the sensing elements can be positioned across an acoustic cavity disposed on the bottom surface of the frame. Thus, the sensing elements according to some embodiments are free to respond to acoustic waves incident upon them, resulting in corresponding induced voltages across the poles of the sensing elements.

Additionally, the shell 102 can include an acoustic coupler (not shown), which can advantageously improve the coupling between the source of the signal to be measured by the sensor (e.g., the patient's body) and the sensing element. The acoustic coupler of one embodiment includes a bump positioned to apply pressure to the sensing element so as to bias the sensing element in tension. For example, the bump can be positioned against the portion of the sensing element that is stretched across the cavity of the frame. In certain embodiments, the coupler can also advantageously provide electrical decoupling or insulation between the electrical components of the sensor and the skin of the patient.

The attachment sub-assembly 104 in some embodiments includes first and second elongate portions 106, 108. The first and second elongate portions 106, 108 can include patient adhesive (e.g., in some embodiments, tape, glue, a suction device, etc.). The adhesive on the elongate portions 106, 108 can be used to secure the sensor subassembly 102 to a patient's skin. One or more resilient backbone members 110 included in the first and/or second elongate portions 106, 108 can beneficially bias the sensor subassembly 102 in tension against the patient's skin and/or reduce stress on the connection between the patient adhesive and the skin.

While an example sensor system 100 has been provided, embodiments described herein are compatible with a variety of sensors and associated components. For example, compatible acoustic couplers, support frames, attachment subassemblies, sensing elements, and other components are described in greater detail below and in the '939 application.

Figure 1D:
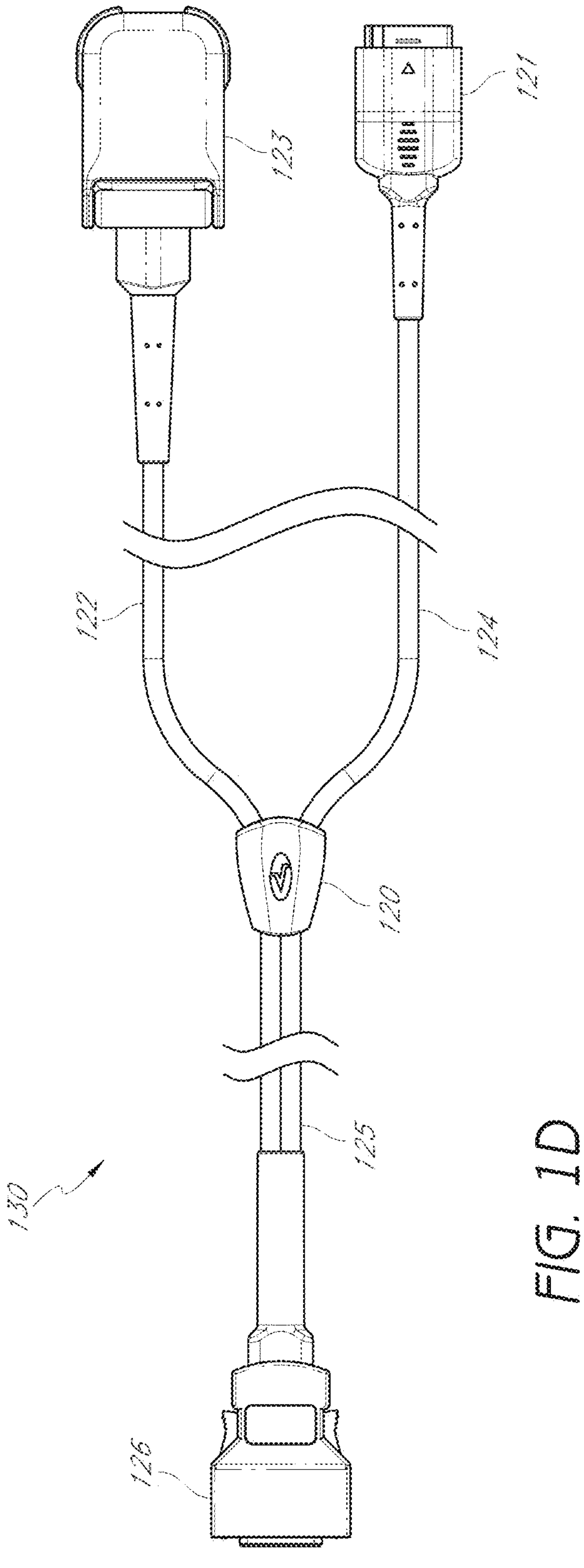
FIG. 1D is a top view illustrating an embodiment of a multi-sensor cable.
Figure 1E:
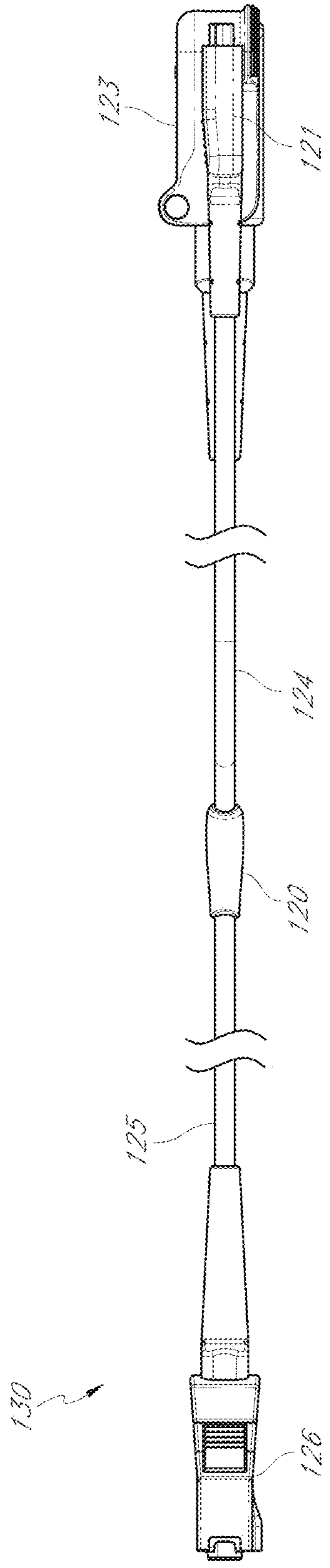
FIG. 1E is a side view of the multi-sensor cable of FIG. 1D.

FIGS. 1D and 1E depict an example dual sensor cable 130 that can be connected to the sensor 101 via the cable 111 as well as to another sensor. The dual sensor cable 130 can replace the single instrument cable 111 of FIG. 1C. The dual sensor cable 130 includes a connector 121 that can couple with the connector 105 of the sensor 101. Likewise, the dual sensor cable 130 includes a connector 123 that can connect to another sensor, such as a pulse oximetry sensor, other optical sensor, ECG sensor, or the like. In another embodiment, the dual sensor cable 130 connects to a second acoustic sensor.

The connector 121 is coupled with a cable section 124, and the connector 123 is also coupled with a cable section 122. These cable sections 122, 124 combine together in a junction 120 to form a single dual cable section 125 that terminates in a monitor connector 126. The junction 120 can be a piece of molded plastic or the like that joins the two cable sections 122, 124 together without electrically coupling the two cables. The monitor connector 126 can connect to a physiological monitor, enabling both sensors connected to the dual sensor cable 130 to provide physiological parameter data to the physiological monitor.

Advantageously, in certain embodiments, the dual sensor cable 130 is smaller than existing dual sensor cables that have extensive electrical decoupling or isolation circuitry inside. Isolation or decoupling circuitry can be included in dual sensor or multiple sensor patient cables to reduce or prevent ground loops from forming in a patient and thereby reduce or prevent electric shock to a patient, as described in U.S. application Ser. No. 12/904,775, filed Oct. 14, 2010, titled "Pulse Oximetry System with Low Noise Cable Hub," the disclosure of which is hereby incorporated by reference in its entirety. However, such circuitry is not included in the dual sensor cable 130 because decoupling can advantageously be performed by the sensor itself, as will be set forth more fully herein. As a result, the dual sensor cable 130 can be less bulky than the cable described in the '775 application while still providing the benefits of multiple sensor monitoring. In other embodiments, the dual sensor cable 130 can also be adapted to interface with more than two sensors, such as any of the sensors described herein.

Improving Signal-to-Noise Ratio Using Multiple Sensors

Figure 2A:
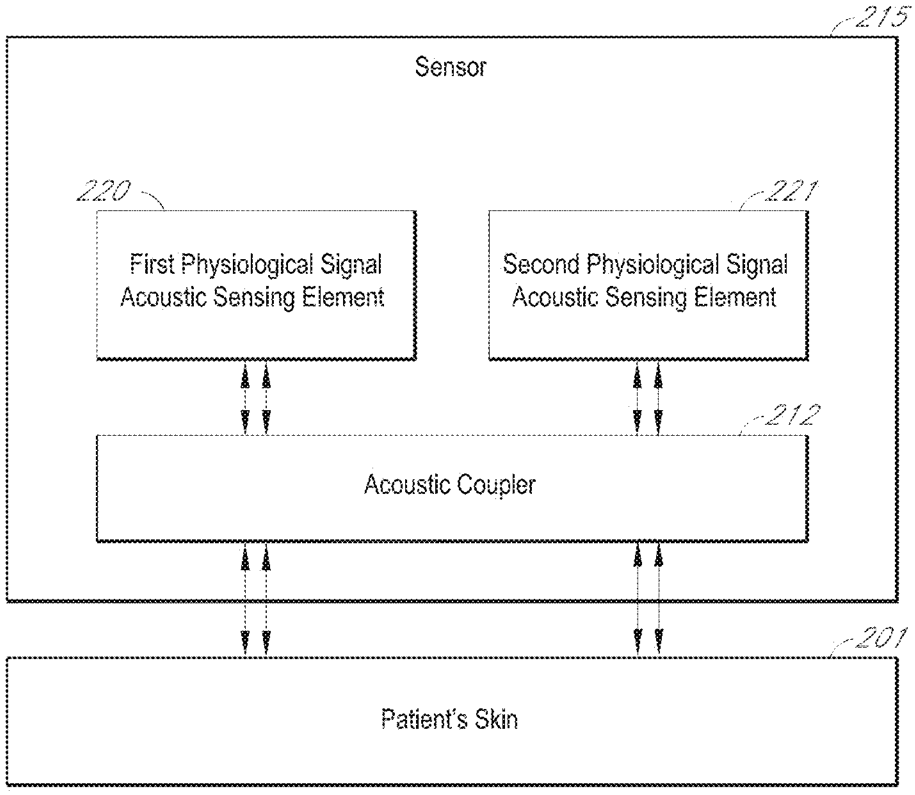
FIGS. 2A-2B are block diagrams of example embodiments of patient sensors that including first and second physiological signal acoustic sensing elements and at least one acoustic coupler for acoustically coupling both of the first and second physiological signal acoustic sensing elements to a patient's body.

FIG. 2A is a block diagram of an embodiment of a patient sensor 215 that includes first and second physiological signal acoustic sensing elements 220, 221. The sensing elements 220, 221 are generally adapted to detect physiological sounds from a patient 201, and can be any of the sensing elements described herein, such as piezoelectric membranes.

The patient sensor 215 can also include at least one acoustic coupler for acoustically coupling the first and second physiological signal acoustic sensing elements 220, 221 to a patient's body 201. In FIG. 2, both acoustic sensing elements 220, 221 are acoustically coupled to the patient. As shown in FIG. 1C, the acoustic coupling can be achieved using a single acoustic coupler 212 for both sensing elements.

According to one configuration, the acoustic sensing elements 220, 221 are supported in a stacked configuration on a sensor frame (not shown) or other support. Example stacked configurations are described below with respect to FIGS. 3B, 4A-4B and 6A-6D.

Figure 2B:
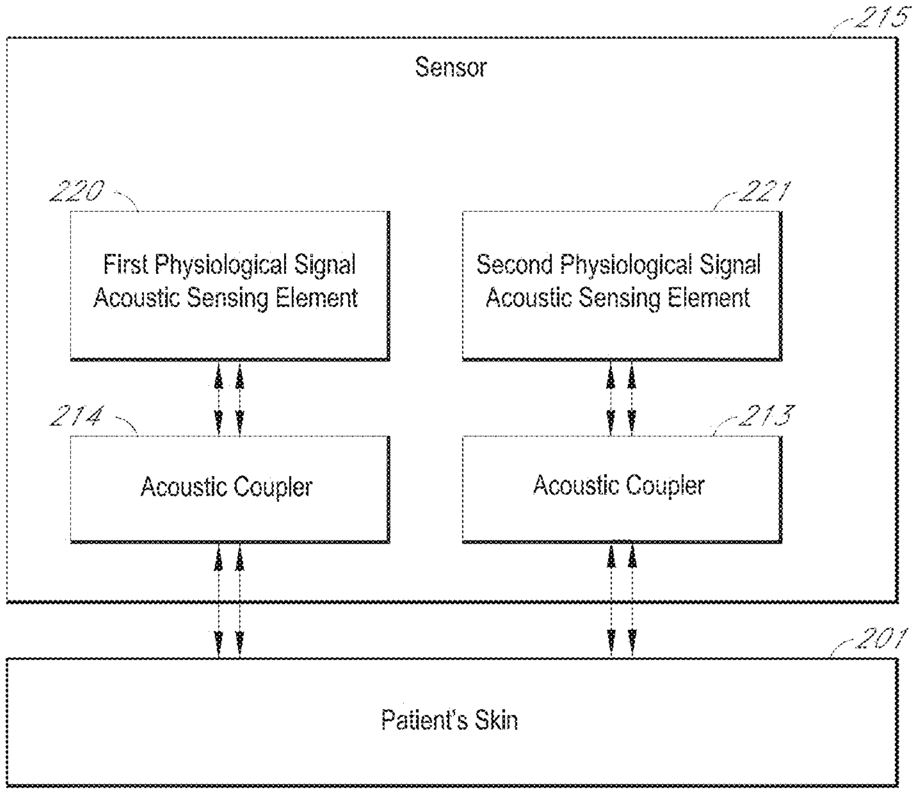

As shown in FIG. 2B, first and second acoustic couplers 213, 214 can be used in alternative embodiments. The acoustic couplers 213, 214 can be similar, for example, to the others described herein. In some embodiments, the acoustic sensing elements 220, 221 are supported in a side-by-side configuration on a frame. In other embodiments, no acoustic coupler is included.

In some embodiments, the acoustic coupler, or couplers, 213, 214 are designed to provide a substantially equal amount of coupling between each of the sensing elements 220, 221 and the patient's body 201, though this is not required. Example acoustic couplers compatible with the sensor 215 are described in greater detail throughout the disclosure.

As described, the first and second physiological signal acoustic sensing elements 220, 221 can be specially adapted to detect physiological sounds from a patient. However, the signals output by the acoustic sensing elements 220, 221 may also include noise (e.g., random noise, white Gaussian noise, etc.) from a variety of sources, which decreases the signal-to-noise ratio (SNR) of the signals.

The SNR of these signals can be improved, however, by collecting the desired physiological signal from more than one acoustic sensing element, and then combining (e.g., summing, subtracting, averaging, etc.) the respective outputs from the acoustic sensing elements in a manner that tends to reinforce the physiological signal components of the signals while tending to cancel or reduce the noise components of the signals. For example, the sensor 215, monitor, or other intermediate component, can include a noise attenuator which performs the combining of the signals from the sensing elements 220, 221 to achieve the improved SNR signal. Some embodiments of this approach are illustrated in FIGS. 3A-3B, 4A-4B and 6A-6B.

Generally, where sensors, sensing elements, couplers, etc., are described throughout the disclosure as being coupled to the patient's body, this may mean that one or more of the acoustic couplers are directly coupled to the patient's skin or other body part, such as where an acoustic coupler 212 is directly coupled to the skin 201 and transmits acoustic signals to one or more sensing elements 220, 221 as shown in FIG. 2A. However, this is not necessarily the case. For example, in some embodiments, the entire sensor, including couplers, where used, and/or sensing elements may be spaced from the patient's body and still receive acoustic signals emanating from the patient.

Figure 3A:
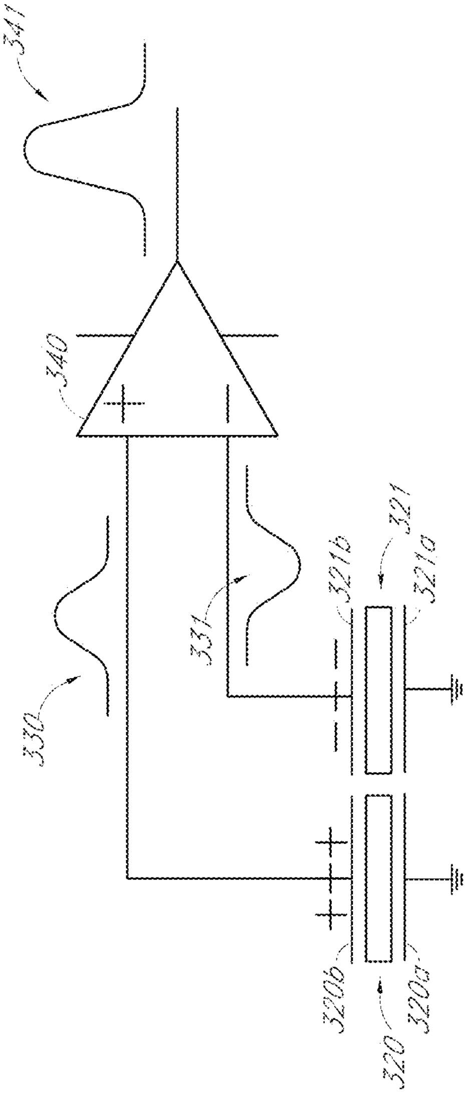
FIG. 3A is a schematic illustration of an embodiment of a circuit for improving signal-to-noise ratio by combining physiological signals from two or more acoustic sensing elements.

FIG. 3A is a schematic illustration of an embodiment of a circuit for improving signal-to-noise ratio by combining physiological signals from two or more acoustic sensing elements 320, 321. The two acoustic sensing elements 320, 321 may be acoustically coupled to the patient's body. In some embodiments, each of the first and second physiological signal acoustic sensing elements 320, 321 is a piezoelectric film, each having an anode and a cathode. The acoustic sensing elements 320, 321 detect physiological sounds from the patient's body and generate electrical waveforms corresponding to the physiological sounds. Example compatible piezoelectric films are described herein, with respect to FIGS. 4A-4B, 5A-5D, 6A-6B and 20A-20C, for example.

In FIG. 3A, the piezoelectric films 320, 321 are configured so as to generate output signals where the physiological signal components are 180° or approximately 180° out of phase. For example, in FIG. 3, the acoustic sensing elements 320, 321 generate voltage waveforms 330, 331 in response to physiological sounds from the patient. In the figure, the voltage waveform 330 is a positive pulse, while the voltage waveform 331 is a negative pulse, 180° out of phase from the positive pulse 330. Each of the physiological signal acoustic sensing elements 320, 321 is communicatively coupled to a sensing circuit 340. For example, the sensing circuit 340 may comprise or be referred to as a noise attenuator. In the illustrated embodiment, the sensing circuit 340 is a difference amplifier, though other sensing circuits 340 can be used.

In some embodiments, the 180° phase shift between the outputs from the two piezoelectric films 320, 321 is achieved by differentially connecting the piezoelectric films to the difference amplifier 340. For example, the cathode 320*b* of the first piezoelectric film 320 can be connected to the non-inverting terminal of the difference amplifier, while the anode 321*a* of the second piezoelectric film 321 can be connected to the inverting terminal of the difference amplifier 340. The anode 320*a* and the cathode 321*b* of the first and second films 320, 321, respectively, can be connected to ground (or be otherwise operatively coupled or coupled to a common potential). In some embodiments, the 180° phase shift is facilitated by mounting the two piezoelectric films 320, 321 such that one is flipped with respect to the other. For example, the two piezoelectric films 320, 321 can be mounted such that the cathode of one of the films faces toward the patient's body, while the anode of the other film faces toward the patient's body.

Since, in some embodiments, the physiological signal component of the second voltage waveform 331 is substantially a negative copy of the physiological signal component of the first voltage waveform 330, when these two waveforms 330, 331 are subtracted by the sensing circuit 340, they combine constructively, as indicated by the output waveform 341 from the sensing circuit 340. However, the outputs from the first and second piezoelectric films 320, 321 may also each include a noise component (not illustrated in the waveforms 330, 331). If the noise in the outputs from the piezoelectric films is random or otherwise uncorrelated, then at least a portion of the noise will tend to be combined destructively by the sensing circuit 340. Thus, the sensing circuit 340 can amplify the physiological signal component from the first and second piezoelectric films 320, 321 while attenuating random noise. The result in certain embodiments is that the physiological signal is emphasized while the random noise component of the output signals from the piezoelectric films 320, 321 is deemphasized.

For example, in one embodiment, the physiological signal is at least approximately doubled while the noise component is increased but less than doubled. The noise component might not double due to the random or uncorrelated nature of the noise, resulting in some portions of the noise combining additively while others combine negatively. Because the increase in the physiological signal can be greater than the increase in the noise, the sensor assembly configuration shown in FIG. 3A can improve signal to noise ratio (SNR).

Figure 3B:
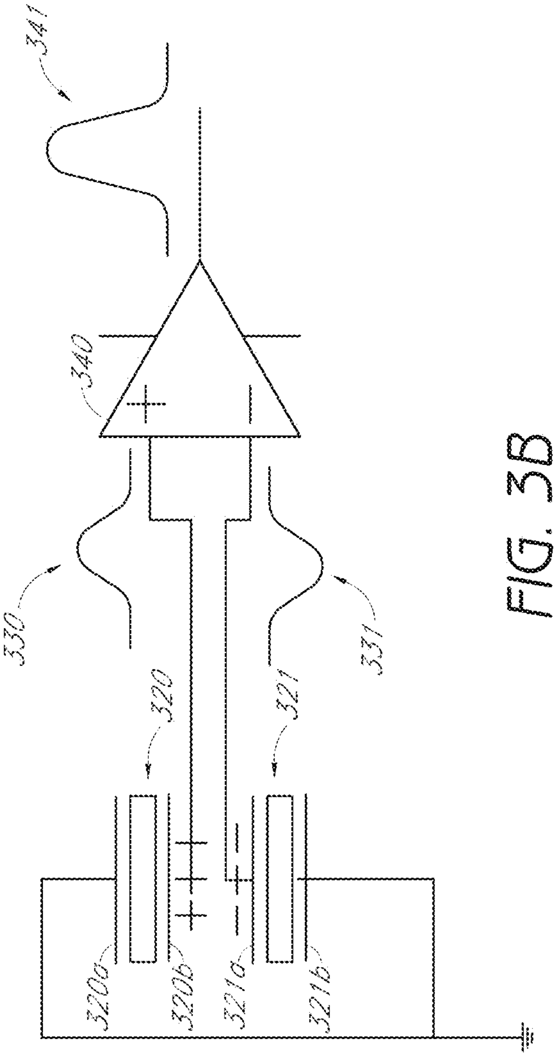
FIG. 3B is a schematic illustration of an embodiment of a circuit for improving signal-to-noise ratio by combining physiological signals from two or more acoustic sensing elements arranged in a stacked configuration.

While the configuration of FIG. 3A shows sensing elements 320, 321 in a side-by-side configuration, other configurations are possible. For example, FIG. 3B illustrates an embodiment of a circuit for improving signal-to-noise ratio where the sensing elements 320, 321 are in a stacked configuration with respect to one another. As described in further detail below with respect to FIGS. 4A-5B, the first sensing element 320 may be wrapped around a frame, and the second sensing element 321 may be wrapped around the first sensing element 320 and the frame.

Similar to the sensor configuration of FIG. 3A, the cathode 320*b* of the first piezoelectric film 320 can be connected to the non-inverting terminal of the sensing circuit 340, while the anode 321*a* of the second piezoelectric film 321 can be connected to the inverting terminal of the sensing circuit 340. Thus, in the illustrated embodiment the inner electrodes 320*b*, 321*a* of the first and second sensing elements 320, 321 generally face one another in the stacked configuration. The inner electrodes 320*b*, 321*a* are shown connected to the terminals of the sensing circuit 340, while the outer electrodes 320*a*, 321*b* are connected to ground.

Depending on the embodiment, the configuration shown in FIG. 3B can provide similar improved SNR advantages as described above with respect to FIG. 3A. In addition, as described herein (e.g., with respect to FIGS. 4A-6B), such a configuration can also provide enhanced electrical shielding. For example, the outer electrodes 320*a*, 321*b* of the sensing elements 320, 321, respectively, can be used to shield the inner electrodes 320*b*, 321*a* from electrical noise. As used herein, the terms "shield," "shielding," and the like, in addition to having their ordinary meaning, can mean reducing or attenuating noise, rather than completely eliminating noise. However, in some embodiments, the terms "shield," "shielding," and the like can also mean completely eliminating noise.

Generally, a variety of different sensing circuits 340 can be used in the embodiments of FIGS. 3A-3B and in generally any of the embodiments described herein where appropriate. Moreover, depending on the sensing circuit 340 used, the electrodes can be connected in a number of arrangements to achieve a similar SNR improvement. For example, a similar result could be obtained by connecting either both anodes or both cathodes, of the piezoelectric films 320, 321 to the inputs of a summing amplifier instead of a sensing circuit. In such embodiments, the physiological signal components of the outputs from the piezoelectric films can be approximately in phase and, therefore, can combine constructively when added by the summing amplifier. Still, at least a portion of random noise from the two output signals from the piezoelectric films 320, 321 will combine destructively, thereby attenuating noise and improving SNR. In some embodiments, more than two physiological signal acoustic sensing elements are used, and their inputs are summed together by, for example, a summing amplifier, a digital signal processor, etc. In some embodiments, one or more of the outer electrodes 320*a*, 321*b* can be operatively coupled to the sensing circuit 340, and one or more of the inner electrodes 320*b*, 321*a* are connected to ground. In yet other embodiments, the sensing circuit 340 comprises a coupling junction coupling together one or more of the electrodes of the respective sensing elements 320, 321.

Moreover, the number and arrangement of the sensing elements 320, 321 can vary according to certain aspects. For example, in some embodiments, more than two physiological signal acoustic sensing elements 320, 321 are used, and their inputs are summed together by, for example, a summing amplifier, a digital signal processor, etc. A variety of configurations including more than two sensing elements are possible. For example, in one embodiment a pair of stacked sensing elements is arranged in a side-by-side configuration on a frame with respect to another pair of stacked sensing elements. In other embodiments, more than two sensing elements (e.g., 3, 4, 5 or more) are arranged in a stacked configuration. In yet other embodiments, more than two sensing elements (e.g., 3, 4, 5 or more) are arranged side-by-side with respect to one another.

Figure 4A:
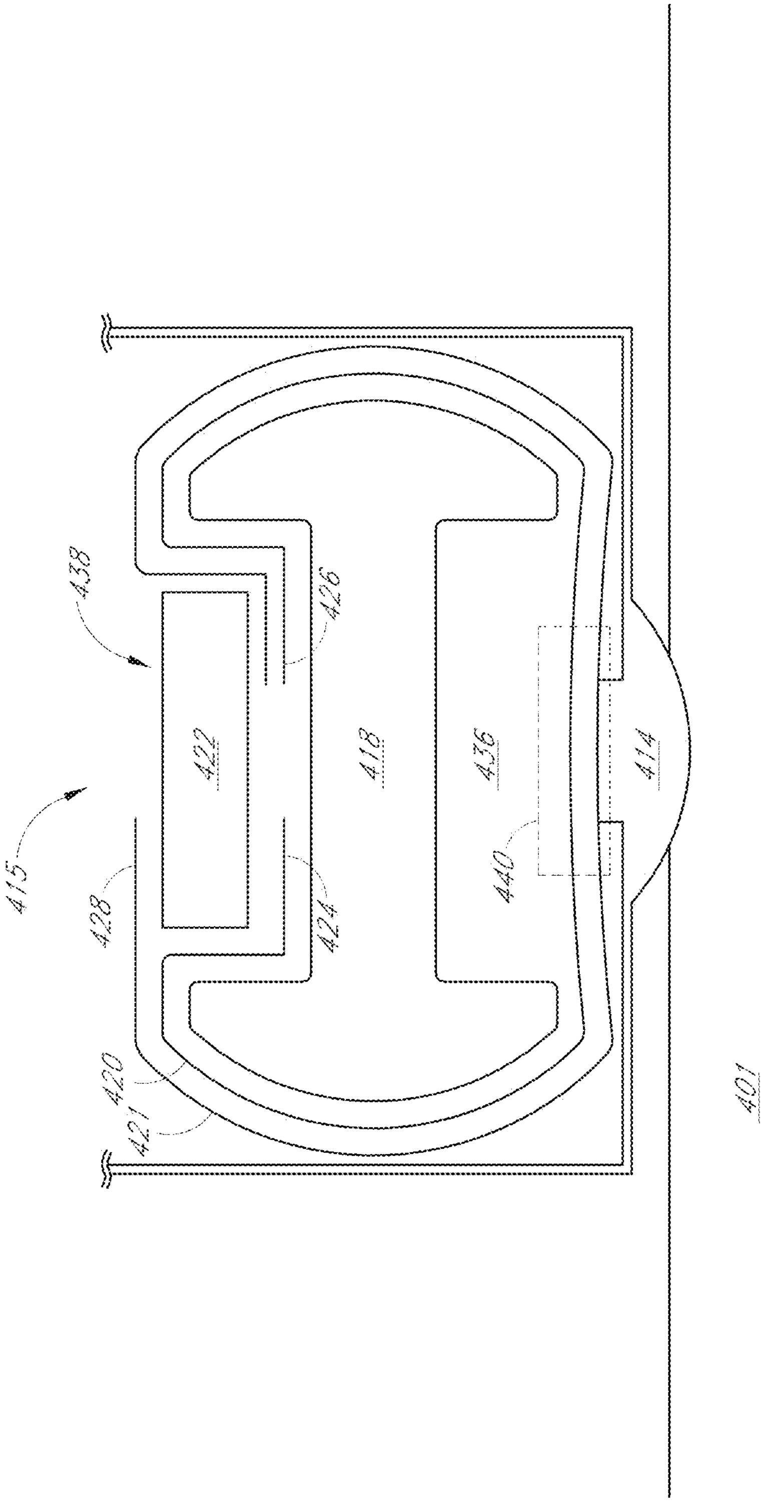
FIG. 4A is a cross-sectional schematic drawing of an embodiment of an acoustic sensor that includes first and second acoustic sensing elements in a stacked configuration.

FIG. 4A is a cross-sectional schematic drawing of an embodiment of an acoustic sensor 415 that includes first and second acoustic sensing elements 420, 421 in a stacked configuration. When connected to a sensing circuit (not shown, e.g., a difference amplifier) in the manner described above with respect to FIG. 3B, the acoustic sensor 415 can advantageously provide improved signal-to-noise ratio.

In the depicted embodiment, the first acoustic sensing element 420 is wrapped around a portion of the frame 418 and the second acoustic sensing element 421 is generally wrapped around the first acoustic sensing element 420 and also supported by the frame. In the illustrated embodiment, the physiological signal acoustic sensing elements 420, 421 are piezoelectric films. An acoustic coupler 414 acoustically couples the sensing elements 420, 421 to the patient's body 401, and can be aligned with both the first and second sensing elements 420, 421, as shown. In some other embodiments, an acoustic coupler 414 is not used. In the embodiment of FIG. 4A, the two piezoelectric films 420, 421 both extend over the acoustic cavity 436 of the frame 2118. Thus, the films 420, 421 are free to respond to acoustic waves incident upon them, resulting in induced voltages.

In the depicted embodiment, a PCB 422 is disposed in the upper cavity 438 of the frame 418, and is in electrical contact with one or more of the electrodes of the first and second sensing elements 420, 421. For example, the PCB 422 can be in electrical contact with the anode and cathode of each of the sensing elements 420, 421. While other configurations are possible, first and second ends 424, 426 of the first sensing element 420 can generally extend underneath opposite sides of the PCB 422. A first end 428 of the second sensing element 421 extends underneath the PCB 422, while a second end 430 of the second sensing element 421 extends over the opposing side of the PCB 422.

The upper side of the first ends 424, 428 of the first and second sensing elements 420, 422 can include contacts (not shown) corresponding to both electrodes of the respective sensing elements 420, 421. These contacts can be coupled to corresponding contacts on the underside of the PCB 422. One or more through holes or vias may be used to extend the electrodes on the underside of the ends 424, 428 of the sensing elements 420, 421 up to the upper side, enabling contact with appropriate PCB 422 contacts. Example first and second sensing elements compatible with the arrangement of FIG. 4 are described with respect to FIGS. 5A-6B. Additionally, another example piezoelectric membranes including through holes or vias are described below with respect to FIGS. 10A-10C.

While not shown for the purpose of clarity, in one embodiment, at least one additional layer (not shown) can be disposed between the sensing elements 420, 421. The additional layer can include an adhesive that adhesively couples the sensing elements 420, 421 together. This adhesive coupling can help ensure that the sensing elements 420, 421 move uniformly together in response to vibrations, reducing losses and improving the response of the sensor. The adhesive coupling can also at least partially maintain tension of one or more of the sensing elements 420, 421.

The additional layer can further be configured to insulate the sensing elements 420, 421 from one another, preventing shorts, noise and/or other undesirable electrical behavior. For example, the additional layer can include a dielectric material. In an embodiment, the adhesive described above acts as a dielectric material. Additional adhesive layers are described below with respect to FIGS. 6A-6B, 9D-9E and 6D-6E, for example.

The ends of the sensing elements 420, 422 may be configured to provide improved sensor performance, reliability, etc. For example, the additional layer may extend to the ends of one or more of the sensing element 420, 422. In one embodiment, the additional layer is an adhesive layer extending to the under side of the second end 430 of the second sensing element 420, helping secure the connection between the second sensing element 422 and the PCB 422. Moreover, in such embodiments, the second end 430 may be generally stretched across the top of the PCB 422, biasing one or more of the sensing elements 420, 421 in tension and thus providing an improved piezoelectric response.

Depending on the embodiment, one or more of the ends of the sensing elements 420, 421 can also include a dielectric material. For example, in one embodiment, the underside of the second end 430 of the second sensing element 421 includes a dielectric material, thereby insulating the second end 430 and the PCB 422. Additionally, the electrode coatings can be configured to reduce the possibility of electrical shorts or other undesirable behavior. In one embodiment, for example, the electrode coating on the underside of the second sensing element 421 does not extend to the second end 430, thereby reducing the risk of undesirable electrical contact between the second end 430 and the top surface of the PCB 422. In another embodiment, a dielectric material is placed on the underside of the PCB 422 instead of or in addition to providing a dielectric material on the end of the sensing element 420 or 421.

A variety of other configurations are possible for the arrangement of the sensing elements 420, 421. For example, in one embodiment, the ends of the sensing elements 420, 421 which are not connected to the PCB 422 do not extend over or under the PCB 422. In another embodiment, each end of the sensing elements 420, 421 includes one electrode contact, and all four ends are thus in electrical contact with corresponding contacts on the PCB 422. This is in contrast with the arrangement described above, in which the upper side of the first ends 424, 428 each include both anode and cathode electrode contacts for the respective sensing elements 420, 421.

As discussed, and as with many of the embodiments described herein, the piezoelectric films 420, 421 are shown in FIG. 4A spaced apart for clarity and ease of illustration. However, in addition to the additional layers described above, the two piezoelectric films 420, 421 can be separated by one or more mechanical supports, acoustic decouplers, shielding layers, or other layers or components. Additionally, any of these layers may be disposed between the frame 418 and the first piezoelectric film 420 and/or wrapped around the outside of the second sensing element 421.

Shielding Using Multiple Sensing Elements

In certain embodiments, multiple sensing elements can be employed to form an electrical noise shielding barrier, providing electrical shielding. Moreover, using the sensing elements or portions thereof to form the barrier can simplify the design of the sensor, reducing costs. For example, one or more stacked sensing elements can be configured to electrically shield the sensor. In some configurations, where the stacked sensing elements are piezoelectric films, the inner, facing electrodes of the films in the stack are used to communicate voltage signals generated by the piezoelectric elements to the sensing circuitry of the sensor (and/or monitor). The outer electrodes of the films in the stack can advantageously be configured to shield the inner electrodes from electrical noise. Generally, throughout the disclosure, the term "inner" refers to the sensing element surface and/or electrode coating which is facing the other sensing element in the active region of the stack (e.g., across the acoustic cavity). Conversely, the term "outer" refers to the sensing element surface and/or electrode which is facing away from the other sensing element in the active region of the stack.

The electrical noise shielding barrier can electrically shield the electrical poles of the sensing element from external electrical noises. In some embodiments the outer portions of the sensing element form a Faraday cage or shield around the inner portions. Thus, the outer portions can distribute external electrical noise substantially equally to the electrical poles of the piezoelectric sensing element. The shield can act to reduce the effect of noise on the sensing element from sources such as external static electrical fields, electromagnetic fields, and the like.

Using a second sensing element to form an electrical shielding barrier can also help to reduce costs by reducing the complexity involved in constructing the sensor and reducing material costs. For example, such embodiments may not include one or more shielding layers which are physically separate from the sensing elements (e.g., copper shielding layers), reducing manufacturing costs associated with purchasing and handling such components. However, certain aspects of shielding barriers formed from multiple sensing elements described herein are compatible with shielding barriers formed from separate layers and aspects thereof. Example shielding barriers including those formed from separate shielding layers are described with respect to FIGS. 2D-2E below and throughout the '939 application, including, without limitation, paragraphs [0120]-[0146] and FIGS. 2D-2E of the '939 application which are incorporated by reference herein.

Figure 4B:
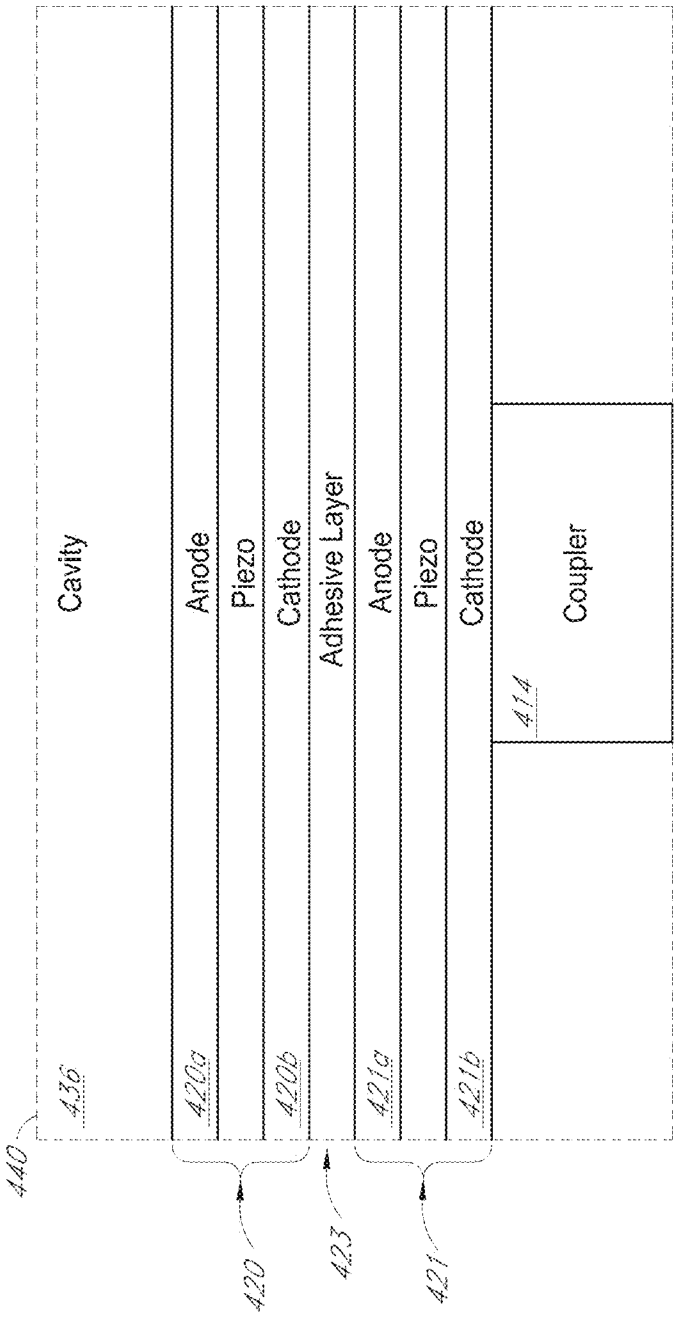
FIG. 4B shows a cross-sectional schematic drawing of a portion of the first and second stacked sensing elements of FIG. 4A.

FIG. 4B shows a partial cross-sectional schematic drawing of a portion 440 of the first and second stacked piezoelectric films 420, 421 of FIG. 4A. As shown, each of the first and second piezoelectric films 420, 421 respectively include an anode 420*a*, 421*a* and a cathode 420*b*, 421*b* on opposing sides of the films 420, 421. In some embodiments, the films 420, 421 include one of the piezoelectric films described with respect to FIG. 2B-E or 3A-C, for example.

As shown, the films 420, 421 are disposed with respect to each other in a stacked configuration such that the cathode 420*b* of the first film 420 is facing the anode 421*a* of the second film 421. Thus, these two inner electrodes 420*b*, 421*a* of the stack are generally sandwiched between the anode 420*a* of the first film 420 and the cathode 421*b* of the second film 421, which form the outer electrodes of the stack. The inner electrodes 420*b*, 421*a* can be operationally coupled to a sensing circuit (e.g., a differential amplifier) in the manner shown in FIG. 10B, advantageously providing improved signal-to-noise-ratio in some embodiments.

In addition, the outer electrodes 420*a*, 421*b* of the films 420, 421 can be configured to form layers of an electrical noise shielding barrier, providing the additional benefit of electrically shielding the sensor from external electrical noises. The electrical noises shielded (or at least partially shielded) can include electromagnetic interference (EMI) from various sources, such as 50 or 60 Hz (AC) noise, noise from other medical devices, and so forth. In some embodiments for example, the outer electrodes 420*a*, 421*b* of the first and second films 420, 421 form a barrier around the inner electrodes 420*b*, 421*a* of the first and second films 420, 421. Thus, a significant amount of external electrical noise is not directly incident on the inner electrodes 420*b*, 421*a*. The outer electrodes 420*a*, 421*b* can, for example, distribute at least a portion of the external electrical noise substantially equally to the inner electrodes 420*b*, 421*a*, which form the electrical poles of the sensor. For example, because the outer electrodes 420*a*, 421*b* may share a common potential (e.g., ground), noise incident on either of the outer electrodes 420*a*, 421*b* can be distributed equally to each electrode 420*a*, 421*b*. The equally distributed noise can then be capacitively coupled to the inner electrodes 420*b*, 421*a*.

Thus, in certain embodiments, because the noise is equally distributed, the noise signal components on the inner electrodes 420*b*, 421*a* will be substantially in phase. The physiological signal components can be substantially out of phase, on the other hand, due to the differential orientation of the inner electrodes 420*b*, 421*a* with respect to one another in some implementations. The noise signals can advantageously be removed or substantially removed, such as through a common-mode rejection technique as described herein. In certain embodiments, at least some of the external electrical noise is shunted or otherwise directed to ground instead of, or in addition to, being equally distributed to the inner electrodes 420*b*, 421*a*.

A variety of alternative configurations are possible. For example, more than two sensing elements (e.g., 2, 3, 4, 5 or more) may be arranged to provide electrical shielding and/or improved signal-to-noise ratio in some embodiments. Moreover, the particular polarities of the sensing elements 420, 421 of FIG. 4 are not intended to be limiting. In another embodiment, one or more of the sensing elements 420, 421 are flipped. For example, the sensing elements 420, 421 are flipped such that the anode 420*a* of the first sensing element 420 faces the cathode 421*b* of the second sensing element 421.

Additionally, shielding barriers formed using stacked sensing elements 420, 421 can provide improved coupling of bodily sounds to the sensor, improving sensor operation (e.g., sensor sensitivity, measurement reliability, etc.). Generally, portions of both the shielding barrier and the sensing element will tend to vibrate in response to the patient sounds. Thus, an uneven mechanical response between the shielding barrier and the sensing element may result in lost signal, affecting sensor performance. For example, shielding barriers including layers that are physically separate from the sensing element can be, in some cases, relatively stiffer than the sensing element. This can limit movement of the sensing element in response to vibrations, producing a corresponding limiting affect on sensor sensitivity. In contrast, where electrodes of the sensing elements are used as shielding layers, the shielding barrier and the sensing element are generally formed from the same type material and integrally connected. Thus, the sensor may be relatively more responsive to vibrations, improving sensor operation.

Moreover, each of the outer electrode shield layers in the stacked configuration can be evenly spaced from the respective inner electrode sensor poles, particularly across the mechanically active portions of the sensor (e.g., across the frame cavity 436 of FIG. 4A). The capacitance between the shield layer and sensor pole on a first side of the sensing element stack can be very highly matched (e.g., substantially equal to) with the capacitance between the shield layer and sensor pole on the opposing side of the stack. Thus, a stacked sensing element configuration can provide a more even distribution of external electrical noise to the poles of the sensing element, improving noise rejection.

According to certain aspects, the physical configuration of the electrodes of the first and second films 420, 421 can be tailored to provide improved electrical shielding. For example, the outer electrodes 420*b*, 421*a* can be plated using a material selected to provide enhanced shielding. Although other materials may be used, in one embodiment, the outer electrodes 420*b*, 421*a* are plated with silver ink. Moreover, in certain embodiments, the outer electrode coatings of the piezoelectric stack cover a greater portion of the surface area of the respective piezoelectric films than the inner electrode coatings. For example, the outer electrode coatings may cover a significantly larger portion of the surface area of the respective piezoelectric films than the inner electrode coatings. In certain embodiments, for example, the outer electrodes generally envelope or surround the inner electrodes or a substantial portion thereof when the films 420, 421 are in a stacked configuration. Thus, the amount of surface area of the inner electrodes which is exposed to electrical noise is reduced due to the mechanical and/or electrical barrier created by the surrounding outer electrodes.

Figure 5A:
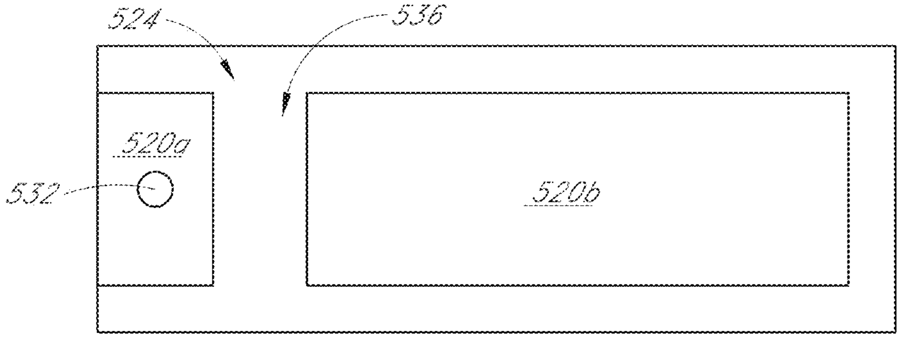
FIGS. 5A-5D show views of example acoustic sensing elements having electrode coating configurations tailored for use in a stacked configuration.
Figure 5B:
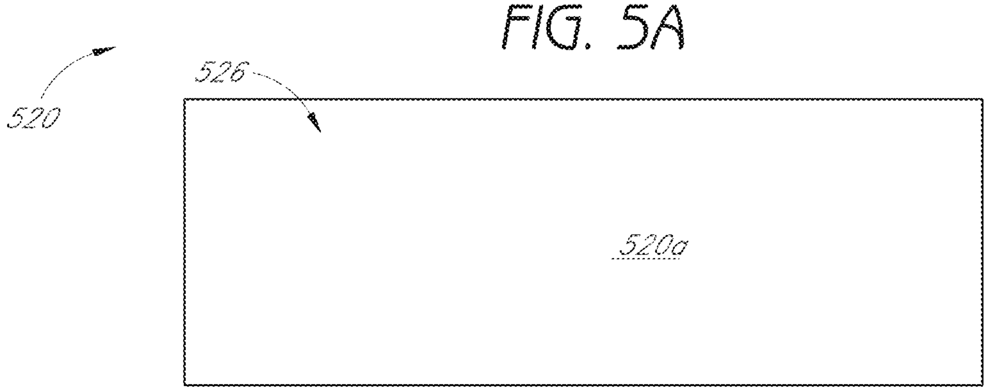
Figure 5C:
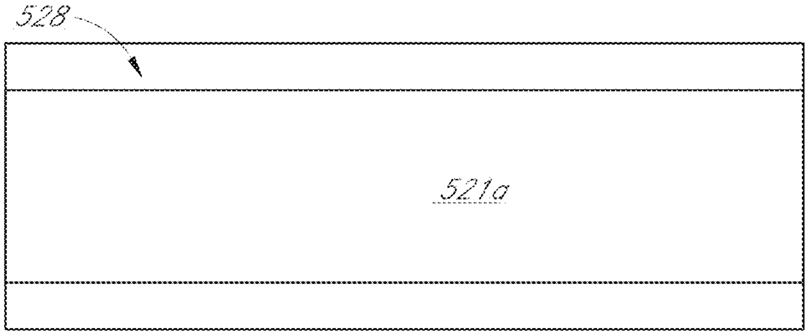
Figure 5D:
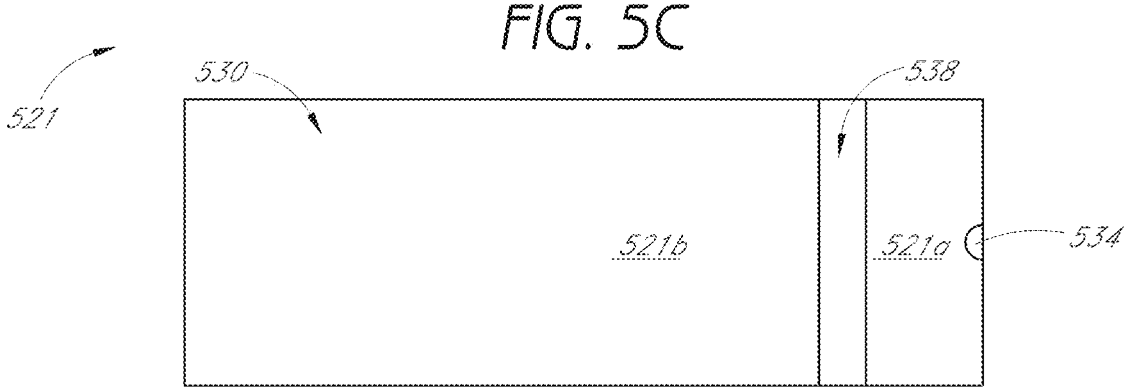

FIGS. 5A-5D illustrate example sensing elements 520, 521 having electrode coating configurations tailored for use in a stacked configuration. FIGS. 5A-5B show example first and second (e.g., inner and outer) surfaces 524, 526 of a first example acoustic sensing element 520. FIGS. 5C-5D show example first and second (e.g., inner and outer) surfaces 528, 530 of a second acoustic sensing element 521. While the films 520, 521 are shown in an unfolded configuration for the ease of illustration, the second sensing element 521 may be wrapped around the first sensing element 520 on a frame as shown in FIGS. 4A-4B. Thus, the sensing elements 520, 521 are also referred to as the interior and exterior sensing elements, respectively.

The interior sensing element 520 includes an anode electrode coating 520*a* on the outer surface 526 which extends via a through hole 532 to a portion on one end the end of the inner surface 524. The inner surface 524 of the first sensing element 520 also includes a cathode coating 520*b*. The exterior sensing element 521 includes an anode electrode coating 521*a* on the inner surface 528 which extends via a through hole 534 to a portion on one end of the outer surface 530. The outer surface of the exterior sensing element 521 also includes a cathode electrode coating 521*b*.

As shown in FIG. 5B, the outer electrode surface of the first (interior) film 520 covers a substantially greater percentage of the surface area of the outer surface 526 of the film 520 than do the inner electrode surfaces on the opposing, inner surface 524 of the film 520, shown in FIG. 5A. For example, in the illustrated embodiment, the outer electrode coating shown on FIG. 5B covers substantially the entire outer surface 526 area of the film 520, while the electrode coatings on the inner surface 524 form a pair of generally rectangular strips covering only a portion of the inner surface 524 area of the film 520. Similarly, as shown in FIGS. 5C-D, the outer electrode coatings on the outer surface 530 of the second (exterior) film 521 covers a substantially greater surface area of the outer surface 530 of film 521 than the inner electrode coating on the inner surface 528 of the film 521. For example, in certain embodiments, the electrode coating on the exterior surface of one or more of the films 520, 521 covers at least 2 percent more of the film surface area than the do the interior electrodes. In other embodiments, the exterior electrodes cover at least 1, 5, 10, 15 or greater percent more of the exterior surface area than the do the interior electrodes. Additionally, the exterior electrode can cover at least 90 percent of the exterior film surface in some embodiments. In other embodiments, the exterior electrode covers at least 70, 75, 80, 85, 95 or more percent of the exterior film surface.

As described with respect to FIGS. 4A-4B, the through holes 532, 534 facilitate electrical contact between the respective electrodes and one or more components of the sensor (e.g., a PCB contact). Moreover, the electrode which is extended to the opposing side through the at least one through hole 540 can be electrically isolated from the other electrode on the respective film the by gaps 536, 538 in the electrode coatings.

In such embodiments, where an electrode coating covers substantially the entire surface area of the piezoelectric film, or otherwise covers a significantly larger portion of the surface area of the piezoelectric film than the electrode coating on the opposing side, the electrode coating may be referred to as "flooded." Thus, the configuration of FIG. 5 generally includes un-flooded inner electrodes generally sandwiched between flooded outer electrodes. Such configurations can reduce surface area of the inner electrodes that is exposed to electrical noise, improving electrical shielding.

A wide variety of flooded electrode configurations are possible. For example, in some embodiments, the sizes and shapes of the electrode coatings may differ from the illustrated embodiment. The relative sizes of the inner electrode coatings versus the outer electrode coatings can also vary. For example, the inner electrode coatings are much smaller in relation to the outer electrode coatings than is shown.

In some alternative embodiments, the outer and inner electrode coatings are both flooded or otherwise cover about the same surface area, or the electrode coating on the inner electrode coating covers more surface area than the outer electrode. Such embodiments may, in some cases, provide relatively less shielding than embodiments where the outer electrode coatings cover more surface area than the inner electrodes, but nonetheless provide some significant amount of electrical shielding.

Example Sensor

Figure 6A:
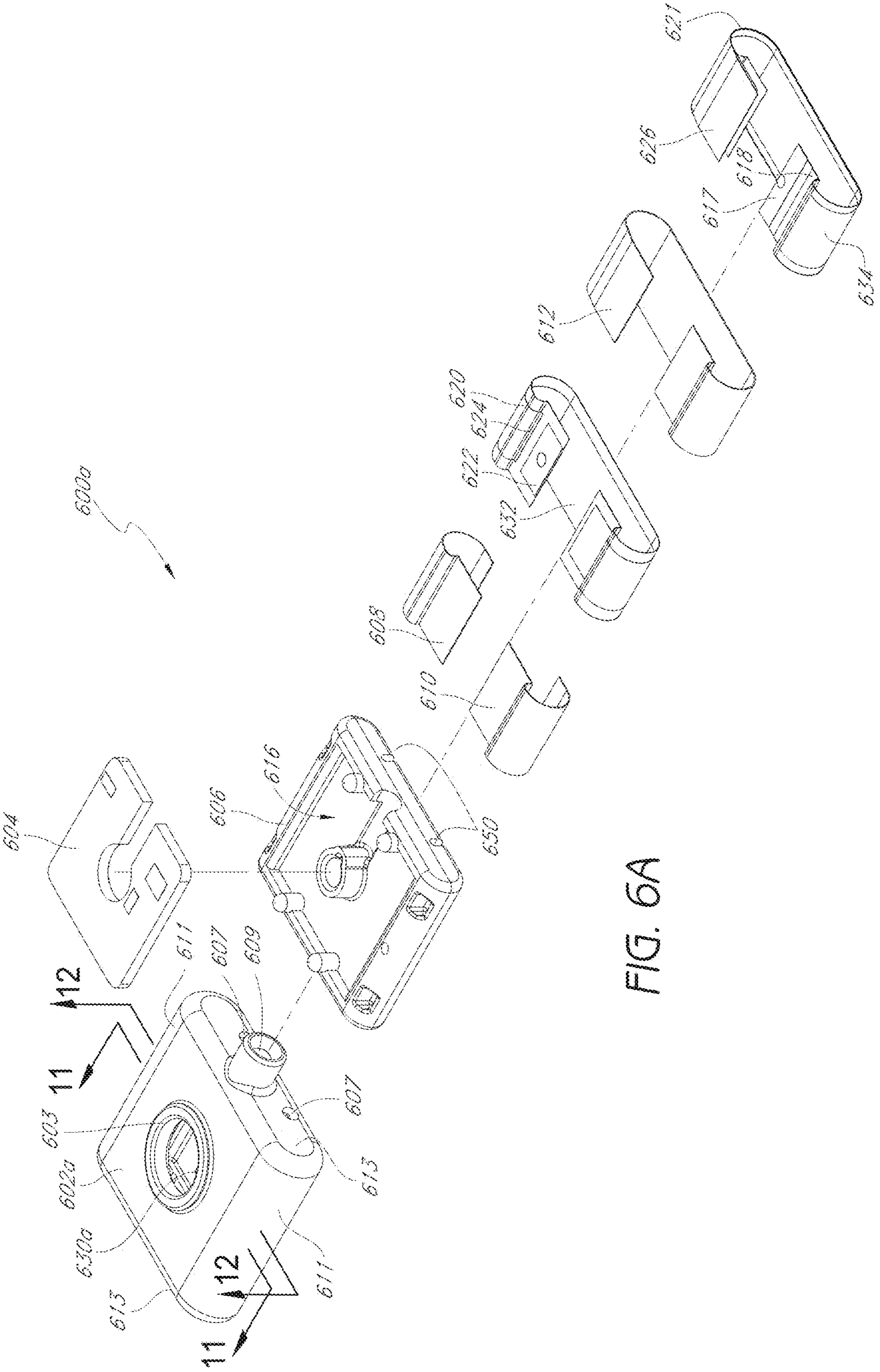
FIGS. 6A-6B are top and bottom exploded, perspective views, respectively, of a sensor incorporating an embodiment of an improved coupler in accordance with embodiments described herein.
Figure 6B:
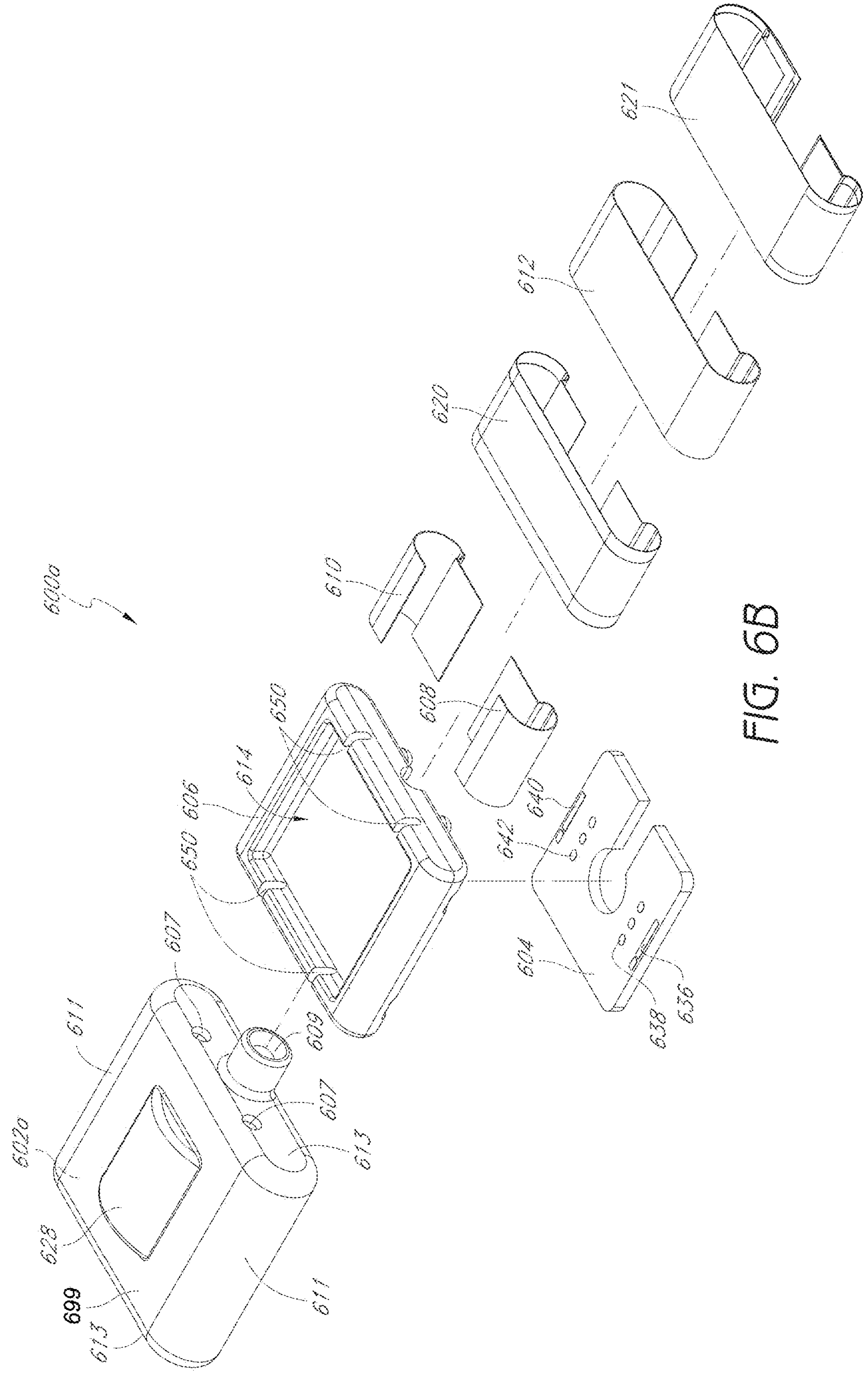

FIGS. 6A-6B illustrate an exploded view of an example sensor 600*a* configured to detect acoustic physiological sounds from the patient incorporating certain beneficial aspects described herein. For example, the sensor 600*a* provides improved SNR using multiple sensing elements according to techniques described above with respect to FIGS. 2A-4B. Moreover, the sensor 600*a* includes a stacked, multiple sensing element configuration providing enhanced shielding, compatible with the techniques described above with respect to FIGS. 4A-5D.

The sensor 600*a* is generally attachable to a patient and can be coupled to a patient monitor. For example, the sensor 600*a* can be used with the system 10 of FIGS. 1A-1B. Additionally, the sensor 600*a* may be compatible with the sensor system 100 of FIG. 1C. For example, the sensor 600*a* may be the sensor 101 of FIG. 1C, and can include an attachment mechanism (not shown) for attaching the sensor to a patient, such as the attachment subassembly 104 of FIG. 1C.

Referring to FIG. 6A, the sensor 600*a* of certain embodiments includes an acoustic coupler shell 602*a* (shown in FIG. 6A in an unstretched state), a printed circuit board (PCB) 604, a frame 606, first and second acoustic sensing elements 620, 621, and multiple adhesive layers 608, 610, 612. The coupler shell 602*a* houses the frame 606, which is generally configured to support various components of the sensor 600*a* in an assembled state, including the PCB 604, sensing elements 620, 621, and adhesive layers 608, 610, 612. The sensing elements 620, 621 are piezoelectric films in the illustrated embodiment, although other types of sensing elements can be used. A cable sleeve 609 in the acoustic coupler 602*a* can encircle a cable inserted into the cable sleeve 609, which cable can connect electrically with the PCB 604, such as any of the cabling described above.

Advantageously, in certain embodiments, the acoustic coupler shell 602*a* or coupler 602*a* has structural characteristics that can provide patient decoupling or patient isolation benefits. In particular, with reference to FIG. 6B, the coupler 602*a* is substantially enclosed on its bottom surface 699, where the coupler 602*a* contacts skin of the patient. In addition, the sides 611, 613 of the coupler 602*a* wrap around the frame, further protecting the skin of the patient from contact with the sensing elements 620, 621 and PCB 604 of the sensor 600*a*.

In currently-available acoustic sensors (such as in the '939 application), the coupler has slits in the bottom surface to enable the coupler to move more freely with the patient's vibrations and thereby increase signal to noise ratio. However, the open slits potentially expose the patient's skin to harmful currents, and thus the sensor of the '939 application is typically used with a cable hub having decoupling circuitry as described above and as shown in the '775 application. Counterintuitively, these slits from the sensor of the '939 application can be closed (or may be nonexistent) as shown in the coupler 602*a* of FIG. 6B to electrically decouple the patient's skin from the piezoelectric sensor, circuit board, and the like, as the coupler 602*a* can be made of a dielectric material. Accordingly, the bulky cable hub with decoupling circuitry (including bulky transformers) can be replaced with the slimmer dual sensor cable 130 described above with respect to FIGS. 1D and 1E. In an embodiment, the entire patient-contacting surface (e.g., bottom surface 699) of the acoustic sensor 600*a* may be made of a nonconductive material or may otherwise insulate or decouple the patient's skin from electrical components within the sensor.

Advantageously, in certain embodiments, the bottom surface 699 and sides 611, 613 of the coupler 602*a* are substantially enclosed and thereby provide patient isolation or decoupling from electrical components without significantly impacting SNR in the sensor 600*a*. In fact, in some tests, at least a portion of the audio range of the sensor 600*a* has an improved SNR using the coupler 602*a* over the coupler of the '939 application. In certain embodiments, this improvement stems at least in part from including air vent holes 607 in two (or optionally more) of the sides 613 of the coupler 602*a*. Corresponding pressure equalization pathways 650, described in greater detail below, are included in the frame 606. In certain embodiments, the air vent holes 607 and pressure equalization pathways 650, together with the substantially enclosing shape of the coupler 602*a*, cause the acoustic chamber formed by the coupler 602*a* and the frame 606 to act as a Helmholtz resonator or approximately as a Helmholtz resonator, thereby advantageously improving the resonance of certain frequencies in the chamber and thereby increasing SNR.

Figure 14:
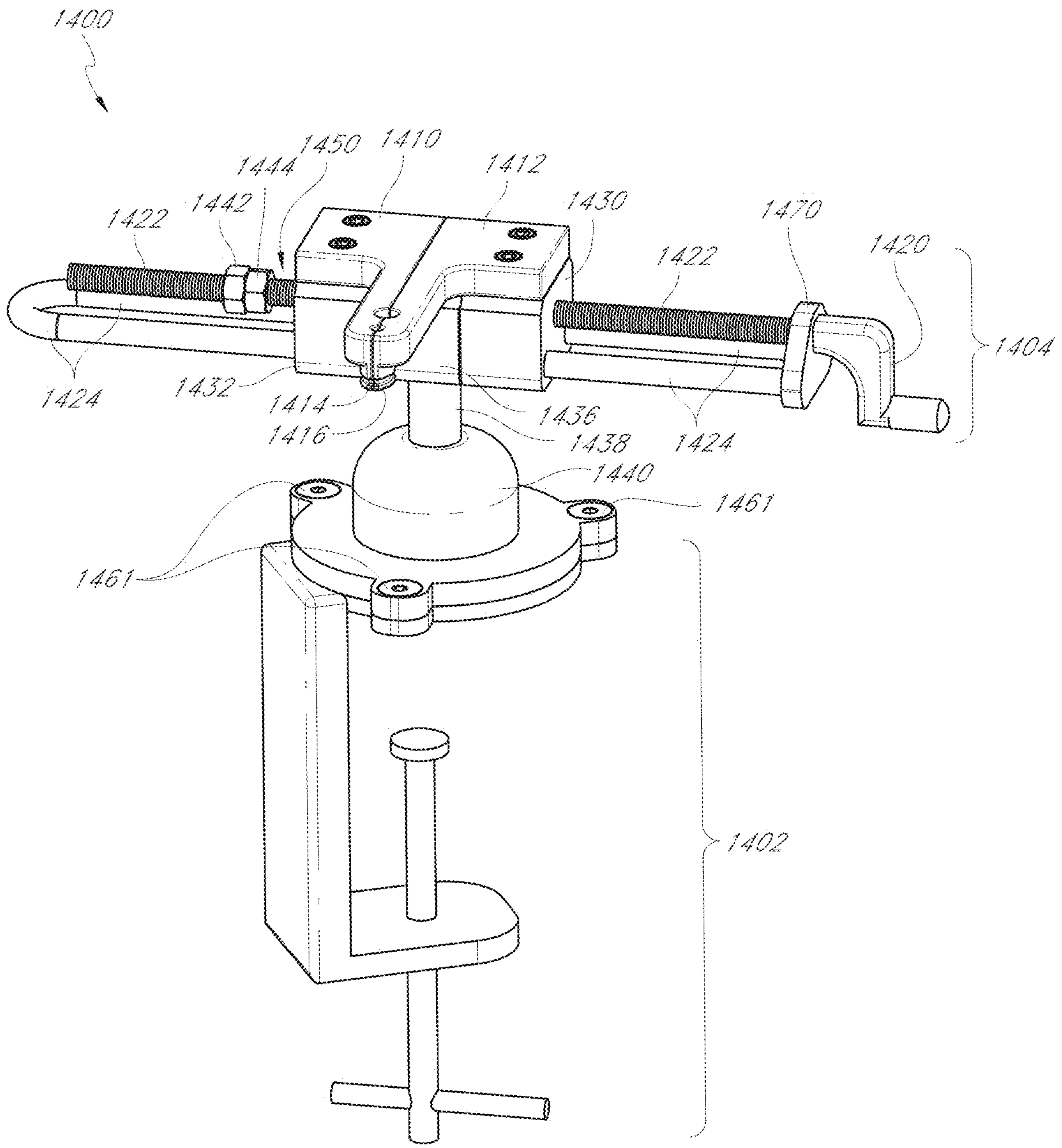
FIG. 14 is a perspective view of an embodiment of a stretching tool for stretching a coupler over a support frame of the sensor.
Figure 15A:
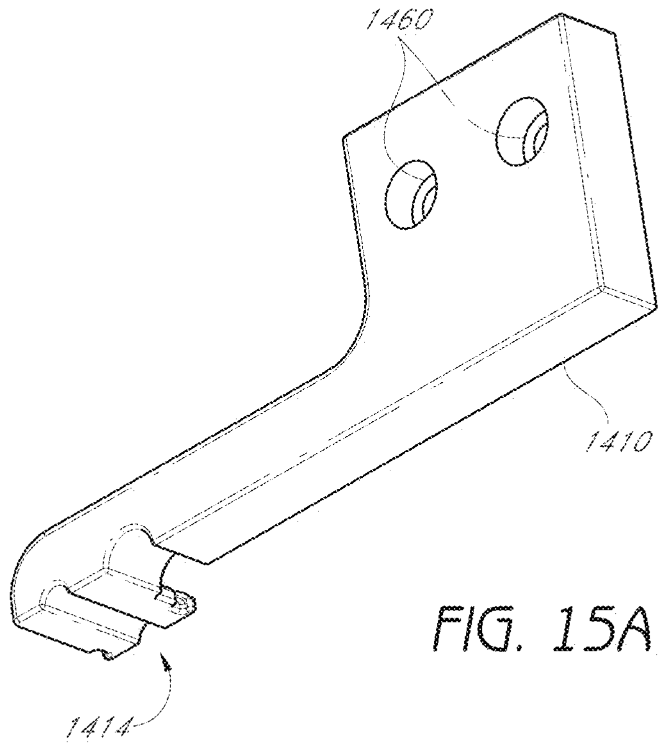
FIGS. 15A and 15B depict perspective views of a jaw of the stretching tool of FIG. 14.
Figure 15B:
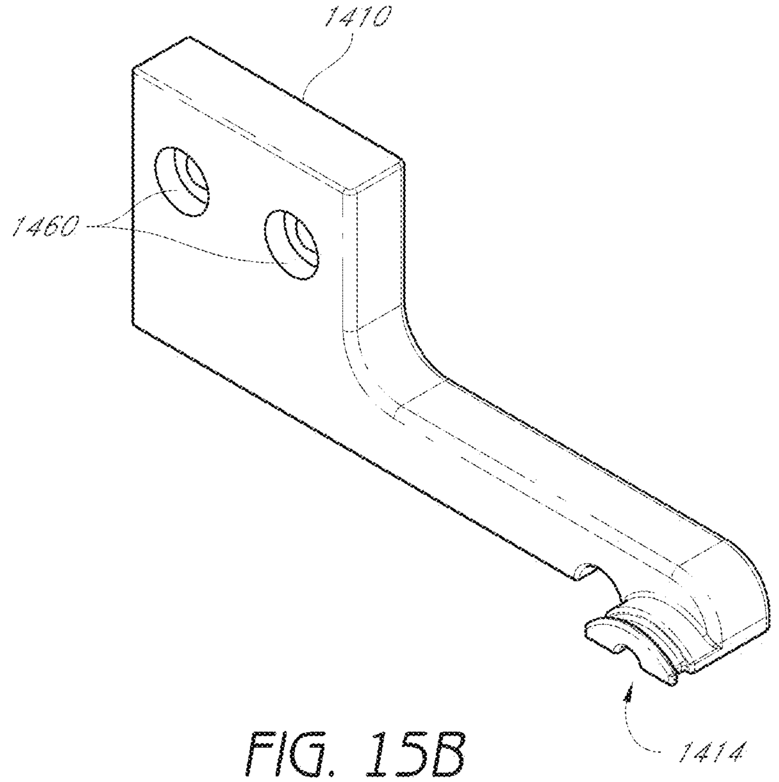

In certain embodiments, the acoustic coupler 602*a* is made of a silicone material that is flexible and can be stretched over the frame (see FIG. 14). The silicone material can also have desirable signal transmission properties that improve SNR over other materials in some embodiments.

The components of the sensor 600*a* can be assembled similarly to the sensor 415 of FIG. 4A. For example, the first piezoelectric film 620 is wrapped around a portion of the frame 606 and extends across an acoustic cavity 614 (FIG. 6B) of the frame 606 in tension. When assembled, the adhesive portions 608, 610 are positioned between interior opposing sides of the first film 620 and corresponding sides of the sensor frame 606, thereby adhering the first film 620 in place with respect to the frame 606.

The adhesive layer 612 is wrapped around the first sensing element 621, and the second sensing element 621 is in turn wrapped around the adhesive layer 612, generally forming a piezoelectric stack. As discussed with respect to FIG. 4A, the active portions of the films 620, 621 that extend across the acoustic cavity 614 are thus generally free to move in response to received vibrations, enabling detection of a physiological signal when the sensor 600*a* is attached to the patient. In certain embodiments, the acoustic cavity 614 or a portion thereof extends all the way through the frame 606. For example, the cavity may form one or more holes in the interior portion of the frame 606.

The PCB 604 is positioned in the cavity 616 (FIG. 6A) such that the underside of the PCB 604 comes into contact with the regions 617, 618 of the second film 621 and the regions 622, 624 of the first film 620. The flap 626 of the second film 621 rests on top of the PCB 604 in the illustrated embodiment, allowing electrical coupling of the first sensing element 620 to the PCB 604 and associated circuitry.

The coupler shell 602 is generally configured to transmit vibrations received from the patient to the films 620, 621 in the piezoelectric stack. The acoustic coupler 602 can include a lower protrusion or bump 628 (FIG. 6B) configured to press against the patient's body when the acoustic sensor 600*a* is fastened into place on the patient. The acoustic coupler 602 can also include a protrusion 630 (FIG. 6A) designed to abut against the films 620, 621 and to bias them in tension across the acoustic cavity 614. The coupler shell 602 can be similar to any of the acoustic couplers described herein, such as those described below with respect to FIGS. 9A-9E, 12, and 13A-13B.

Generally, the piezoelectric films 620, 621 can be any of those described herein. In the illustrated embodiment, for example, the films 620, 621 are the piezoelectric films described in FIGS. 5A-5D having flooded electrode surfaces 632, 644, respectively, which form the outer surfaces of the piezoelectric stack. Moreover, the films 620, 621 include one or more vias or through holes extending an electrode from one surface of the film 620, 621 to a corresponding region 622, 617 on the opposing surface of the respective film 620, 621. As discussed above, this configuration enables coupling of the four electrodes (e.g., the anode and cathode for each film 620, 621) to the appropriate contacts on the underside of the PCB 222.

For example, in one embodiment, the region 618 (FIG. 6A) of the flooded cathode coating on the outer surface of the second film 621 touches one or more of the contacts 636 on the underside of the PCB 604 (FIG. 6B). Meanwhile, the through-holed region 617 (FIG. 6A) of the outer surface of the second film 621, which includes an anode coating, touches the contact 638 on the underside of the PCB 604 (FIG. 6B). Regarding the first film 620, the region 624 (FIG. 6A) of the cathode coating on the inner surface touches one or more of the contacts 640 on the underside of the PCB 604 (FIG. 6B). Meanwhile, the through-holed region 622 (FIG. 6A) of the inner surface of the first film 620, which includes an anode coating, touches one or more of the contacts 642 on the underside of the PCB 604 (FIG. 6B).

According to the above-described connection scheme, the films 620, 621 can be coupled to circuitry (not shown) residing on the PCB 222 or other system component (e.g., the hub or monitor) to provide improved SNR and/or electrical shielding. For example, the electrodes of the films 620, 621 can each be coupled to an input of an attenuation circuit (e.g., a differential amplifier) or ground (or other common potential) in the manner illustrated schematically with respect to FIG. 3B above. Specifically, although other connections schemes are possible, in one embodiment, the contact 636 on the PCB 604 couples the flooded, outer cathode of the second, exterior film 621 to ground, and the contact 642 couples the outer, flooded anode of the first, interior film 620 to ground. Moreover, the contacts 642 couple the inner, un-flooded anode of the second, exterior film 621 to a first (e.g., positive) terminal of a difference amplifier or other noise attenuation circuit. Finally, the contacts 638 couple the un-flooded, inner cathode of the first, interior film 620 to a second (e.g., negative) terminal of the difference amplifier.

The frame 606 can include one or more pressure equalization pathways 650. The pressure equalization pathways 650 provide an air communication pathway between the lower acoustic cavity 614 and ambient air pressure. The pressure equalization pathways 650 allow the sensor's membrane(s) or film(s) 621, 622 to vibrate within the cavity 614 independent of skin elasticity or the force used to attach the sensor to a patient's skin. As described above, corresponding air vent holes 607 in the coupler 602*a* can be positioned over the pressure equalization pathways 650 in the frame 606 when the frame 606 is inserted into the coupler 602*a*. (Insertion of the frame 606 into the coupler 602*a* is described in greater detail below with respect to FIG. 14).

Indeed, variability in skin elasticity or the force used to attach the acoustic sensor to the medical patient's skin can affect the volume and/or air pressure within the cavity 614 defined by the sensing elements 621, 622 and frame 606. Variability in skin elasticity or attachment force can lead to variability in cavity resonance, which can cause unwanted variability in sensor 600*a* performance. For example, an acoustic sensor 600*a* that is attached to very elastic skin may provide a different output signal than an acoustic sensor 600*a* that is attached to firmer or tighter skin. Similarly, an acoustic sensor 600*a* that is loosely attached to patient's skin may provide a different output signal than an acoustic sensor 600*a* that is tightly attached to a patient's skin.

To compensate for attachment variability, in one embodiment the acoustic sensor frame 606 includes one or more pressure equalization pathways 650. The pathways 650 provide an air-flow channel from the cavity 614 to the ambient air pressure. By equalizing pressure within the cavity 614 with ambient during sensing, variability in sensor performance may be reduced and/or eliminated. In some embodiments, the pressure equalization pathways 650 include one or more holes, notches, ports, or channels that extend from within the sensor's cavity 614 to a location in communication with ambient air pressure.

In one embodiment, the pressure equalization pathways 650 are provided on opposite sides of the frame 606 portion that defines an acoustic cavity 614. Symmetrically arranging the pressure equalization pathways 650 can further improve sensor 600*a* performance. In another embodiment the pressure equalization pathways 650 are provided in portions of the sensor frame 606 which do not contact the sensor's sensing elements, membranes, and/or films 621, 622. By preventing contact between the pressure equalization pathways 650 and the sensor's sensing membrane, sensor 600*a* performance may be further improved.

In one embodiment, the sensor frame 606 includes one, two, three, four, or five pressure equalization pathways 650 on each of two opposite sides of the sensor frame 606. In another embodiment, the sensor frame 606 includes at least one pressure equalization pathway 650 on each of its sides. In one embodiment, each pressure equalization pathway 650 is formed as a notch. A frame 606 that includes notches as its pressure equalization pathways 650 may be easier to fabricate than a frame that includes other pressure equalization pathways 650 (e.g., holes). For example, when the frame 606 is made by molding plastic, creating notches in the frame's 606 side wall requires less complicated tooling than forming holes.

Aspects of some of the components of the sensor 600*a* are described in greater detail herein with respect to other embodiments. For example, one or more of the coupling shell 602, PCB 604, frame 606, sensing elements 620, 621, adhesive layers 608, 610, 612, or portions or aspects thereof are compatible with the corresponding components shown in FIGS. 9A-13B and described in the accompanying text.

Figure 6C:
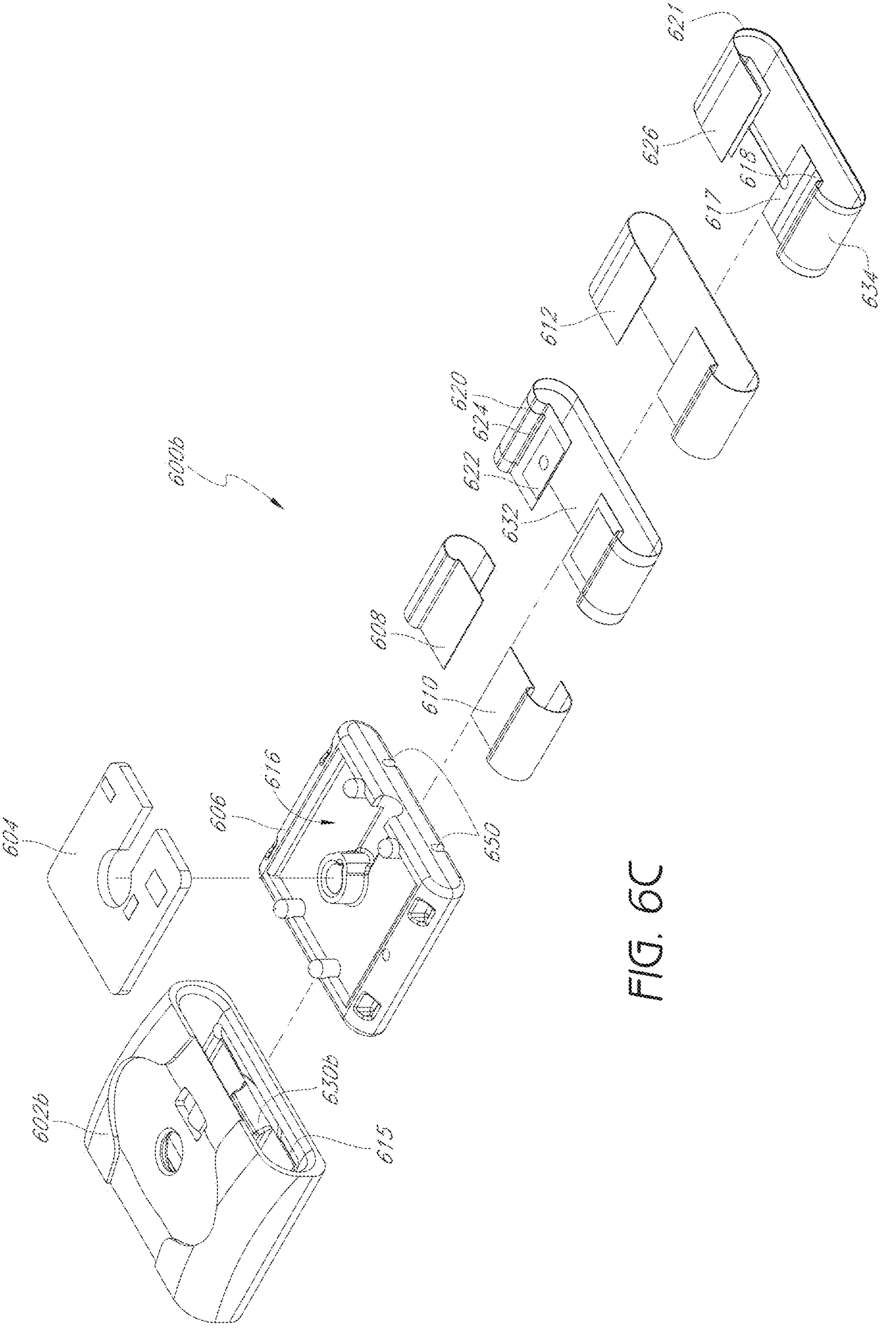
FIGS. 6C-6D are top and bottom exploded, perspective views, respectively, of a sensor incorporating another embodiment of an improved coupler in accordance with embodiments described herein.
Figure 6D:
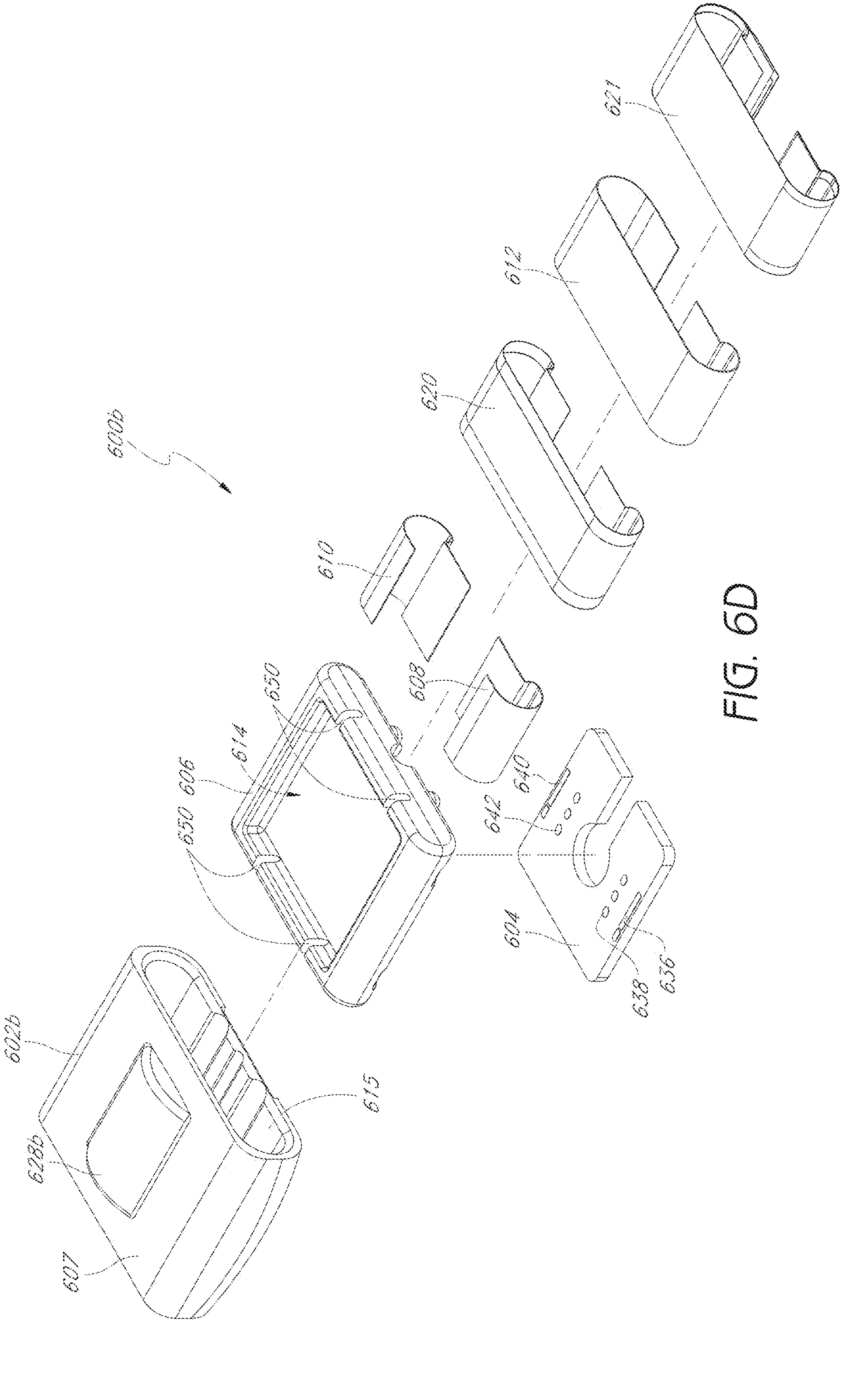

FIGS. 6C and 6D show another embodiment of a sensor 600*b*. The sensor 600*b* includes all the features of the sensor 600*a*, except that the acoustic coupler 602*b* differs in structure from the acoustic coupler 602*a*. The coupler 602*b* includes open sides 615 on two sides of the coupler 602*b*, unlike the mostly enclosed coupler 602*a*. These sides are completely open, or substantially completely open, in contrast to the smaller air vents 607 in the coupler 602*b*. More generally, the coupler 602*b* is sufficiently open on the two sides so as to allow the frame 606 to slide into the coupler 602*b*, whereas the holes in the side of the coupler 602*a* do not permit such sliding.

However, the coupler 602*b* also has an enclosed bottom surface 699, like the coupler 602*a*. Accordingly, the coupler 602*b* can also be used in place of bulky decoupling circuitry in a cable hub, as described above with respect to the coupler 602*a*. In some embodiments, the coupler 602*a* can provide greater electrical decoupling (withstanding in some implementations DC current of up to about 5 kV) than the coupler 602*b* (which can withstand in some implementations up to about 3 kV of DC current). However, both couplers 602*a*, 602*b* can advantageously protect a patient from harmful current surges due to ground loops formed in the patient between the sensor and other equipment, such as defibrillators and the like, thereby eliminating a need for a bulky cable hub when using multiple sensors in a dual sensor cable.

Noise Compensation Overview

Embodiments of systems generally including at least first and second acoustic sensing elements and configured to provide noise compensation will now be described with respect to FIGS. 7-18. As will be described, according to some aspects, one of the sensing elements is used as a physiological signal sensing element, and another is used as a noise sensing element for generating a noise reference signal. The noise reference signal can be used to generate a physiological signal have a reduced noise component according to a variety of techniques described in further detail herein (e.g., adaptive filtering techniques). Moreover, according yet other embodiments, the sensing elements are selectively configurable for use as either physiological signal sensing elements or noise sensing elements, as desired, as described in further detail herein.

According to various aspects, the multiple acoustic sensing elements can be beneficially arranged in a variety of configurations. For example, the first and second sensing elements can be incorporated into the same sensor package. In some embodiments, the first and second sensing elements are included in separate sensor packages, or can otherwise be strategically positioned at a variety of locations in the monitoring environment. For example, such sensors can be positioned at multiple locations on the patient, as is shown in and described with respect to FIG. 9A. Moreover, one or more sensing elements can be positioned at the physiological monitor or some other appropriate location in monitoring environment, as is disclosed in FIG. 9B and the accompanying text.

Generally speaking, the interfering noise signals described herein can include any acoustic signal, and can include vibrational, sonic, infrasonic, or ultrasonic waves. Such signals can be transmitted in gases, liquids and/or solids. For example, depending on the physiological signal being monitored, the interfering noise can include patient sounds generated from physiological processes, such as breathing sounds, heart sounds, digestive sounds, combinations of the same and the like. Interfering noise can further include speech sounds, snoring, coughing, gasping, etc., and can emanate from the patient or other individuals in the monitoring environment. Further sources of noise can also include humming or other acoustic noise coming from computers or other electronic equipment in the operating environment, ambient traffic or airplane noise, combinations thereof and the like.

Interfering noise can additionally emanate from one or more noisy devices that are coupled to the patient, such as medical devices that are coupled to the patient during use. Examples of such devices can include, without limitation, powered surgical equipment (e.g., electrosurgical tools for cauterizing, coagulating, welding, cutting, etc.), ventilation equipment (e.g., continuous positive airway pressure (CPAP) machines), nebulizers, combinations of the same and the like.

Particularly where a noise source is readily identifiable, the noise sensing element according to certain aspects may be positioned in physical proximity to the noise source, so as to obtain a signal including a relatively clean noise reference signal, allowing for improved noise compensation according to techniques described herein. Specific example cases are provided below with respect to FIGS. 9A-9B, for example.

According to yet other described embodiments, it can be expected that the components of their output signals resulting from one source (e.g., the patient's body) will be generally similar while signal components from other sources (e.g., noise components) can be expected to have certain dissimilarities (e.g., phase or time shift). In these cases, the output signals from the first and second acoustic sensing elements can be advantageously combined in ways that accentuate commonalities between the two signals while attenuating differences between the two output signals, or vice versa, producing a reduced noise output signal.

Moreover, while shown and described as first and second sensing elements with respect to many of the embodiments described below, there may be more than two (e.g., 3, 4, 5 or more) sensing elements in certain embodiments. Additionally, while described as individual sensing elements for the purposes of illustration, in certain embodiments one or more of the first and second sensing elements each include multiple acoustic transducers or other types of sensing elements. In some embodiments, for example, the first and/or second sensing elements each include at least two piezoelectric films arranged in a stacked configuration, wrapped around a support frame, as described above with respect to FIGS. 3B-4B and 6A-6B.

Figure 7:
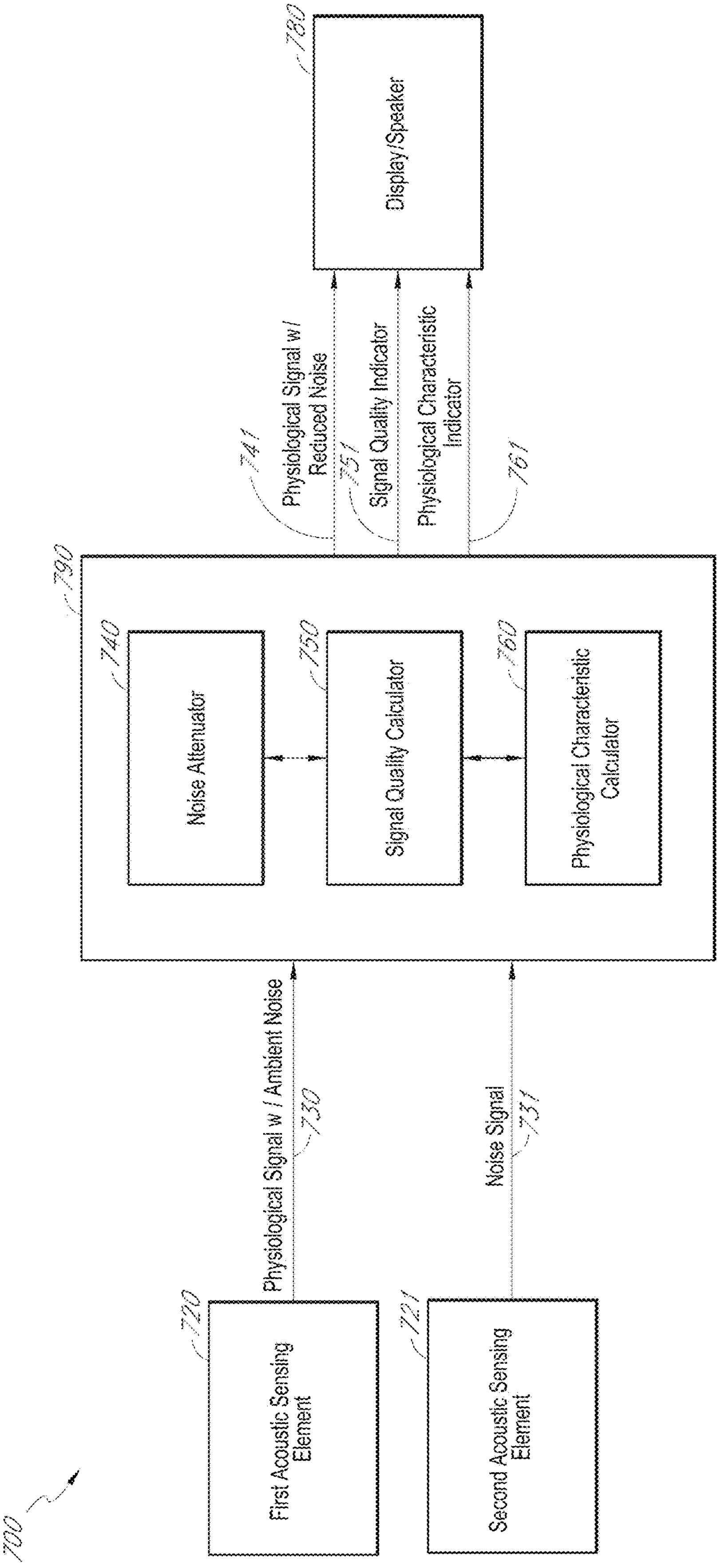
FIG. 7 is a block diagram of an example acoustic physiological monitoring system having noise compensation features.

FIG. 7 is a block diagram of an embodiment of an acoustic physiological monitoring system 700 having noise compensation features. The noise compensation features can be useful for reducing any deleterious effect of acoustic noise on the accuracy of physiological characteristics determined using the monitoring system 700.

The acoustic physiological monitoring system 700 includes a first acoustic sensing element 720 and a second acoustic sensing element 721. In some embodiments, these acoustic sensing elements are passive devices. In some embodiments, the first acoustic sensing element 720 is used to produce a physiological signal 730 that is indicative of one or more physiological sounds (e.g., sounds resulting from physiological processes) emanating from a patient's body. For example, the first acoustic sensing element 720 may be used to produce a physiological signal 730 that is indicative of a particular type of physiological sound, which is sometimes referred to herein as the target physiological sound. A variety of target physiological sounds are possible, including breathing sounds, heart sounds, digestive sounds, and the like. For example, the sensing elements 720, 721 can be piezoelectric films. In general, this physiological signal 730 can include unwanted noise as a result of interfering noise in the patient's surroundings being picked up by the first acoustic sensing element 720. The physiological component and the noise component of the signal 730 can overlap in time and/or frequency content. Devices for detecting primarily physiological sounds emanating from the patient's body are disclosed more fully herein.

In some embodiments, the second acoustic sensing element 721 is used to produce a noise signal that is substantially representative of, or otherwise meaningfully correlated with, any noise picked up by the first acoustic sensing element 720. The noise signal 731 may not necessarily duplicate the noise component of the physiological signal 730. For example, the signal strength of the noise in the two signals 730, 731 can differ. Other differences between the noise signal 731 and the noise component of the physiological signal 730 are also possible. However, it can be advantageous for the second acoustic sensing element to be positioned and designed such that the noise signal 731 has some degree of commonality with the noise present in the physiological signal 730. In this way, the noise signal 731 can provide useful information to meaningfully reduce, remove, filter, cancel, separate out, etc. the noise from the physiological signal 730. Devices for detecting primarily noise sounds are disclosed more fully herein.

In addition, the second acoustic sensing element 721 can also be positioned and designed such that the noise signal 731 is substantially free of the physiological sounds picked up by the first acoustic sensing element 720, or such that such physiological sounds are a less-significant component of the noise signal 731 than they are of the physiological signal 730. While illustrated as producing a noise signal 731, in other embodiments discussed more fully herein the second acoustic sensing element is positioned and designed to provide a second physiological signal rather than a noise reference signal. For example, like the first sensing element 720, the second acoustic sensing element 721 may include both a significant physiological signal component and an interfering noise component. In such embodiments, the first and second physiological signals can be combined in certain ways so as to reinforce the physiological components of the two signals while reducing any noise components that can exist in the two physiological components. In other embodiments, this can be carried out using more than two acoustic sensing elements.

In some embodiments, the physiological signal mixed with noise 730 and the noise signal 731 are input to a processing unit 790. In some embodiments, the processing unit 790 includes a noise attenuator 740, a signal quality calculator 750, and a physiological characteristic calculator 760. The processing unit 790 can be implemented as one or more digital signal processors, one or more analog electric processing components, combinations of the same or the like, etc.

In some embodiments, the noise attenuator 740 reduces the amount of noise present in the physiological signal 730 based on information gleaned from the noise signal 731, as discussed in more detail herein. For example, the noise attenuator 740 can reduce the signal energy of the noise component of the physiological signal 730. Alternatively, or in addition, the noise attenuator 740 can reduce or remove a portion of the noise component of the physiological signal 730 over a particular frequency range. In some embodiments, the processing unit 790 outputs a physiological signal with reduced noise 741 using the noise attenuator 740. The signal 741 can also be provided to other sub-blocks of the processing unit 790 (e.g., the physiological characteristic calculator 760).

The signal quality calculator 750 is a device that is used to determine, for example, an objective indicator of the quality of the physiological information obtained from one or more acoustic sensing elements. This can be done, for example, by comparing the physiological signal 730 with the noise signal 731, as discussed further herein. The signal quality calculator 750 can also output an objective indicator of the degree of confidence in the accuracy of a physiological characteristic (e.g., respiratory rate) determined based on the physiological information collected from one or more acoustic sensors. The signal quality calculator 750 can also output a binary confidence indicator that selectively indicates low confidence and/or high confidence in the accuracy of the physiological characteristic. The processing unit 790 then outputs one or more signal quality indicators 751.

The physiological characteristic calculator 760 is used to determine, for example, one or more values or signals that are indicative of a physiological characteristic of the patient. For example, the physiological characteristic can be respiratory rate, expiratory flow, tidal volume, minute volume, apnea duration, breath sounds, riles, ronchi, stridor, and changes in breath sounds such as decreased volume or change in airflow. In some embodiments, a physiological characteristic is calculated using a processing algorithm applied to the physiological signal with reduced noise 741 that is outputted by the noise attenuator 740.

The physiological signal with reduced noise 741, the signal quality indicator 751, and the physiological characteristic indicator can be output to a display and/or speaker 780 to be viewed or heard by a caregiver. For example, in some embodiments, the physiological signal with reduced noise 741 is converted back to an audible sound by way of a speaker or other acoustic transducer so that it can be heard by a doctor and used for diagnosis of the patient. In some embodiments, the signal quality indicator 751 and the physiological characteristic indicator 761 are displayed on a screen. This information can take the form of a numerical value, a plotted signal, an icon, etc.

Although both the noise attenuator 740 and the signal quality calculator 750 are included in the example processing unit 790 shown, the processing unit 790 could include either the noise attenuator 740 or the signal quality calculator 750 in some embodiments.

In various embodiments, the first and second acoustic sensing elements 720, 721 can be either the same or different types of acoustic sensing elements. For example, in one embodiment, both of the sensing elements are piezoelectric films such as any of the films described herein. In such a configuration, each of the sensing elements 720, 721 may be housed in a separate sensor packaging. As an example where different types of sensing elements are used, the first sensing element 720 in one embodiment is a piezoelectric film, while the second sensing element is a microphone, vibrational sensor or other type of acoustic pickup device.

Additionally, the sensing elements 720, 721 may be physically separate from one another. For example, the sensing elements 720, 721 can be physically separated within a single wearable sensor package. In other embodiments, the first sensing element 720 may be located on a wearable sensor package, such as any of those described herein, while the second sensing element 721 may be located at some other location, such as, for example, on a cable, hub, monitor, or in another wearable sensor package at a different location on the patient, etc.

While embodiments described herein advantageously employ multiple sensing elements to achieve noise compensation, in certain embodiments, noise compensation is achieved using a single sensing element. For example, the sensing element may be coupled to the patient and thus produce a signal including both physiological and noise components. However, in such embodiments, the noise reference signal may be extracted during periods when the physiological signal is inactive (e.g., in between patient breaths, heart beats, etc.). The extracted reference signal can then be used in accordance with techniques described herein to provide noise compensation.

Figure 8:
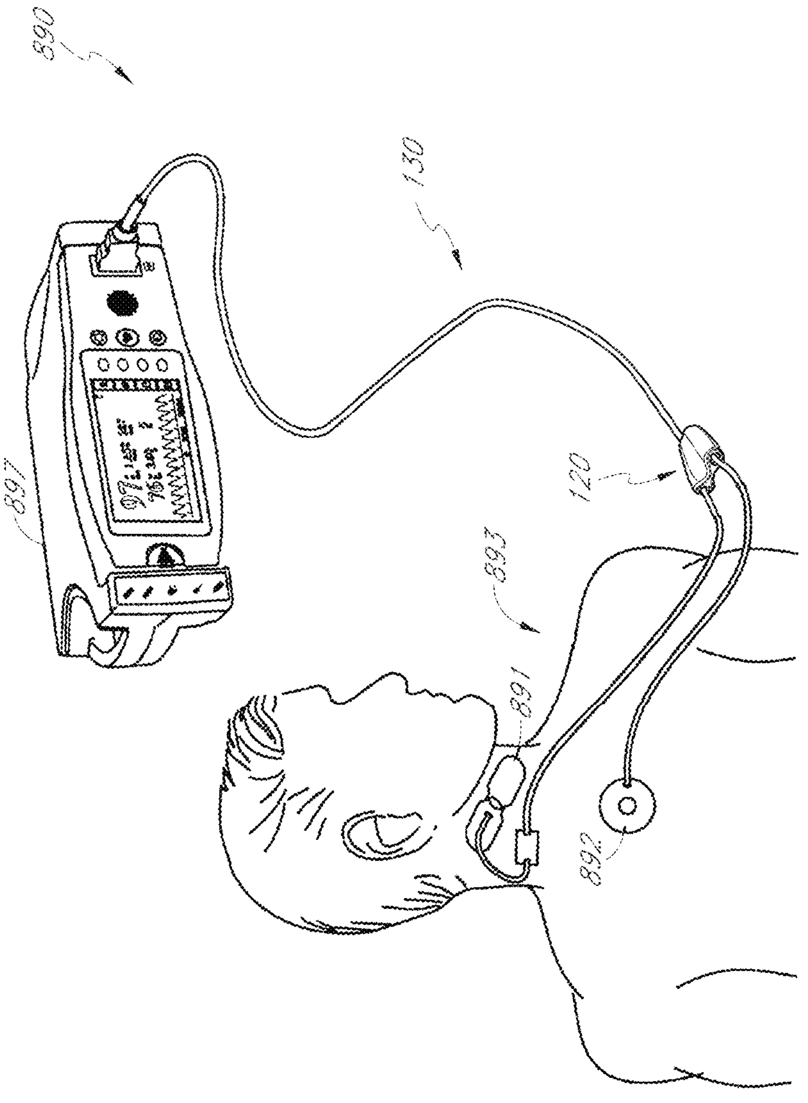
FIG. 8 is a block diagram of an embodiment of an acoustic physiological monitoring system with a multi-sensor cable.

FIG. 8 illustrates an example system 890 including dual acoustic sensors 891, 892 applied to a patient's 893 throat and chest, respectively. The system 890 of FIG. 8 depicts one example embodiment where the dual sensor cable 130 can connect to multiple sensors using the junction 120.

Electromagnetic Interference (EMI) Compensation

In some embodiments, the physiological monitoring systems and patient sensors described herein include electromagnetic interference compensation features. The electromagnetic interference compensation features can be useful for reducing any deleterious effect of EMI on the accuracy of physiological characteristics determined using the monitoring systems. One possible source of such EMI could be, for example, 50-60 Hz RF waves generated by the electric power distribution system in a patient care facility.

In some embodiments, the physiological monitoring systems include an electrical conductor for detecting an EMI reference signal that is indicative of EMI that may have corrupted electrical signals used by the physiological monitoring systems (e.g., a physiological signal generated by an acoustic sensing element). The EMI reference signal detector can be, for example, a dedicated antenna that is positioned at a location where the EMI that it detects is in some way representative of, or meaningfully correlated with, the EMI to which an electrical signal within the patient sensor is exposed. The EMI reference signal detector can be located, for example, on or in one or more wearable patient sensors (e.g., 215, 815, 915, etc.), though it may also be located in a separate physiological monitor unit, intermediate location (e.g., cable, connector or hub), at any location described above with respect to acoustic noise reference sensing elements, or at some other location.

In some embodiments, the EMI reference signal detector is a conductive plate or wire, or some other conductive structure. In some embodiments, the EMI reference signal detector is left electrically floating. While in some embodiments, the EMI reference signal detector is a dedicated component, in other embodiments other existing components of, for example, a patient sensor described herein can be used as the EMI reference signal detector. For example, one or more electrical shielding layers (e.g., 226, 228) in a patient sensor can be used to detect EMI and to generate an EMI reference signal. Generally, according to certain aspects, any of the shielding barriers described herein (e.g., with respect to FIGS. 2B-E, 5A-B, etc.) can be used to detect EMI and generate an EMI reference signal.

In some embodiments, the EMI reference signal generated by the EMI reference signal detector is transmitted to a noise attenuator or other sensing circuitry. The noise attenuator can also be communicatively coupled to, for example, one or more physiological electrical signals output from the acoustic sensing elements described herein. Such physiological electrical signals can be corrupted by any EMI to which they are exposed.

The noise attenuator or other sensing circuitry reduces or removes the EMI component from the physiological signal based on information regarding the EMI that is gleaned from the EMI reference signal. The noise attenuator or other sensing circuitry can use any of numerous methods and components for reducing, removing, filtering, canceling, subtracting, or separating out EMI in a signal based on the EMI reference signal, or combinations of the same or the like. For example, the noise attenuator may be an adaptive noise filter or an adaptive noise canceler. The noise attenuator can perform time domain and/or frequency domain operations. The noise attenuator can include time shift modules, phase shift modules, scalar and/or complex multiplier modules, filter modules, etc., each of which can be implemented using, for example, hardware (e.g., electrical components, FPGAs, ASICs, general-purpose digital signal processors, etc.) or a combination of hardware and software.

In some embodiments, the noise attenuator or other sensing circuitry includes a self-adjusting component whose effect on the physiological signal corrupted by EMI continuously varies in response to information derived from the EMI reference signal. For example, the self-adjusting component can be an adaptive filter whose transfer function, or some other characteristic, is iteratively updated based on analysis of the EMI reference signal. The adaptive filter can be implemented, for example, using a digital signal processor with iteratively updated filter coefficients. Other methods of implementing the adaptive filter can also be used. Filter coefficients can be updated using, for example, a least mean squares algorithm (LMS), or a least squares algorithm, a recursive least squares algorithm (RLS). The noise attenuator can also use, for example, a Kalman filter, a joint process estimator, an adaptive joint process estimator, a least-squares lattice joint process estimator, a least-squares lattice predictor, a noise canceler, a correlation canceler, optimized time or frequency domain implementations of any of the above, combinations of the same, and the like.

Additional Sensor Embodiments

FIGS. 9A through 9F illustrate additional embodiments of a sensor. The sensor is shown with an acoustic coupler similar to the acoustic coupler 602*b* of FIGS. 6C and 6D. However, the acoustic coupler 602*a* of FIGS. 6A and 6B can be used in place of the acoustic coupler 602*b* in any of the embodiments described herein.

Figure 9A:
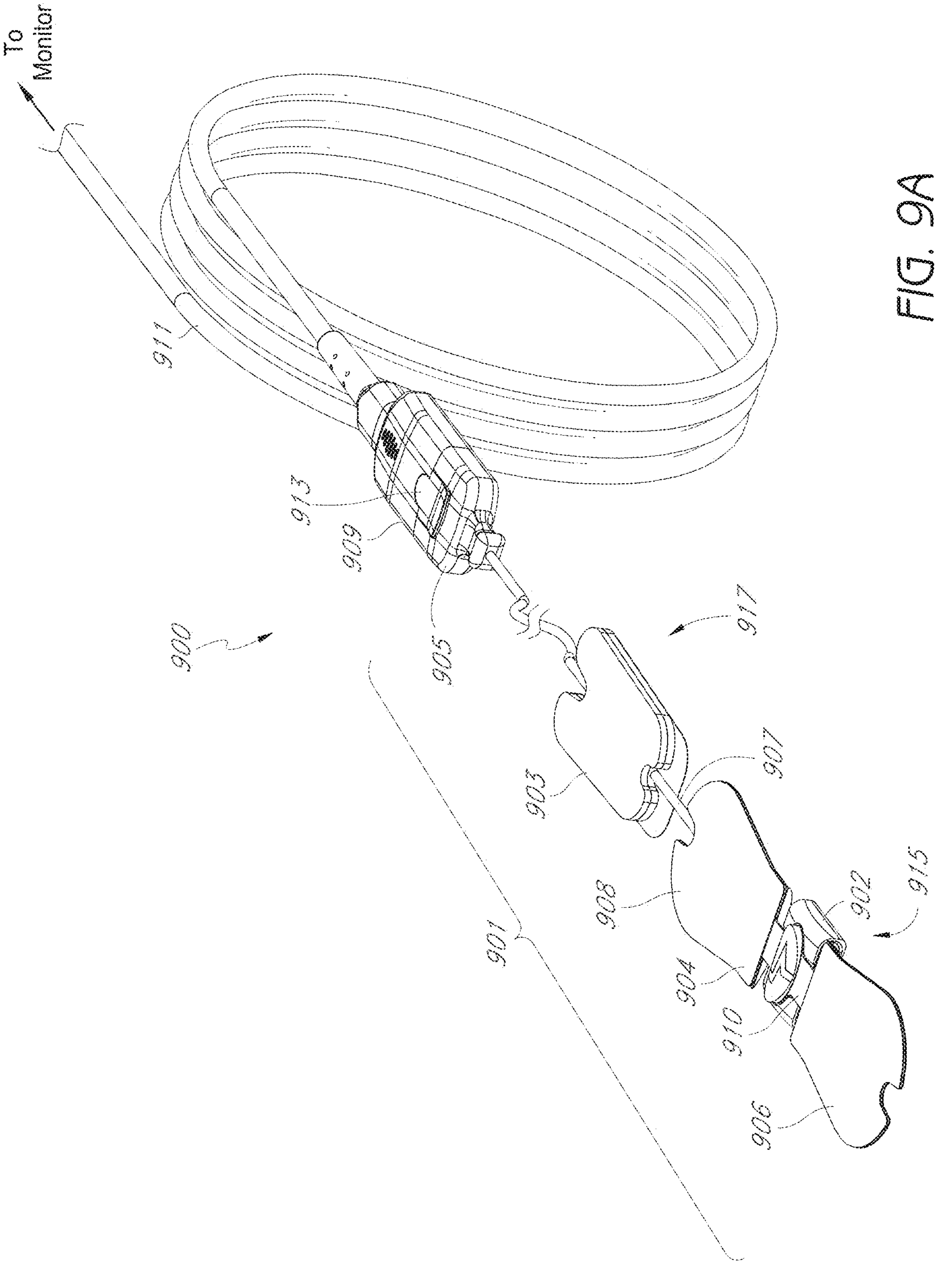
FIG. 9A is a top perspective view illustrating portions of a sensor assembly in accordance with an embodiment of the disclosure.

FIG. 9A is a top perspective of a sensor system 900 including a sensor assembly 901 suitable for use with any of the physiological monitors shown in FIGS. 1A-C and a monitor cable 911. The sensor assembly 901 includes a sensor 915, a cable assembly 917 and a connector 905. The sensor 915, in one embodiment, includes a sensor subassembly 902 and an attachment subassembly 904. The cable assembly 917 of one embodiment includes a cable 907 and a patient anchor 903. The various components are connected to one another via the sensor cable 907. The sensor connector subassembly 905 can be removably attached to monitor connector 909 which is connected to physiological monitor (not shown) through the monitor cable 911. In one embodiment, the sensor assembly 901 communicates with the physiological monitor wirelessly. In various embodiments, not all of the components illustrated in FIG. 9A are included in the sensor system 900. For example, in various embodiments, one or more of the patient anchor 903 and the attachment subassembly 904 are not included. In one embodiment, for example, a bandage or tape is used instead of the attachment subassembly 904 to attach the sensor subassembly 902 to the measurement site. Moreover, such bandages or tapes may be a variety of different shapes including generally elongate, circular and oval, for example.

The sensor connector subassembly 905 and monitor connector 909 may be advantageously configured to allow the sensor connector 905 to be straightforwardly and efficiently joined with and detached from the monitor connector 909. Embodiments of sensor and monitor connectors having similar connection mechanisms are described in U.S. patent application Ser. No. 12/248,856 (hereinafter referred to as "the '856 application"), filed on Oct. 9, 2008, which is incorporated in its entirety by reference herein. For example, the sensor connector 905 includes a mating feature 913 which mates with a corresponding feature (not shown) on the monitor connector 909. The mating feature 905 may include a protrusion which engages in a snap fit with a recess on the monitor connector 909. In certain embodiments, the sensor connector 905 can be detached via one hand operation, for example. Examples of connection mechanisms may be found specifically in paragraphs [0042], [0050], [0051], [0061]-[0068] and [0079], and with respect to FIGS. 8A-F, 13A-E, 19A-F, 23A-D and 24A-C of the '856 application, for example. The sensor system 900 measures one or more physiological parameters of the patient, such as one of the physiological parameters described above.

The sensor connector subassembly 905 and monitor connector 909 may advantageously reduce the amount of unshielded area in and generally provide enhanced shielding of the electrical connection between the sensor and monitor in certain embodiments. Examples of such shielding mechanisms are disclosed in the '856 application in paragraphs [0043]-[0053], [0060] and with respect to FIGS. 9A-C, 11A-E, 13A-E, 14A-B, 15A-C, and 16A-E, for example.

As will be described in greater detail herein, in an embodiment, the acoustic sensor assembly 901 includes a sensing element, such as, for example, a piezoelectric device or other acoustic sensing device. The sensing element generates a voltage that is responsive to vibrations generated by the patient, and the sensor includes circuitry to transmit the voltage generated by the sensing element to a processor for processing. In an embodiment, the acoustic sensor assembly 901 includes circuitry for detecting and transmitting information related to biological sounds to a physiological monitor. These biological sounds may include heart, breathing, and/or digestive system sounds, in addition to many other physiological phenomena. The acoustic sensor 915 in certain embodiments is a biological sound sensor, such as the sensors described herein. In some embodiments, the biological sound sensor is one of the sensors such as those described in the '883 application. In other embodiments, the acoustic sensor 915 is a biological sound sensor such as those described in U.S. Pat. No. 6,661,161, which is incorporated by reference herein. Other embodiments include other suitable acoustic sensors.

The attachment sub-assembly 904 includes first and second elongate portions 906, 908. The first and second elongate portions 906, 908 can include patient adhesive (e.g., in some embodiments, tape, glue, a suction device, etc.) attached to a elongate member 910. The adhesive on the elongate portions 906, 908 can be used to secure the sensor subassembly 902 to a patient's skin. As will be discussed in greater detail herein, the elongate member 910 can beneficially bias the sensor subassembly 902 in tension against the patient's skin and reduce stress on the connection between the patient adhesive and the skin. A removable backing can be provided with the patient adhesive to protect the adhesive surface prior to affixing to a patient's skin.

The sensor cable 907 is electrically coupled to the sensor subassembly 902 via a printed circuit board ("PCB") (not shown) in the sensor subassembly 902. Through this contact, electrical signals are communicated from the multi-parameter sensor subassembly to the physiological monitor through the sensor cable 907 and the cable 911.

Figure 9B:
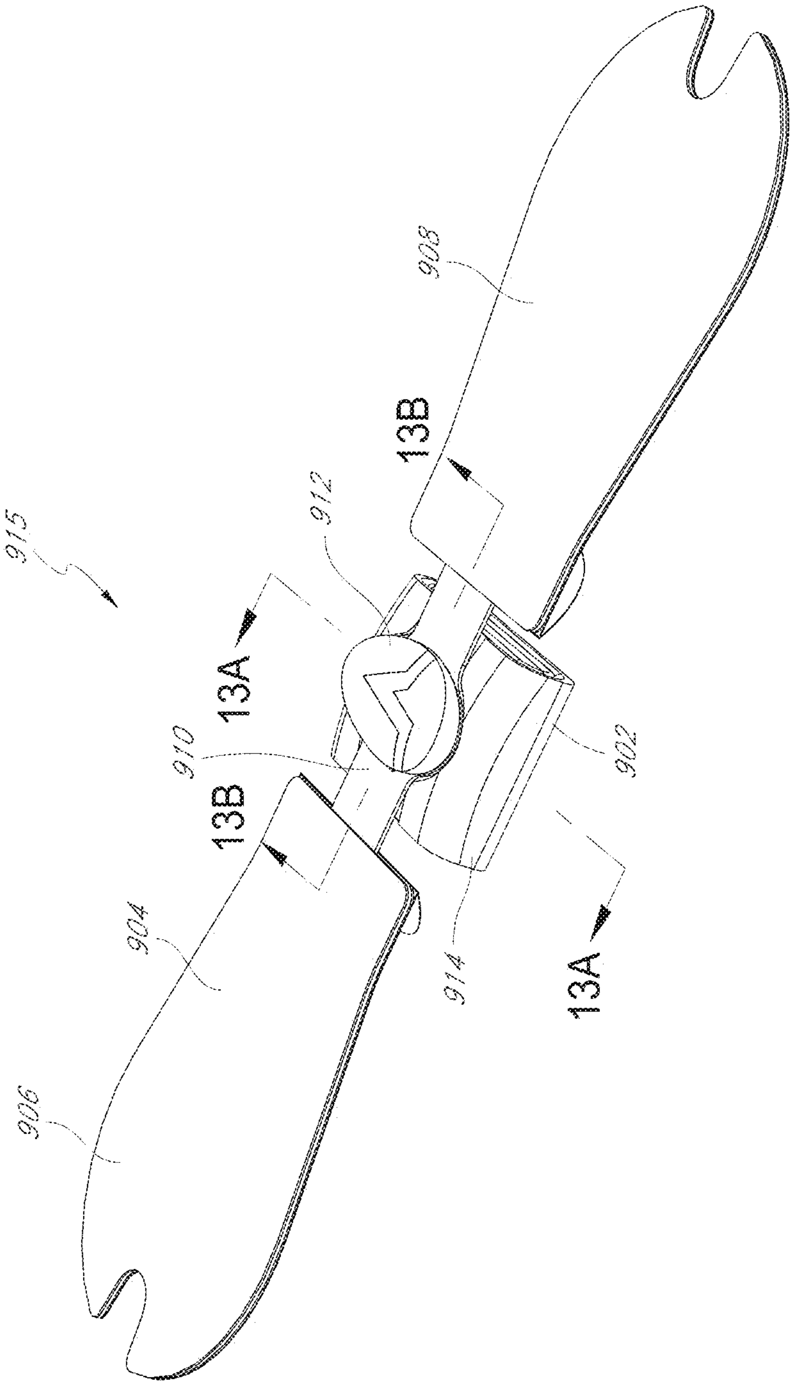
FIGS. 9B-9C are top and bottom perspective views, respectively, of a sensor including a sensor subassembly and an attachment subassembly of FIG. 9A.
Figure 9C:
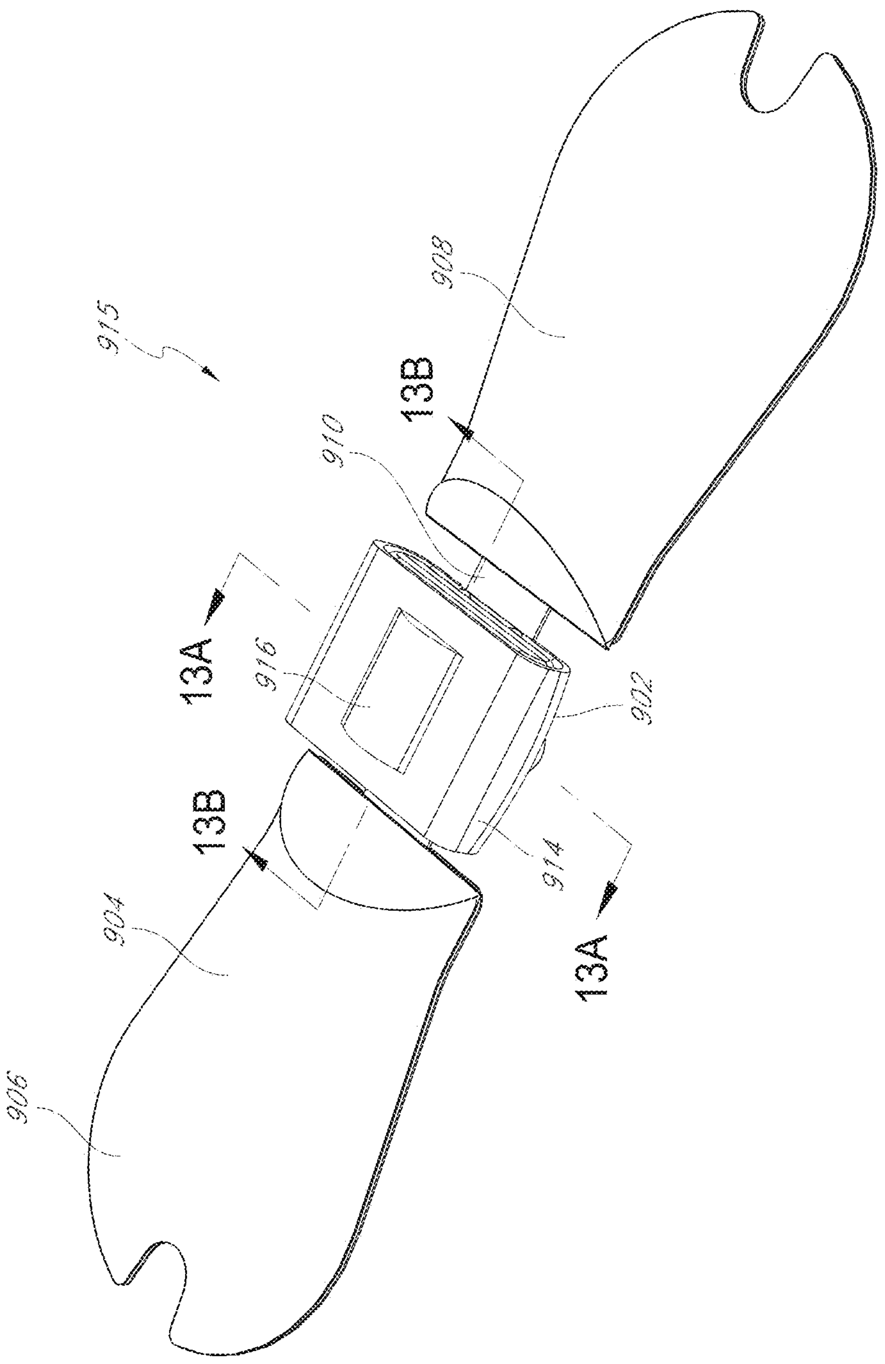

FIGS. 9B-9C are top and bottom perspective views of a sensor including subassembly 902 and an attachment subassembly 904 in accordance with an embodiment of the present disclosure. The attachment subassembly 904 generally includes lateral extensions symmetrically placed about the sensor subassembly 902. For example, the attachment subassembly 904 can include single, dual or multiple wing-like extensions or arms that extend from the sensor subassembly 902. In other embodiments, the attachment subassembly 902 has a circular or rounded shape, which advantageously allows uniform adhesion of the attachment subassembly 904 to an acoustic measurement site. The attachment subassembly 904 can include plastic, metal or any resilient material, including a spring or other material biased to retain its shape when bent. In the illustrated embodiment, the attachment subassembly 904 includes a first elongate portion 906, a second elongate portion 908, an elongate member 910 and a button 912. As will be discussed, in certain embodiments the attachment subassembly 904 or portions thereof are disposable and/or removably attachable from the sensor subassembly 902. The button 910 mechanically couples the attachment subassembly 904 to the sensor subassembly 902. The attachment subassembly 904 is described in greater detail below with respect to FIGS. 9A-9D. The attachment subassembly 904 may also be referred to as an attachment element herein.

In one embodiment, the sensor subassembly 902 is configured to be attached to a patient and includes a sensing element configured to detect bodily sounds from a patient measurement site. The sensing element may include a piezoelectric membrane, for example, and is supported by a support structure such as a generally rectangular support frame 918. The piezoelectric membrane is configured to move on the frame in response to acoustic vibrations, thereby generating electrical signals indicative of the bodily sounds of the patient. An electrical shielding barrier (not shown) may be included which conforms to the contours and movements of the piezoelectric element during use. In the illustrated embodiment, additional layers are provided to help adhere the piezoelectric membrane to the electrical shielding barrier 927. Embodiments of the electrical shielding barrier are described in greater detail below.

Embodiments of the sensor subassembly 902 also include an acoustic coupler 914, which advantageously improves the coupling between the source of the signal to be measured by the sensor (e.g., the patient's skin) and the sensing element. The acoustic coupler 914 of one embodiment includes a bump positioned to apply pressure to the sensing element so as to bias the sensing element in tension. The acoustic coupler 914 can also provide electrical isolation between the patient and the electrical components of the sensor, beneficially preventing potentially harmful electrical pathways or ground loops from forming and affecting the patient or the sensor.

The sensor subassembly 902 of the illustrated embodiment includes an acoustic coupler 914 which generally envelops or at least partially covers some or all of the components of the sensor subassembly 902. Referring to FIG. 9C, the bottom of the acoustic coupler 914 includes a contact portion 916 which is brought into contact with the skin of the patient. Embodiments of acoustic couplers are described in greater detail below.

Figure 9D:
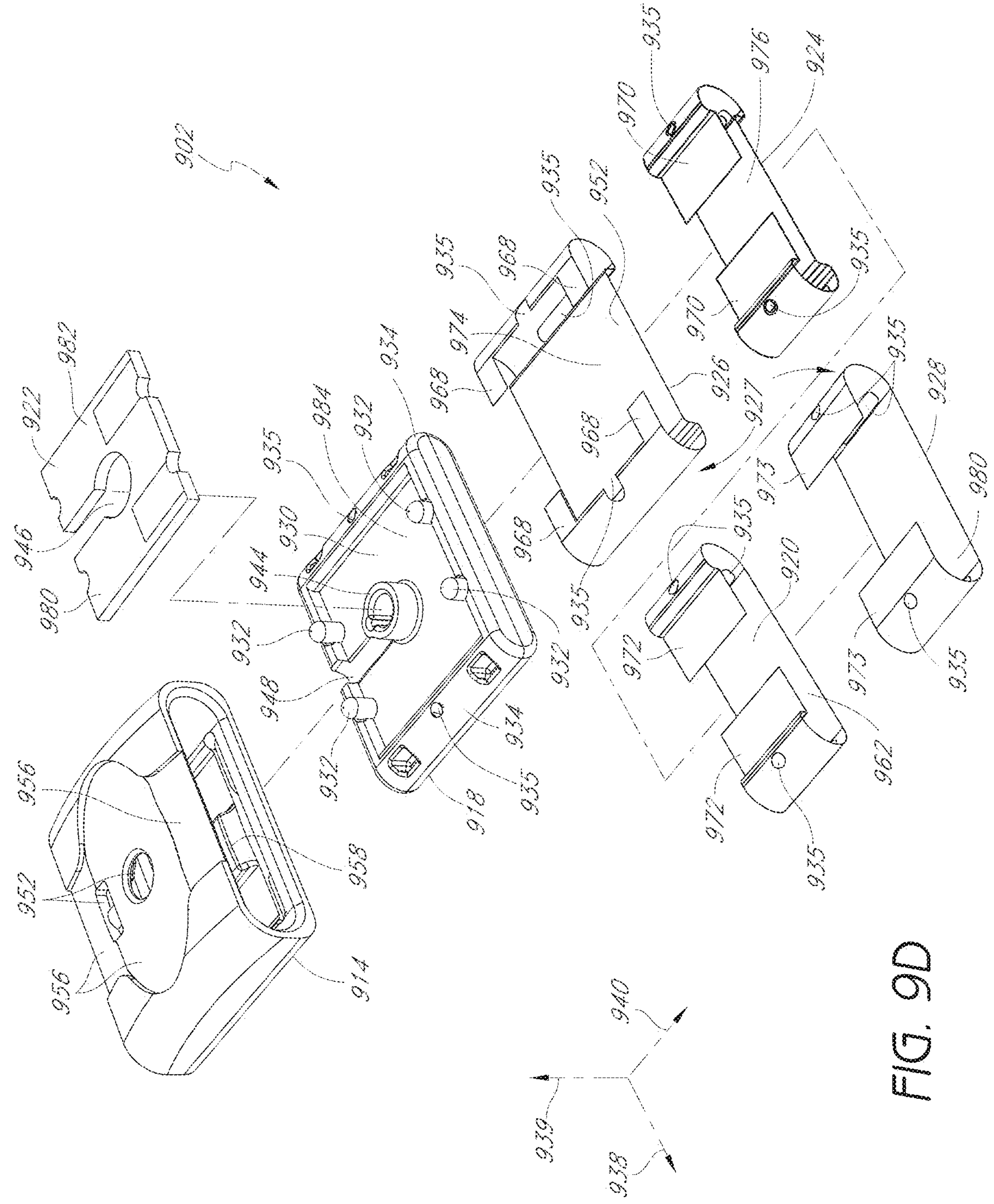
FIGS. 9D-9E are top and bottom exploded, perspective views, respectively, of the sensor subassembly of FIGS. 9A-9C.
Figure 9E:
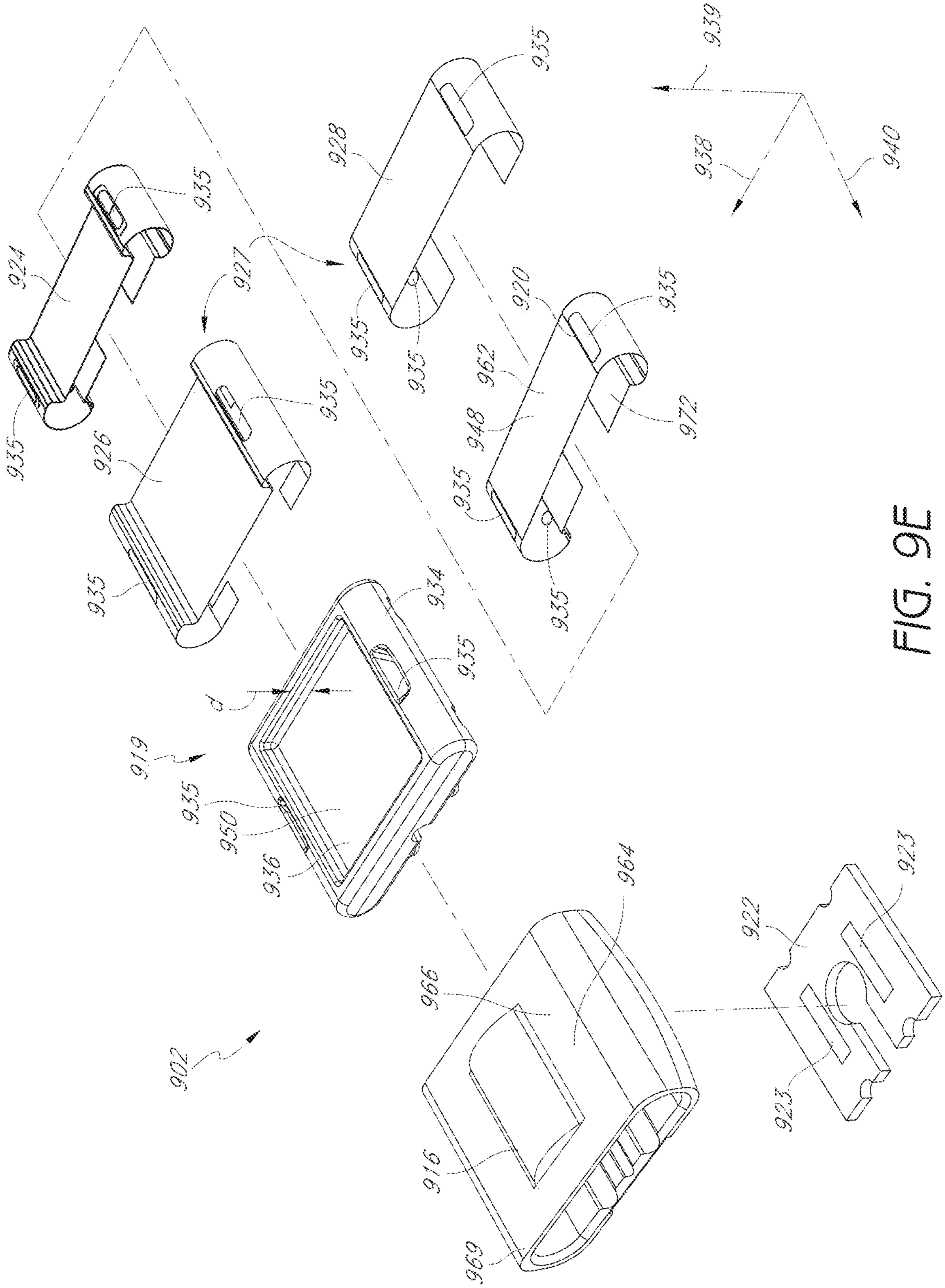

FIGS. 9D-9E are top and bottom exploded, perspective views, respectively, of the sensor subassembly 902 of FIGS. 9A-C.

Support Frame

The frame generally supports the various components of the sensor. For example, the piezoelectric element, electrical shielding barrier, attachment element and other components may be attached to the frame. The frame can be configured to hold the various components in place with respect to the frame and with respect to one another, thereby beneficially providing continuous operation of the sensor under a variety of conditions, such as during movement of the sensor. For example, the frame can be configured to hold one or more of the components together with a predetermined force. Moreover, the frame can include one or more features which can improve the operation of the sensor. For example, the frame can include one or more cavities which allow for the piezoelectric element to move freely and/or which amplify acoustic vibrations from bodily sounds of the patient.

In the illustrated embodiment, a PCB 922 is mounted on the frame 918. The frame 918 supports a series of layers which are generally wrapped around the underside 942 of the frame 918 and include, from innermost to outermost, an inner shield layer 926, an bonding layer 924, a sensing element 920 and an outer shield layer 928.

As shown in FIG. 9D, the support frame 918 has a generally rectangular shape, as viewed from the top or bottom, although the frame shape could be any shape, including square, oval, elliptical, elongated, etc. In various embodiments, the frame 918 has a length of from between about 5 and 50 millimeters. In one embodiment, the frame 918 has a length of about 17 millimeters. The relatively small size of the frame 918 can allow the sensor subassembly 902 to be attached comfortably to contoured, generally curved portions of the patient's body. For, example, the sensor subassembly 902 can be comfortably attached to portions of the patient's neck whereas a larger frame 918 may be awkwardly situated on the patient's neck or other contoured portion of the patient. The size of the frame 918 may allow for the sensor subassembly 902 to be attached to the patient in a manner allowing for improved sensor operation. For example, the relatively small frame 918, corresponding to a relatively smaller patient contact area, allows for the sensor subassembly 902 to be applied with substantially uniform pressure across the patient contact area.

The frame 918 is configured to hold the various components in place with respect to the frame. For example, in one embodiment, the frame 918 includes at least one locking post 932, which is used to lock the PCB 922 into the sensor sub-assembly 902, as described below. In the illustrated embodiment, the frame 918 includes four locking posts 932, for example, near each of the 918 four corners of the frame 918. In other embodiments, the frame 918 includes one, two, or three locking posts 918. When the locking posts 932 are brought into contact with horns of an ultrasonic welder or a heat source, they liquefy and flow to expand over the material beneath it and then harden in the expanded state when the welder is removed. When the components of the sensor sub-assembly 902 are in place, the locking posts 932 are flowed to lock all components into a fixed position.

In one embodiment, the locking posts 932 are formed from the same material as, and are integral with the frame 918. In other embodiments, the locking posts 932 are not formed from the same material as the frame 918. For example, in other embodiments, the locking posts 932 include clips, welds, adhesives, and/or other locks to hold the components of the sensor sub-assembly 902 in place when the locking posts 932 are locked into place.

With further reference to FIGS. 9E, in an assembled configuration, the PCB 922 sits inside of an upper cavity 930 of the frame 918 and is pressed against the sensing element 920 to create a stable electrical contact between the PCB 922 and electrical contact portions of the sensing element 920. For example, in certain embodiments, the expanded locking posts 932 press downward on the PCB 922 against the sensing element 920, which is positioned between the PCB 922 and the frame 918. In this manner, a stable and sufficient contact force between the PCB 922 and the sensing element 920 is maintained. For example, as the sensor assembly 900 moves due to acoustic vibrations coming from the patient or due to other movements of the patient, the electrical contact between the PCB 922 and the sensing element 920 remains stable, constant, uninterrupted, and/or unchanged.

In another embodiment, the sensing element 920 may be positioned over the PCB 922 between the expanded locking posts 932 and the PCB 922. In certain embodiments, the contact force between the PCB 922 and the sensing element 920 is from between about 0.5 pounds and about 10 pounds. In other embodiments, the contact force is between about 1 pound and about 3 pounds. In one embodiment, the contact force between the PCB 922 and the sensing element 920 is at least about 2 pounds. The bonding layer 924 is positioned between the frame 918 and the sensing element 920 and allows, among other things, for the sensing element 920 to be held in place with respect to the frame 918 prior to placement of the PCB 922. The PCB 922 and frame 918 include corresponding cutout portions 946, 948 which are configured to accept the sensor cable (not shown).

The PCB cutout portion 946 also includes a circular portion which is configured to accept a button post 944 positioned in the center of the cavity 930. The button post 944 is configured to receive the button 912 (FIG. 9B). The frame 918, shielding layers 926, 928, adhesive layer 924, and sensing element 920 each include injection holes 935 extending through opposing sides of the respective components. Additionally, in an assembled configuration the injection holes 935 of the various components line up with the holes 935 of the other components such that a syringe or other device can be inserted through the holes. Glue is injected into the holes 935 using the syringe, bonding the assembled components together.

Referring now to FIG. 9E, a lower cavity 936 is disposed on the underside of the frame 918 and has a depth d. In an assembled configuration, the sensing element 920 is wrapped around the frame 918 in the direction of the transverse axis 938 such that the lower planar portion 962 of the sensing element 920 stretches across the top of the lower cavity 936. As such, the lower cavity 936 can serve as an acoustic chamber of the multi-parameter sensor assembly. The sensing element 920 thus has freedom to move up into the acoustic chamber in response to acoustic vibrations, allowing for the mechanical deformation of the piezoelectric sensing material and generation of the corresponding electrical signal. In addition, the chamber of certain embodiments allows sound waves incident on the sensing element to reverberate in the chamber. As such, the sound waves from the patient may be amplified or more effectively directed to the sensing element 920, thereby improving the sensitivity of the sensing element 920. As such, the cavity 936 allows for improved operation of the sensor.

Figure 9F:
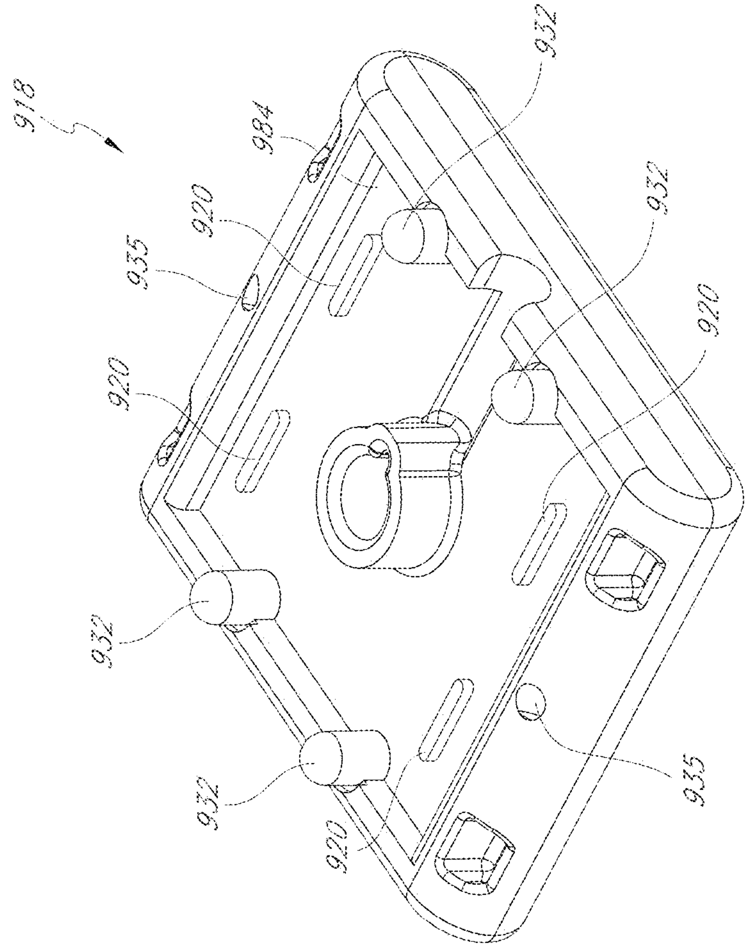
FIG. 9F shows a top perspective view of an embodiment of a support frame of the sensor subassembly of FIGS. 9A-9C.

The frame may include one or more contacts extending from the frame which press into corresponding contact strips of the PCB, helping to ensure a stable, relatively constant contact resistance between the PCB and the sensing element. FIG. 9F shows a top perspective view of an embodiment of a support frame 918 including such contacts. The frame 918 may be generally similar in structure and include one or more of the features of the frame shown in FIGS. 9D-9E, such as the locking posts 332 and the upper surface 384. The frame 918 further includes one or more contact bumps 920 which press into corresponding contact strips 923 (FIG. 2E) of the PCB 922 when the sensor sub-assembly is assembled. For example, the contact bumps 920 may include generally narrow rectangular raised segments and may be positioned on the upper surface 984 of the frame 918.

The contact bumps 920 help ensure a stable, constant contact resistance between the PCB 922 and the sensing element 920. The contact bumps 920 are dimensioned to press a portion of the sensing element 920 into the PCB 922 when the sensor subassembly 902 is assembled. In some embodiments, the height of the contact bumps 920 is from about 0.1 to about 1 mm. In some embodiments, the height of the contact bumps 920 is in the range from about 0.2 to about 0.3 mm. In one embodiment, the contact bumps 920 have a height of about 0.26 mm. The height is generally selected to provide adequate force and pressure between the sensing element 920 and PCB 922.

In other embodiments, the contact bumps may have different shapes. For example, the bumps 920 may be generally circular, oval, square or otherwise shaped such that the bumps 920 are configured to press into corresponding contact strips 923 on the PCB 922. The contact strips 923 may be shaped differently as well. For example, the strips 923 may be shaped so as to generally correspond to the cross-sectional shape of the bumps 920. While there are two bumps 920 per contact strip 923 in the illustrated embodiment, other ratios of contact bumps 920 to contract strips 923 are possible. For example, there may be one contact bump 920 per contact strip 923, or more than two contact bumps 920 per contact strip 923.

Referring again to FIGS. 9D-9E, the frame 918 includes rounded edges 934 around which the various components including the inner shield 926, the bonding layer 924, the sending element 920, and the outer shield 928 wrap in the direction of the transverse axis 938. The rounded edges 934 help assure that the sensing element 920 and other layers 926, 924, 928 extend smoothly across the frame 3116, and do not include wrinkles, folds, crimps and/or unevenness. Rounded edges 934 advantageously allow uniform application of the sensing element 920 to the frame 918, which helps assure uniform, accurate performance of the sensor assembly 902. In addition, the dimensions of the rounded corners and the upper cavity 930 can help to control the tension provided to the sensing element 920 when it is stretched across the frame 918.

The frame 918 may have different shapes or configurations. For example, in some embodiments, the frame 918 does not include a recess 930 and the PCB 922 sits on top of the frame 918. In one embodiment the edges 934 are not rounded. The frame 918 may be shaped as a board, for example. The frame 918 may include one or more holes. For example, the frame 918 includes four elongate bars connected to form a hollow rectangle in one configuration. In various embodiments, the frame 918 may not be generally rectangular but may instead be generally shaped as a square, circle, oval or triangle, for example. The shape of the frame 918 may be selected so as to advantageously allow the sensor subassembly 902 to be applied effectively to different areas of the body, for example. The shape of the frame 918 may also be selected so as to conform to the shape of one or more of the other components of the sensor system 900 such as the sensing element 920.

In addition, in some embodiments, one or more of the inner shield 926, the bonding layer 924, the sensing layer 920 and the outer shield 928 are not wrapped around the frame 918. For example, in one embodiment, one or more of these components are generally coextensive with and attached to the underside of the frame 918 and do not include portions which wrap around the edges 934 of the frame.

Sensing Element

The sensing element 920 of certain embodiments is configured to sense acoustic vibrations from a measurement site of a medical patient. In one embodiment, the sensing element 920 is a piezoelectric film, such as described in U.S. Pat. No. 6,661,161, incorporated in its entirety by reference herein, and in the ’883 application. Referring still to FIGS. 9D-9E, the sensing element 920 includes upper portions 972 and lower planar portion 962. As will be discussed, in an assembled configuration, the top of the upper portions 972 include electrical contacts which contact electrical contacts on the PCB 922, thereby enabling transmission of electrical signals from the sensing element 920 for processing by the sensor system. The sensing element 920 can be formed in a generally “C” shaped configuration such that it can wrap around and conform to the frame 918. Sensing elements in accordance with embodiments described herein can also be found in the ’883 Application. In some embodiments, the sensing element 920 includes one or more of crystals of tourmaline, quartz, topaz, cane sugar, and/or Rochelle salt (sodium potassium tartrate tetrahydrate). In other embodiments, the sensing element 920 includes quartz analogue crystals, such as berlinite ($AlPO_4$) or gallium orthophosphate ($GaPO_4$), or ceramics with perovskite or tungsten-bronze structures ($BaTiO_3$, $SrTiO_3$, $Pb(ZrTi)O_3$, $KNbO_3$, $LiNbO_3$, $LiTaO_3$, $BiFeO_3$, $Na_xWO_3$, $Ba_2NaNb_5O_5$, $Pb_2KNb_5O_{15}$).

In other embodiments, the sensing element 920 is made from a polyvinylidene fluoride plastic film, which develops piezoelectric properties by stretching the plastic while placed under a high pooling voltage. Stretching causes the film to polarize and the molecular structure of the plastic to align. For example, stretching the film under or within an electric field causes polarization of the material’s molecules into alignment with the field. A thin layer of conductive metal, such as nickel-copper or silver is deposited on each side of the film as electrode coatings, forming electrical poles. The electrode coating provides an electrical interface between the film and a circuit.

In operation, the piezoelectric material becomes temporarily polarized when subjected to a mechanical stress, such as a vibration from an acoustic source. The direction and magnitude of the polarization depend upon the direction and magnitude of the mechanical stress with respect to the piezoelectric material. The piezoelectric material will produce a voltage and current, or will modify the magnitude of a current flowing through it, in response to a change in the mechanical stress applied to it. In one embodiment, the electrical charge generated by the piezoelectric material is proportional to the change in mechanical stress of the piezoelectric material.

Piezoelectric material generally includes first and second electrode coatings applied to the two opposite faces of the material, creating first and second electrical poles. The voltage and/or current through the piezoelectric material are measured across the first and second electrical poles. Therefore, stresses produced by acoustic waves in the piezoelectric material will produce a corresponding electric signal. Detection of this electric signal is generally performed by electrically coupling the first and second electrical poles to a detector circuit. In one embodiment, a detector circuit is provided with the PCB 922, as described in greater detail below.

By selecting the piezoelectric material's properties and geometries, a sensor having a particular frequency response and sensitivity can be provided. For example, the piezoelectric material's substrate and coatings, which generally act as a dielectric between two poles, can be selected to have a particular stiffness, geometry, thickness, width, length, dielectric strength, and/or conductance. For example, in some cases stiffer materials, such as gold, are used as the electrode. In other cases, less stiff materials, such as silver, are employed. Materials having different stiffness can be selectively used to provide control over sensor sensitivity and/or frequency response.

The piezoelectric material, or film, can be attached to, or wrapped around, a support structure, such as the frame 918. As shown in FIGS. 9D-9E, the geometry of the piezoelectric material can be selected to match the geometry of the frame. Overall, the sensor can optimized to pick up, or respond to, a particular desired sound frequency, and not other frequencies. The frequency of interest generally corresponds to a physiological condition or event that the sensor is intended to detect, such as internal bodily sounds, including, cardiac sounds (e.g., heart beats, valves opening and closing, fluid flow, fluid turbulence, etc.), respiratory sounds (e.g., breathing, inhalation, exhalation, wheezing, snoring, apnea events, coughing, choking, water in the lungs, etc.), or other bodily sounds (e.g., swallowing, digestive sounds, gas, muscle contraction, joint movement, bone and/or cartilage movement, muscle twitches, gastro-intestinal sounds, condition of bone and/or cartilage, etc.).

The surface area, geometry (e.g., shape), and thickness of the piezoelectric material 920 generally defines a capacitance. The capacitance is selected to tune the sensor to the particular, desired frequency of interest. Furthermore, the frame 918 is structured to utilize a desired portion and surface area of the piezoelectric material.

The capacitance of the sensor can generally be expressed by the following relationship: $C=\varepsilon S/D$, where C is the sensor's capacitance, E is the dielectric constant associated with the material type selected, S is the surface area of the material, and D is the material thickness (e.g., the distance between the material's conducive layers). In one embodiment, the piezoelectric material (having a predetermined capacitance) is coupled to an sensor impedance (or resistance) to effectively create a high-pass filter having a predetermined high-pass cutoff frequency. The high-pass cutoff frequency is generally the frequency at which filtering occurs. For example, in one embodiment, only frequencies above the cutoff frequency (or above approximately the cutoff frequency) are transmitted.

The amount of charge stored in the conductive layers of the piezoelectric material 920 is generally determined by the thickness of its conductive portions. Therefore, controlling material thickness can control stored charge. One way to control material thickness is to use nanotechnology or MEMS techniques to precisely control the deposition of the electrode layers. Charge control also leads to control of signal intensity and sensor sensitivity. In addition, as discussed above, mechanical dampening can also be provided by controlling the material thickness to further control signal intensity and sensor sensitivity.

In addition, controlling the tension of the sensing element 920 in the region where the mechanical stress (e.g., mechanical stress due to acoustic vibration from a patient's skin) is incident upon the sensing element 920 can serve to improve the sensitivity of the sensing element 920 and/or the coupling between the source of the signal (e.g., the patient's skin) and the sensing element 920. This feature will be discussed in greater detail below with respect to the coupler 914.

Figure 10B:
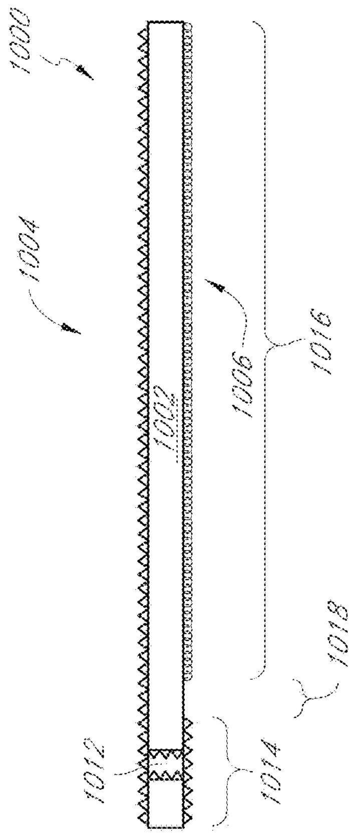
FIG. 10B is a cross-sectional view of the sensing element of FIG. 10A along the line 10B-20B.
Figure 10A:
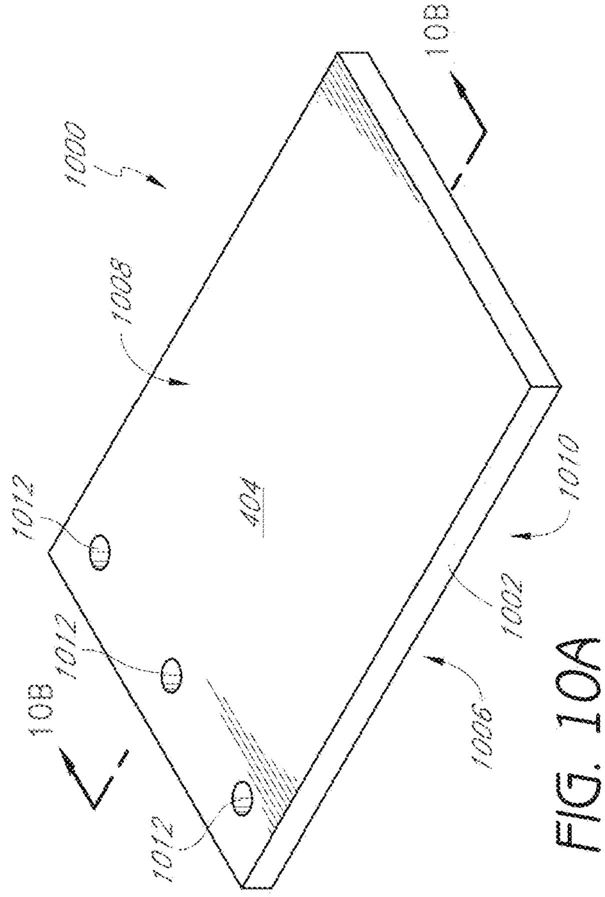
FIG. 10A a perspective view of a sensing element according to an embodiment of the disclosure usable with the sensor assembly of FIG. 9A.
Figure 10C:
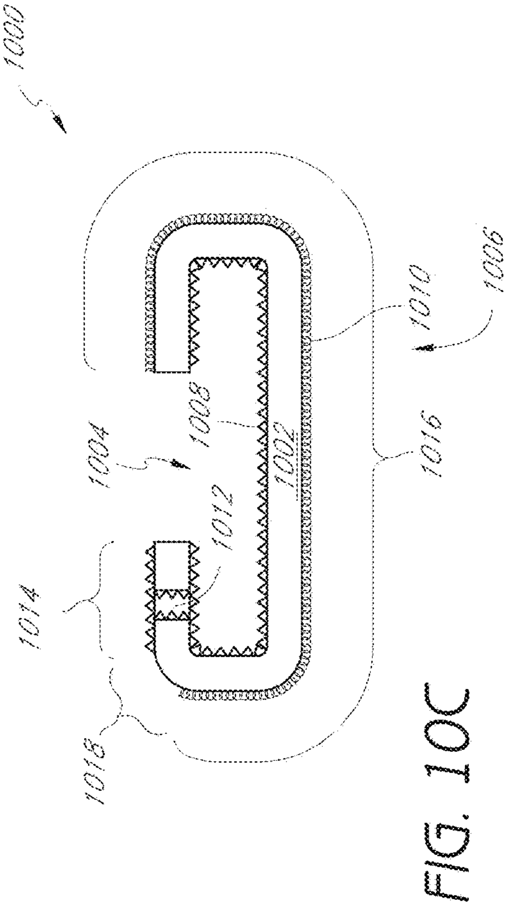
FIG. 10C is a cross-sectional view of the sensing element of FIGS. 10A-B shown in a wrapped configuration.

One embodiment of a piezoelectric sensing element 1000 is provided in FIGS. 10A-C. The sensing element 1000 includes a substrate 1002 and coatings 1004, 1006 on each of its two planar faces 1008, 1010. The planar faces 1008, 1010 are substantially parallel to each other. At least one through hole 1012 extends between the two planar faces 1008, 1010. In one embodiment, the sensing element 1000 includes two or three through holes 1012.

In one embodiment, a first coating 1004 is applied to the first planar face 1008, the substrate 1002 wall of the through holes 1012, and a first conductive portion 1014 of the second planar face 1010, forming a first electrical pole. By applying a first coating 1004 to the through holes 1012, a conductive path is created between the first planar face 1008 and the first conductive portion 1014 of the sensing element 1000. A second coating 1006 is applied to a second conductive portion 1016 of the second planar face 1010 to form a second electrical pole. The first conductive portion 1014 and second conductive portion 1016 are separated by a gap 1018 such that the first conductive portion 1014 and second conductive portion 1016 are not in contact with each other. In one embodiment, the first conductive portion 1014 and second conductive portion 1016 are electrically isolated from one another.

In some embodiments, the first and second conductive portions 1014, 1016 are sometimes referred to as masked portions, or coated portions. The conductive portions 1014, 1016, can be either the portions exposed to, or blocked from, material deposited through a masking, or deposition process. However, in some embodiments, masks aren't used. Either screen printing, or silk screening process techniques can be used to create the first and second conductive portions 1014, 1016.

In another embodiment, the first coating 1004 is applied to the first planar face 1008, an edge portion of the substrate 1002, and a first conductive portion 1014. By applying the first coating 1004 to an edge portion of the substrate 1002, through holes 1012 can optionally be omitted.

In one embodiment, the first coating 1004 and second coating 1006 are conductive materials. For example, the coatings 1004, 1006 can include silver, such as from a silver deposition process. By using a conductive material as a coating 1004, 1006, the multi-parameter sensor assembly can function as an electrode as well.

Electrodes are devices well known to those of skill in the art for sensing or detecting the electrical activity, such as the electrical activity of the heart. Changes in heart tissue polarization result in changing voltages across the heart muscle. The changing voltages create an electric field, which induces a corresponding voltage change in an electrode positioned within the electric field. Electrodes are typically used with echo-cardiogram (EKG or ECG) machines, which provide a graphical image of the electrical activity of the heart based upon signal received from electrodes affixed to a patient's skin.

Therefore, in one embodiment, the voltage difference across the first planar face 1008 and second planar face 1010 of the sensing element 1000 can indicate both a piezoelectric response of the sensing element 1000, such as to physical aberration and strain induced onto the sensing element 1000 from acoustic energy released from within the body, as well as an electrical response, such as to the electrical activity of the heart. Circuitry within the sensor assembly and/or within a physiological monitor (not shown) coupled to the sensor assembly distinguish and separate the two information streams. One such circuitry system is described in U.S. Provisional No. 60/893,853, filed Mar. 8, 2007, titled, "Multi-parameter Physiological Monitor," which is expressly incorporated by reference herein.

Referring still to FIGS. 10A-C, the sensing element 1000 is flexible and can be wrapped at its edges, as shown in FIG. 10C. In one embodiment, the sensing element 1000 is the sensing element 920 wrapped around the frame 918, as shown in FIGS. 9D and 9E. In addition, by providing both a first conductive portion 1014 and a second conductive portion 1016, both the first coating 1004 and second coating 1006 and therefore the first electrical pole of and the second electrical pole of the sensing element 1000 can be placed into direct electrical contact with the same surface of the PCB, such as the PCB 922 as shown FIGS. 5A-B below. This advantageously provides symmetrical biasing of the sensing element 1000 under tension while avoiding uneven stress distribution through the sensing element 1000.

Bonding Layer

Referring back to FIGS. 9D-9E, the bonding layer 924 (sometimes referred to as an insulator layer) of certain embodiments is an elastomer and has adhesive on both of its faces. In other embodiments, the bonding layer 924 is a rubber, plastic, tape, such as a cloth tape, foam tape, or adhesive film, or other compressible material that has adhesive on both its faces. For example, in one embodiment, the bonding layer 924 is a conformable polyethylene film that is double coated with a high tack, high peel acrylic adhesive. The bonding layer 924 in some embodiments is about 2, 4, 6, 8 or 10 millimeters thick.

The bonding layer 924 advantageously forms a physical insulation layer or seal between the components of the sensor subassembly 902 preventing substances entering and/or traveling between certain portions of the sensor subassembly 902. In many embodiments, for example, the bonding layer 924 forms a physical insulation layer that is water resistant or water proof, thereby providing a water-proof or water-resistant seal. The water-resistant properties of the bonding layer 924 provides the advantage of preventing moisture from entering the acoustic chamber or lower cavity 936. In certain embodiments, the sensing element 920, the bonding layer 924 and/or the shield layers 926, 928 (described below) form a water resistant or water proof seal. The seal can prevent moisture, such as perspiration, or other fluids, from entering portions of the sensor subassembly 902, such as the cavity 936 when worn by a patient. This is particularly advantageous when the patient is wearing the multi-parameter sensor assembly 900 during physical activity. The water-resistant seal prevents current flow and/or a conductive path from forming from the first surface of the sensing element 920 to its second surface or vice versa as a result of patient perspiration or some other moisture entering and/or contacting the sensing element 920 and/or sensor assembly 915.

The bonding layer 924 can also provide electrical insulation between the components of the sensor subassembly 902, preventing the flow of current between certain portions of the sensor subassembly 902. For example, the bonding layer 924 also prevents the inside electrical pole from shorting to the outside electrical pole by providing electrical insulation or acting as an electrical insulator between the components. For example, in the illustrated embodiment, the bonding layer 924 provides electrical insulation between the sensing element 920 and the inner shield layer 926, preventing the inside electrical pole of the sensing element 920 from shorting to the outside electrical pole. In another embodiment, a bonding layer is placed between the outer surface of the sensing element 920 and the outer shield layer 928.

The elasticity or compressibility of the bonding layer 924 can act as a spring and provide some variability and control in the pressure and force provided between the sensing element 920 and PCB 922. In some embodiments, the sensor assembly does not include a bonding layer 924.

Electrical Noise Shielding Barrier

An electrical noise shielding barrier can electrically shield the electrical poles of the sensing element from external electrical noises. In some embodiments the electrical shielding barrier can include one or more layers which form a Faraday cage around a piezoelectric sensing element, and which distribute external electrical noise substantially equally to the electrical poles of the piezoelectric sensing element. In addition, the shielding barrier flexibly conforms to the surface shape of the piezoelectric element as the surface shape of the piezoelectric element changes, thereby improving the shielding and sensor performance.

Referring still to FIGS. 9D-9E, the electrical shielding barrier 927 of the illustrated embodiment includes first and second shield layers 926, 928 (also referred to herein as inner and outer shield layers 926, 928) which form a Faraday cage (also referred to as a Faraday shield) which encloses the sensing element 920 and acts to reduce the effect of noise on the sensing element from sources such as external static electrical fields, electromagnetic fields, and the like. As will be described, one or more of the inner and outer shield layers 926, 928 advantageously conform to the contours of the sensing element 920 during use, allowing for enhanced shielding of the sensing element from external electrical noise.

The inner and outer shield layers 926, 928 include conductive material. For example, the inner and outer shield layers 926, 928 include copper in certain embodiments and are advantageously formed from a thin copper tape such that the layers can conform to the shape, contours and topology of the sensor element 920 and the frame 918. In some configurations, other materials (e.g., other metals) or other combinations of materials can be used. Moreover, as described herein with respect to FIGS. 9-13B, the electrical shielding barrier 927 or portions thereof, such as one or more of the first and second shield layers 926, 928, can be formed from piezoelectric films. In such embodiments, the sensor 915 can include first and second piezoelectric films arranged in a stack, and the shielding barrier 927 can be formed from the outer electrode of each film in the stack.

In various embodiments, one or more of the inner and outer shield layers 926, 928 are from between about 0.5 micrometer and 10 micrometers thick. For example, the shield layers 926, 928, may be from between about 1.5 and about 6 micrometers thick. In one embodiment, the inner and outer shield layers 926, 928 include copper tape about 3 micrometers thick. In yet other embodiments, the shield layers 926, 928 may be greater than 10 micrometers thick or less than 0.5 micrometers thick. In general, the thickness of the shield layer 926, 928 is selected to provide improved electrical shielding while allowing for the shield layers 926, 928 to conform to the sensor element 920 and/or the frame 918. The inner shield layer 926 includes an adhesive on the inside surface 952 such that it can adhere to the frame 918. The inner shield layer 926 adheres directly to the frame 918 and advantageously conforms to the contours of the frame such as the rounded edges 934 and the lower cavity 936, adhering to the surface 950 defining the base of the cavity 936. The bonding layer 924 (e.g., a tape adhesive) is wrapped around and generally conforms to the contours of the inner shield layer 926 and the frame 918. The sensing element 920 is wrapped around the bonding layer 924, the inner shield layer 924 and the frame 918. The outer shield layer 928 is wrapped around and advantageously conforms to the contours of the sensing element 920 and the frame 918. In certain embodiments, a bonding or insulating layer is positioned between the sensing element 920 and the outer shielding layer 928 as well. As such, the sensing element 920 is sandwiched between and enclosed within the inner and outer shield layers 926, 928 which form a Faraday cage around the sensing element 920. The configuration of the shield layers 926, 928, the sensing element 920 and the bonding layer 924 will be described in greater detail below with respect to FIGS. 5A-B.

In certain embodiments, the shield layers 926, 928 are coupled to a common potential (e.g., ground) or are otherwise operatively coupled, and each of the shield layers 926, 928 are also electrically (e.g., capacitively) coupled to one of the poles of the sensing element 920. For example, the shielding layer 926 may be capacitively coupled to the first electrode of the sensing element 920, and the shielding layer 928 may be capacitively coupled to the second electrode of the sensing element 920.

As discussed, the electrical shielding barrier 927 such as the Faraday cage formed by the inner and outer shield layers 926, 928 helps to reduce the effect of noise electrical noise on the sensing element 920 from sources such as external static electrical fields and electromagnetic fields, thereby lowering the noise floor, providing better noise immunity, or both. For example, the electrical shielding barrier 927 allows for the removal of electrical interference or noise incident directed towards the sensing element 920 while allowing the non-noise component of the sensed signal indicative of bodily sounds to be captured by the sensor 915. For example, in one embodiment the sensing element 920 is a piezoelectric film such as one of the piezoelectric films described herein having positive and negative electrical poles and configured in a differential mode of operation. The electrical shielding barrier 927 acts to balance the effect of the noise by distributing at least a portion of the noise substantially equally to the positive and negative electrical poles of the piezoelectric element. In some embodiments, the electrical shielding barrier 927 distributes the noise equally to both the positive and negative poles. Moreover, the noise signals distributed to the positive and negative electrical poles are substantially in phase or actually in phase with each other. For example, the noise signals distributed to the positive and negative poles are substantially similar frequencies and/or amplitudes with substantially no phase shift between them.

For example, in certain embodiments, noise incident on the shielding barrier 927 is substantially equally distributed to each of the shielding layers 926, 928 because these layers are at a common potential (e.g., ground). The substantially equally distributed noise may then be coupled (e.g., capacitively coupled) to the poles of the sensing element 920. In certain embodiments, at least some of the external electrical noise is shunted or otherwise directed to ground by the shield layers 926, 928 instead of, or in addition to, being distributed to the poles of the sensing element 920.

Because the noise signal components on the positive and negative poles are substantially in phase, the difference between the noise components on the respective poles is negligible or substantially negligible. On the other hand, the difference between the differential non-noise sensor signal components indicative of bodily sounds on the positive and negative poles will be non-zero because the sensing element is configured in a differential mode. As such, the noise signals can advantageously be removed or substantially removed through a common-mode rejection technique.

For example, a common-mode rejection element may receive a signal including the combined noise and non-noise sensor signal components of the positive and negative poles, respectively. The common-mode rejection element is configured to output a value indicative of the difference between the combined signal on the positive pole and the combined signal on the negative pole. Because the difference between the noise signals is negligible, the output of the common-mode rejection element will be substantially representative of the non-noise component of the sensor signal and not include a significant noise component. The common mode rejection element may include, for example, an operational amplifier. In one embodiment, for example, three operational amplifiers (not shown) are used and they are disposed on the PCB 922.

Because the shielding layers 926, 928 conform to the topology of the frame 918 and the sensing element 920, the shielding layers 926, 928 are physically closer to the electrical poles of the sensing element 920 and are more uniformly displaced from the sensing element 920. Moreover, the outer shield layer 928 of certain embodiments actively moves with and conforms to the contours of the sensing element 920 during use, such as when the sensor assembly is placed against the skin or when the sensing element 920 is moving due to acoustic vibrations. For example, when placed against the skin, the coupling element 958 pushes against both the outer shielding layer 928 of the shielding barrier 927 and the sensing element 920, causing them to curve along the inside surface of the coupling element 958 (FIG. 5A). Because the cage is flexible and can conform to the movement of the shielding element 920, the shielding performance and sensor performance is improved. This arrangement provides advantages such as for example, for the noise signals to be more accurately and evenly distributed to the positive and negative electrical poles of the sensing element 920 by the shielding layers 926, 928, thereby providing enhanced noise reduction. This arrangement can also provide for improved manufacturability and a more stream-lined design.

Alternative configurations for the electrical shielding barrier 927 are possible. For example, the inner shield layer may not include an adhesive layer and may, for example, be held in place against the frame 918 by pressure (e.g., from the locking posts 932). The outer shield 928 may also include an adhesive layer in some embodiments. In various other embodiments, the shield layers 926, 928 may include other materials such as other types of metals. One or more of the shield layers may be relatively rigid in some configurations. In one embodiment, an insulating layer or bonding layer is disposed between sensing element 920 and the outer shield layer 928. In some embodiments, the inner shield layer 926 actively conforms to the contours of the sensing element 920 during use in addition to the outer shield layer 928. In another embodiment, the inner shield layer 926 actively conforms to the sensing element 920 during use and the outer shield layer 928 does not. In yet other embodiments, the sensor assembly 901 does not include an electrical shielding barrier 927.

Acoustic Coupler

The sensor may also include an acoustic coupler or biasing element, which advantageously improves the coupling between the source of the signal to be measured by the sensor (e.g., the patient's skin) and the sensing element. The acoustic coupler generally includes a coupling portion positioned to apply pressure to the sensing element so as to bias the sensing element in tension. For example, the acoustic coupler may include one or more bumps, posts or raised portions which provide such tension. The bumps, posts or raised portions may be positioned on the inner surface of the coupler, the outer surface of the coupler, or both and may further act to evenly distribute pressure across the sensing element. In addition, the acoustic coupler can be further configured to transmit bodily sound waves to the sensing element. The acoustic coupler can also be configured to provide electrical isolation between the patient and the electrical components of the sensor.

In the illustrated embodiment, the acoustic coupler 914 houses the other components of the sensor subassembly including the frame 918, the PCB 922, the shield layers 926, 928, the bonding layers 924 and the sensing element 920. The acoustic coupler 914 includes a non-conductive material or dielectric. As shown, the acoustic coupler 914 generally forms a dielectric barrier between the patient and the electrical components of the sensor assembly 901. As such, the acoustic coupler 914 provides electrical isolation between the patient and the electrical components of the sensor subassembly 902. This is advantageous in avoiding potential harmful electrical pathways or ground loops forming between the patient and the sensor.

As shown in FIGS. 9D-9E, the acoustic coupler 914 is formed in a hollow shell capable of housing the components of the other sensor subassembly 902. Referring to FIG. 9D, the acoustic coupler 914 of the illustrated embodiment also includes recesses 956 and holes 952 capable of receiving and securing the button 912 (FIG. 9B) and portions of the elongate member 910 (FIG. 9B) of the attachment subassembly 904.

Figure 11:
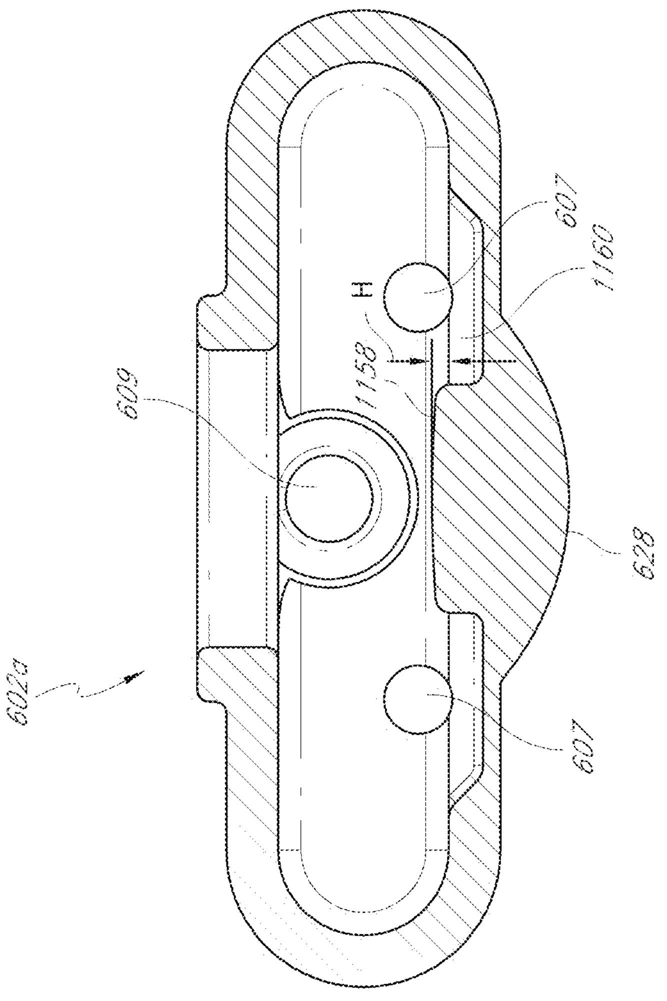
FIG. 11 is a cross-sectional view of the coupler of FIGS. 9A-9E taken along the line 11-11 shown in FIG. 9D.

FIG. 11 is a cross-sectional view of the acoustic coupler 602*a* taken along the line 11-11. In certain embodiments, the acoustic coupler 602*a* includes a bump or protrusion 1158 on the inner surface of the coupler 602*a* and configured to advantageously bias the sensing membrane in tension. For example, a coupling element 1158 is disposed on the on the interior bottom portion of the acoustic coupler 602*a* and which biases the sensing element (e.g., 620, 621) in tension. The coupling element 1158 of the illustrated embodiment is a generally rectangular bump which extends by a height h above the cavity 1160 which is formed on the interior bottom of the acoustic coupler 602*a*. The coupling element 1158 is centered about and extends along the longitudinal axis 940 (FIGS. 9D and 9E) from near the front of the acoustic coupler 602*a* to near the back of the acoustic coupler 602*a*. Also shown are the air vent holes 607 and cable sleeve 609.

In the illustrated embodiment, the coupling element 1158 is about % of the width of the acoustic coupler 602*a* along the transverse axis 938. As will be discussed in greater detail below with respect to FIG. 13A-B, the coupling element 1158 can advantageously bias the sensing element 620, 621 in tension by applying pressure to the sensing element. Because the sensing element may be generally taut in tension under the pressure of the coupling bump 1158, the sensing element can be mechanically coupled to the coupling bump 1158 and responsive to acoustic vibrations travelling through the coupler 602*a* to the sensing element, thereby providing improved coupling between the patient's skin and the sensing element. As such, the acoustic coupler 602*a* can provide for improved measurement sensitivity, accuracy, or both, among other advantages.

The acoustic coupler 602*a* is further configured to transmit bodily sound waves to the sensing element. The coupler 602*a* can further include a portion disposed on the outer surface of the coupler 602*a* and which is configured to contact the skin during use. For example, the acoustic coupler 602*a* can include an outer protrusion, bump or raised portion on the outer surface. Referring to FIG. 9E, the underside of the acoustic coupler 602*a* includes protrusion 628 which is configured to contact the skin of the patient and can provides contact between the skin and the acoustic coupler 602*a*. Acoustic vibrations from the skin will be incident on the portion 916, travel through the acoustic coupler to the coupling bump 628 and eventually be incident on the sensing element held in tension by the bump 628.

In addition, the contact portion 628 may, in conjunction with the coupling element 628 or on its own, also help to improve the coupling between the skin and the sensing element 920. For example, when pressed against the skin, the contact portion 628 may push a portion of the inner surface of the coupler 602*a*, such as the coupling element 1158, into the sensing element, advantageously holding the sensing element in tension. As shown, the contact portion 628 of the illustrated embodiment includes a semi-cylindrical bump mounted generally underneath the coupling element 1158. Similar to the coupling element 1158, the contact portion 628 is centered about and extends along the longitudinal axis 940 from near the front of the acoustic coupler 602*a* to near the back of the acoustic coupler 602*a*. Moreover, the acoustic coupler 602*a* acts to evenly distribute pressure to the sensing element 920 during use. For example, because the coupling element 1158 and the portion 628 are generally positioned such that they are centered with respect to surface of the sensing element, pressure may be distributed symmetrically and/or evenly across the sensing element.

Figure 12:
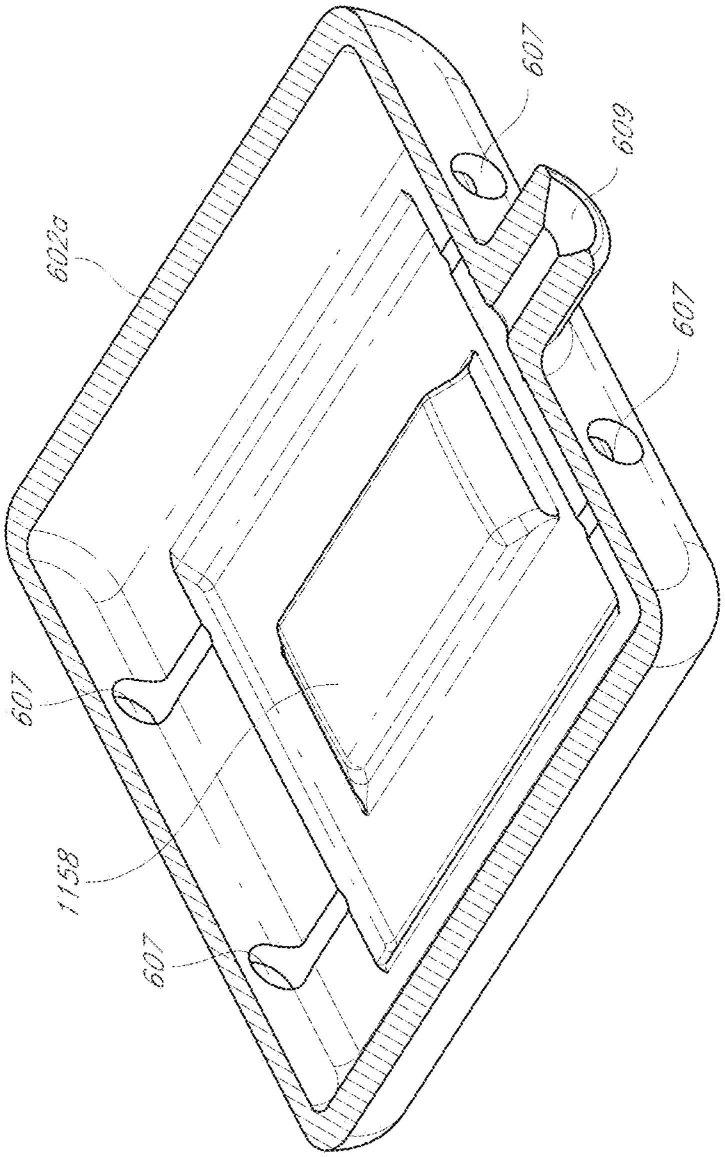
FIG. 12 is a cross-sectional view of the coupler of FIGS. 9A-9E taken along the line 12-12 shown in FIG. 9D.

FIG. 12 is a cross-sectional view of the acoustic coupler 602*a* taken along the line 12-12. This view shows the air vent holes 607 in both sides of the acoustic coupler 602*a*, as well as the coupling element 1158 and cable sleeve 609. The coupling element 1158 may, but need not, extend the entire width of the sensing elements.

Referring to FIG. 9E, a pair of slots 964 are disposed on either end of the contact portion 916 and each run generally along the transverse axis from near the left side of the acoustic coupler 914 of FIGS. 9A-9D to the right side of the acoustic coupler 914. The slots serve to decouple a segment 966 of the bottom of the acoustic coupler 914 including the coupling element 958 and the contact portion 916 from the remainder of the acoustic coupler 914. As such, the segment 966 can move at least partially independent from the rest of the acoustic coupler 914 in response to acoustic vibrations on the skin of the patient, thereby efficiently transmitting acoustic vibrations to the sensing element 920. The acoustic coupler 914 of certain embodiments includes an elastomer such as, for example, rubber or plastic material.

In an alternative embodiment of the acoustic coupler 914, for example, the acoustic coupler 914 does not include a hollow shell and does not house the other components of the sensor subassembly. For example, the coupler 914 may include a single planar portion such as, for example, a board which couples to the underside of the frame 918 such that the shielding layers 926, 928, the sensing element 920 and the bonding layer 924 are positioned between the coupler 914 and the frame 918. In some configurations, the coupler 914 is positioned between the frame 918 and one or more of the shielding layers 926, 928, the sensing element 920 and the bonding layer 924. Moreover, the acoustic coupler 914 may include a dielectric material, which advantageously electrically isolates the electrical components of the sensor subassembly 902 from the patient. For example, the dielectric layer may ensure that there is no electrical connection or continuity between the sensor assembly and the patient.

In certain embodiments, portions of the sensor assembly such as, for example, the acoustic coupler 914 may include a gel or gel-like material. The gel may provide beneficial acoustic transmission, for example, serving to enhance the coupling between the acoustic vibrations from the patient's skin and the sensing element 920. The gel may provide acoustic impedance matching, for example, between the skin and the sensor. For example, the gel may serve to reduce the impedance mismatch from potential skin-to-air and air-to-sensing element discontinuity, thereby reducing potential reflections and signal loss. The gel may be embedded in a portion of the acoustic coupler 914. For example, one or more of the coupling element 958 and the contact portion 916 may include a gel or gel-like material. The acoustic coupler 914 may include an embedded gel in certain embodiments where one or more of the coupling element 958 and the contact portion 916 are not included. For example, the entire patient contact portion of the acoustic coupler 914 may include gel material extending substantially from the patient contact surface to the interior of the coupler 914 across the contact portion. One or more columns of gel material may extend from the patient contact surface of the coupler 914 to the interior of the coupler 914 in other embodiments. In yet further embodiments, the gel is not embedded in the acoustic coupler 914 but is added to the skin directly. In one embodiment, the gel is embedded in the acoustic coupler 914 and is configured to be released from the coupler 914 when the sensor assembly is applied to the patient. For example, gel can be filled in one or more cavities of the acoustic coupler 914 prior to use wherein the cavities are configured to open and release the gel when the coupler is pressed against the skin.

Figure 13B:
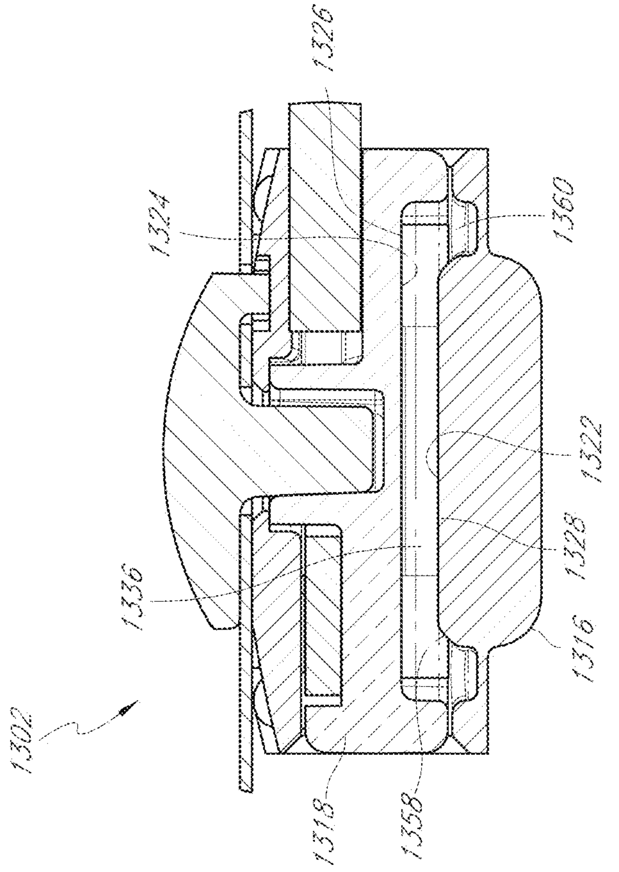
FIGS. 13A-13B are cross-sectional views of the sensor subassembly of FIGS. 9B-9C along the lines 13A-13A and 13B-13B, respectively.
Figure 13A:
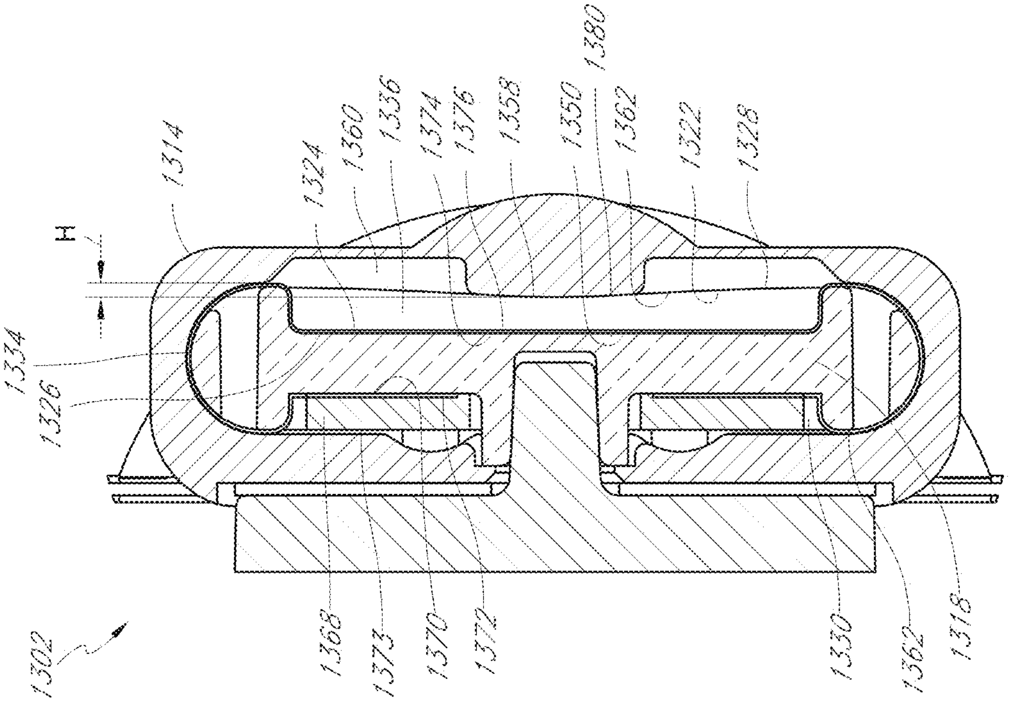

FIGS. 13A-B are cross-sectional views of the sensor subassembly 902 of FIG. 9 along the lines 13A-13A and 13B-13B, respectively. As shown, the inner copper shield 926 is positioned as the inner most of the shield layers 926, 928, the bonding layer 924 and the sensing element 920. Referring to FIGS. 9D-E and FIGS. 13A-B, the four tabs 968 of the inner copper shield 926 are flat and extend across the top of the frame recess 930 and the four corners of the top surface of the PCB (not shown in FIGS. 13A-B) which sits in the frame recess 930. The bonding layer 924 is wrapped around the inner copper shield 926. The upper portions 970 of the bonding layer 924 bend downward to conform to the shape of the frame 918 such that they extend across and contact the bottom of the frame cavity 930. The sensing element 920 is wrapped around the bonding layer 924 and the upper portions 972 of the sensing element 920 also bend downward to conform to the shape of the frame 918. As such, the upper portions 972 of the sensing element 920 extend across the bottom of the frame cavity 930 and are in contact with the bottom of the PCB 922 and the top surface of the bonding layer 924. The outer copper layer 928 is wrapped around the sensing element 920 and the upper planar portions 973 of the outer copper shield 928 are flat, extend across the top of the frame recess 930, and are in contact with the top surface of the PCB (not shown).

The shield layers 926, 928, the bonding layer 924 and the sensing element 920 wrap around the rounded edges 934 of the frame 918. The lower planar portions 974, 976 of the inner shield layer 926 and the bonding layer 924 bend upwards so as extend across the bottom surface 950 of the frame 918. The lower planar portions 962, 980 of the sensing element 920 and the outer shield layer 928, on the other hand, extend between the lower frame cavity 936 and the coupler cavity 960. Moreover, the lower planar portions 962, 980 of the sensing element 920 and the outer shield layer 928 extend across the top of the coupling portion 958. Because the coupler portion 958 extends slightly above the coupler cavity 960 into the lower frame cavity 936 by the distance h, the sensing element 920 is advantageously biased in tension improving the sensitivity of the sensing element 920, the coupling of the sensing element 920 to acoustic vibrations in the skin of the patient (not shown), or both.

In various embodiments, the components of the sensor subassembly 902 may be arranged differently. For example, the components may be combined such that the overall assembly include fewer discrete components, simplifying manufacturability. In one embodiment, one or more of the shielding layers 926, 928, the bonding layer 924 and the sensing element 920 may include an integral portion (e.g., a multi-layered film). In some embodiments, more than one bonding layer 924 is used. In one embodiment, adhesive layers are formed on one or more of the shielding layers 926, 928 and the sensing element 920, and no separate bonding layer 924 is present. In another embodiment, the various layers are held together by pressure (e.g., from the contact posts 932 and/or PCB) instead of through the use of adhesives.

Referring still to FIGS. 9D-E and 13A-B, a method for attaching the shielding layers 926, 928, the bonding layer 924, the sensing element 920 and the PCB 922 to the frame 918 includes providing the inner shield 926 and attaching it to the frame 918. The sensing element 920 and bonding layer 924 are provided and also attached to the frame 918. A printed circuit board 922 is then provided. The printed circuit board 922 is placed on top of the sensing element 920 such that a first edge 980 of the printed circuit board 922 is placed over a first conductive portion of the sensing element 920, and a second edge 982 of the printed circuit board 922 is placed over a second conductive portion of the sensing element 920.

The printed circuit board 922 is pressed down into the sensing element 920 in the direction of the frame 918. As the printed circuit board 922 is pressed downward, the contact bumps (not shown) of the frame 918 push the bonding layer 924 and sensing element 920 into contact strips located along the first and second sides or edges 980, 982 of the printed circuit board 922. The contact strips of the printed circuit board 922 are made from conductive material, such as gold. Other materials having a good electro negativity matching characteristic to the conductive portions of the sensing element 920, may be used instead. The elasticity or compressibility of the bonding layer 924 acts as a spring, and provides some variability and control in the pressure and force provided between the sensing element 920 and printed circuit board 922.

Once the outer shield 928 is provided and attached to the frame 918, a desired amount of force is applied between the PCB 922 and the frame 918 and the locking posts 932 are vibrated or ultrasonically or heated until the material of the locking posts 932 flows over the PCB 922. The locking posts 932 can be welded using any of a variety of techniques, including heat staking, or placing ultrasonic welding horns in contact with a surface of the locking posts 932, and applying ultrasonic energy. Once welded, the material of the locking posts 932 flows to a mushroom-like shape, hardens, and provides a mechanical restraint against movement of the PCB 922 away from the frame 918 and sensing element 920. By mechanically securing the PCB 922 with respect to the sensing element 920, the various components of the sensor sub-assembly 902 are locked in place and do not move with respect to each other when the multi-parameter sensor assembly is placed into clinical use. This prevents the undesirable effect of inducing electrical noise from moving assembly components or inducing instable electrical contact resistance between the PCB 922 and the sensing element 920. In certain embodiments, the locking posts 932 provide these advantages substantially uniformly across multiple sensors.

Therefore, the PCB 922 can be electrically coupled to the sensing element 920 without using additional mechanical devices, such as rivets or crimps, conductive adhesives, such as conductive tapes or glues, like cyanoacrylate, or others. In addition, the mechanical weld of the locking posts 932 helps assure a stable contact resistance between the PCB 922 and the sensing element 920 by holding the PCB 922 against the sensing element 920 with a constant pressure, for example, and/or preventing movement between the PCB 922 and the sensing element 920 with respect to each other.

The contact resistance between the sensing element 920 and PCB 922 can be measured and tested by accessing test pads on the PCB 922. For example, in one embodiment, the PCB 922 includes three discontinuous, aligned test pads that overlap two contact portions between the PCB 922 and sensing element 920. A drive current is applied, and the voltage drop across the test pads is measured. For example, in one embodiment, a drive current of about 100 mA is provided. By measuring the voltage drop across the test pads the contact resistance can be determined by using Ohm's law, namely, voltage drop (V) is equal to the current (1) through a resistor multiplied by the magnitude of the resistance (R), or V=IR. While one method for attaching the shield layers 926, 928, the bonding layer 924, the sensing element and the PCB 922 to the frame 918 has been described, other methods are possible. For example, as discussed, in some embodiments, one or more of the various separate layers are combined in an integral layer which is attached to the frame 918 in one step.

Printed Circuit Board

The PCB 922 includes various electronic components mounted to either or both faces of the PCB 922. When sensor assembly is assembled and the PCB 922 is disposed in the upper frame cavity 930, some of the electronic components of the PCB 922 may extend above the upper frame cavity 930. To reduce space requirements and to prevent the electronic components from adversely affecting operation of the sensor assembly, the electronic components can be low-profile, surface mounted devices. The electronic components are often connected to the PCB 922 using conventional soldering techniques, for example the flip-chip soldering technique. Flip-chip soldering uses small solder bumps such of predictable depth to control the profile of the soldered electronic components. The four tabs 968 of the inner copper shield 926 and the upper planar portions 973 of the outer copper shield 928 are soldered to the PCB 922 in one embodiment, electrically coupling the electrical shielding barrier to the PCB 922.

In some embodiments, the electronic components include filters, amplifiers, etc. for pre-processing or processing a low amplitude electric signal received from the sensing element 920 (e.g., the operational amplifiers discussed above with respect to the Faraday cage) prior to transmission through a cable to a physiological monitor. In other embodiments, the electronic components include a processor or pre-processor to process electric signals. Such electronic components may include, for example, analog-to-digital converters for converting the electric signal to a digital signal and a central processing unit for analyzing the resulting digital signal.

In other embodiments, the PCB 922 includes a frequency modulation circuit having an inductor, capacitor and oscillator, such as that disclosed in U.S. Pat. No. 6,661,161, which is incorporated by reference herein. In another embodiment, the PCB 922 includes an FET transistor and a DC-DC converter or isolation transformer and phototransistor. Diodes and capacitors may also be provided. In yet another embodiment, the PCB 3114 includes a pulse width modulation circuit.

In one embodiment, the PCB 922 also includes a wireless transmitter, thereby eliminating mechanical connectors and cables. For example, optical transmission via at least one optic fiber or radio frequency (RF) transmission is implemented in other embodiments. In other embodiments, the sensor assembly includes an information element which can determine compatibility between the sensor assembly and the physiological monitor to which it is attached and provide other functions, as described below.

Coupler Attachment Tool

FIG. 14 depicts an embodiment of a coupler attachment tool 1400 that can be used to stretch the coupler 602*a* over the frame 606 and other sensor components. As described above, the coupler 602*a* can be made of a silicone material or the like that is flexible and therefore able to stretch over the frame 606. Because the coupler 602*a* is substantially enclosed, except for a hole 603 (also referred to as a "top hole") in the top of the coupler 602*a* and air vent holes 607 in certain embodiments, the coupler 602*a* does not slide over the frame 606 like the coupler 602*b*. Instead, the tool 1400 stretches the coupler through the hole 603 to enable the frame 606 to be inserted in to the stretched-out hole 603. Once the coupler 602*b* is taken off of the tool 1400, the hole 603 of the coupler 602*b* can stretch back to normal dimensions or approximately normal dimensions.

The example tool 1400 shown includes a clamp 1402 and an adjuster 1404. The clamp 1402 can attach the tool 1400 to a workbench or the like and is optional. The clamp 1402 is attached to the adjuster 1404 via screws 1461 that are screwed into a base 1440 of the adjuster 1404. A column 1438 extends from the base 1440 and supports the remaining components of the adjuster 1404.

The stretching mechanism of the adjuster 1404 is provided by stretching portions or partially-cylindrical members 1414, 1416 at the end of two arms 1410, 1412. The hole 603 of the coupler 602*a* can be inserted into the members 1414, 1416. The adjuster 1404 can facilitate pulling apart one of the arm 1412 away from the other arm 1410, thereby opening a gap between the two members 1414, 1416 and stretching the coupler 602*a*.

The two arms 1410, 1412 are attached (e.g., screwed) to base components 1432, 1436, 1430. Passing through the base components 1432, 1436, 1430 are rods 1422 and 1424, of which the rod 1422 is threaded. The rods 1424 are movably disposed in the bottom of the base components 1432, 1436, 1430 and connects to a brace 1470. The rod 1422 is threaded and is disposed in the base components 1432, 1436, 1430 and is also movably disposed in the brace 1470. A handle 1420 is attached to the rod 1422. When the handle 1420 is pulled back by a user, the rod 1422 is pulled through the brace 1470. In turn, the base component 1430 is pulled by the rod 1422, to which base component 1430 the arm 1412 is attached, thereby also pulling the arm 1412 and stretching an attached coupler 602*a*. Nuts 1442, 1444 screwed onto the rod 1422 stop against the side of the base component 1432 to prevent the coupler 602*a* from being stretched too far. The nuts 1442, 1444 are tightened against each other to prevent or reduce slipping. A gap 1450 between the nuts 1442, 1444 and the base component 1432 corresponds to a stretching distance pulled by the arms in the hole 603 of the coupler 602*a*. In an embodiment, the stretching distance is about 0.5 inches, although other stretching distances can be chosen depending on the size of the coupler 602*a*.

FIG. 15 shows a more detailed view of the arm 1410. Similar features can be provided for the arm 1412 but in mirror-view. The arm 1410 includes the stretching portion or partially-cylindrical member 1414 as well as screw holes 1460 for attachment to the base component 1432.

Information Element

In addition, the sensor assembly can include any of a variety of information elements, such as readable and/or writable memories. Information elements can be used to keep track of device usage, manufacturing information, duration of sensor usage, compatibility information, calibration information, identification information, other sensor, physiological monitor, and/or patient statistics, etc. The information element can communicate such information to a physiological monitor. For example, in one embodiment, the information element identifies the manufacturer, lot number, expiration date, and/or other manufacturing information. In another embodiment, the information element includes calibration information regarding the multi-parameter sensor. Information from the information element is provided to the physiological monitor according to any communication protocol known to those of skill in the art. For example, in one embodiment, information is communicated according to an $I^2C$ protocol. The information element may be provided on or be in electrical communication with the PCB 922. In various embodiments, the information element can be located in another portion of the sensor assembly. For example, in one embodiment, the information element is provided on a cable connected to the PCB 922. The information element may further be located on the sensor connector 905, the attachment subassembly 904, or some other part of the sensor assembly.

The information element can include one or more of a wide variety of memory devices known to an artisan from the disclosure herein, including an EPROM, an EEPROM, a flash memory, a combination of the same or the like. The information element can include a read-only device such as a ROM, a read and write device such as a RAM, combinations of the same, or the like. The remainder of the present disclosure will refer to such combination as simply EPROM for ease of disclosure; however, an artisan will recognize from the disclosure herein that the information element can include the ROM, the RAM, single wire memories, combinations, or the like.

The information element can advantageously store some or all of a wide variety data and information, including, for example, information on the type or operation of the sensor, type of patient or body tissue, buyer or manufacturer information, sensor characteristics including calculation mode data, calibration data, software such as scripts, executable code, or the like, sensor electronic elements, sensor life data indicating whether some or all sensor components have expired and should be replaced, encryption information, monitor or algorithm upgrade instructions or data, or the like. In some embodiments, the information element can be used to provide a quality control function. For example, the information element may provide sensor identification information to the system which the system uses to determine whether the sensor is compatible with the system.

In an advantageous embodiment, the monitor reads the information element on the sensor to determine one, some or all of a wide variety of data and information, including, for example, information on the type or operation of the sensor, a type of patient, type or identification of sensor buyer, sensor manufacturer information, sensor characteristics including history of the sensor temperature, the parameters it is intended to measure, calibration data, software such as scripts, executable code, or the like, sensor electronic elements, whether it is a disposable, reusable, or multi-site partially reusable, partially disposable sensor, whether it is an adhesive or non-adhesive sensor, sensor life data indicating whether some or all sensor components have expired and should be replaced, encryption information, keys, indexes to keys or has functions, or the like monitor or algorithm upgrade instructions or data, some or all of parameter equations, information about the patient, age, sex, medications, and other information that can be useful for the accuracy or alarm settings and sensitivities, trend history, alarm history, sensor life, or the like.

Terminology/Additional Embodiments

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, etc. described herein. A wide variety of variation is possible. Components, elements, and/or steps can be altered, added, removed, or rearranged. While certain embodiments have been explicitly described, other embodiments will become apparent to those of ordinary skill in the art based on this disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out all together (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. An acoustic sensor comprising:

an acoustic sensing element supported by a frame; and a one piece integral acoustic coupler that covers at least a portion of the frame and the acoustic sensing element, the acoustic coupler comprising one or more air vent holes on at least one sidewall of the acoustic coupler and aligned with corresponding pressure equalization pathways in the frame, wherein the acoustic coupler forms an acoustic chamber that provides an improved signal-to-noise ratio of the acoustic sensor.

2. The acoustic sensor of claim 1, wherein the acoustic coupler at least partially surrounds the frame.

3. The acoustic sensor of claim 2, wherein the acoustic sensing element is configured to output a signal responsive to acoustic vibrations associated with a patient when the acoustic sensor is attached to the patient.

4. The acoustic sensor of claim 3, wherein the acoustic coupler is configured to be coupled with an area of skin of the patient, wherein a bottom surface of the acoustic coupler comprises a dielectric material that electrically decouples the area of the skin of the patient from the acoustic sensing element when the acoustic sensor is attached to the patient.

5. The acoustic sensor of claim 4, wherein the bottom surface of the acoustic coupler has no openings and forms a barrier between the patient and the acoustic sensing element.

6. The acoustic sensor of claim 5, wherein the acoustic coupler comprises a silicone material.

7. The acoustic sensor of claim 5, wherein the frame defines an acoustic cavity and is configured to support the acoustic sensing element across the acoustic cavity.

8. The acoustic sensor of claim 7 further comprising:

at least one pressure equalization pathway of the pressure equalization pathways extending from the acoustic cavity to ambient air pressure.

9. The acoustic sensor of claim 8, wherein the at least one pressure equalization pathway comprises at least one of a notch or hole.

10. The acoustic sensor of claim 8, wherein the acoustic coupler comprises equal numbers of air vent holes on opposite sidewalls of the acoustic coupler, and wherein the frame comprises equal numbers of pressure equalization pathways on corresponding opposite sides of the frame.

11. The acoustic sensor of claim 10, wherein the frame comprises two pressure equalization pathways of the pressure equalization pathways on each of opposite sides of the frame.

12. The acoustic sensor of claim 11 further comprising:

a cable in communication with the acoustic sensing element and configured to communicate the signal to an acoustic monitor.

13. The acoustic sensor of claim 8, wherein the frame comprises at least two pressure equalization pathways of the pressure equalization pathways that are symmetrically positioned on the frame.

14. A method comprising:

detecting, by an acoustic sensor according to claim 1, acoustic vibrations, wherein the acoustic vibrations are transmitted to the acoustic sensing element via the acoustic coupler;

converting, by the acoustic sensing element, the acoustic vibrations into an electrical signal; and outputting the electrical signal.

* * * * *